(12) United States Patent
Tzvieli et al.

(10) Patent No.: US 10,045,726 B2
(45) Date of Patent: Aug. 14, 2018

(54) SELECTING A STRESSOR BASED ON THERMAL MEASUREMENTS OF THE FACE

(71) Applicant: Facense Ltd., Kiryat Tivon (IL)

(72) Inventors: Arie Tzvieli, Berkeley, CA (US); Gil Thieberger, Kiryat Tivon (IL); Ari M Frank, Haifa (IL)

(73) Assignee: Facense Ltd., Kiryat Tivon (IL)

( * ) Notice: Subject to any disclaimer, the term of this patent is extended or adjusted under 35 U.S.C. 154(b) by 0 days.

(21) Appl. No.: 15/832,844

(22) Filed: Dec. 6, 2017

(65) Prior Publication Data

US 2018/0092587 A1 Apr. 5, 2018

Related U.S. Application Data

(63) Continuation-in-part of application No. 15/722,434, filed on Oct. 2, 2017, which is a continuation-in-part
(Continued)

(51) Int. Cl.
*A61B 5/16* (2006.01)
*A61B 5/01* (2006.01)
(Continued)

(52) U.S. Cl.
CPC .............. *A61B 5/165* (2013.01); *A61B 5/015* (2013.01); *A61B 5/4884* (2013.01);
(Continued)

(58) Field of Classification Search
CPC ....... A61B 5/0077; A61B 5/01; A61B 5/6803; A61B 5/7267; A61B 9/04; G02C 11/00;
(Continued)

(56) References Cited

U.S. PATENT DOCUMENTS 5,143,086 A 9/1992 Duret et al.
5,664,578 A 9/1997 Boczan
(Continued)

FOREIGN PATENT DOCUMENTS

EP 2233071 A1 9/2013
WO WO2016025323 2/2016

OTHER PUBLICATIONS

Alghoul, K., Alharthi, S., Al Osman, H., & El Saddik, A. (2017). Heart Rate Variability extraction from videos signals: ICA vs. EVM comparison. IEEE Access, 5, 4711-4719.
(Continued)

*Primary Examiner* — David Porta
*Assistant Examiner* — Faye Boosalis
(74) *Attorney, Agent, or Firm* — Active Knowledge Ltd.

(57) ABSTRACT

Described herein are systems and methods for selecting a stressor based on thermal measurements. In one embodiment, a system includes an inward-facing head-mounted thermal camera (CAM) and a computer. CAM takes thermal measurements of a region on a periorbital area ($TH_{ROI1}$) of the user. The computer detects extents of stress based on $TH_{ROI1}$, receives indications of potential stressors to which the user was exposed while $TH_{ROI1}$ were taken, and selects the stressor, from among the potential stressors, based on the indications and the extents. Optionally, during most of the time the user was affected by the stressor, the effect of the stressor, as manifested via changes to $TH_{ROI1}$, was higher than the effects of most of the potential stressors. Optionally, thermal measurements of other regions on the face may also be utilized to detect the extents of stress.

20 Claims, 16 Drawing Sheets

Related U.S. Application Data of application No. 15/182,592, filed on Jun. 14, 2016, and a continuation-in-part of application No. 15/231,276, filed on Aug. 8, 2016, and a continuation-in-part of application No. 15/284,528, filed on Oct. 3, 2016, application No. 15/832,844, which is a continuation-in-part of application No. 15/635,178, filed on Jun. 27, 2017, and a continuation-in-part of application No. 15/284,528, and a continuation-in-part of application No. 15/231,276, and a continuation-in-part of application No. 15/182,592, and a continuation-in-part of application No. 15/182,566, filed on Jun. 14, 2016, now Pat. No. 9,867,546.

(60) Provisional application No. 62/566,572, filed on Oct. 2, 2017, provisional application No. 62/408,677, filed on Oct. 14, 2016, provisional application No. 62/456,105, filed on Feb. 7, 2017, provisional application No. 62/480,496, filed on Apr. 2, 2017, provisional application No. 62/175,319, filed on Jun. 14, 2015, provisional application No. 62/202,808, filed on Aug. 8, 2015, provisional application No. 62/236,868, filed on Oct. 3, 2015, provisional application No. 62/354,833, filed on Jun. 27, 2016, provisional application No. 62/372,063, filed on Aug. 8, 2016, provisional application No. 62/480,496, filed on Apr. 2, 2017.

(51) Int. Cl.
*A61B 5/00* (2006.01)
*G02C 11/00* (2006.01)
*G06F 17/30* (2006.01)

(52) U.S. Cl.
CPC .............. *A61B 5/0077* (2013.01); *A61B 5/163* (2017.08); *A61B 5/6803* (2013.01); *G06F 17/30702* (2013.01)

(58) Field of Classification Search
CPC ...... G02C 11/04; G02C 2200/16; G02C 5/14; G02C 7/02
See application file for complete search history.

(56) References Cited

U.S. PATENT DOCUMENTS

| | | | |
|---|---|---|---|
| 6,121,953 | A | 9/2000 | Walker |
| 6,286,958 | B1 | 9/2001 | Koest et al. |
| 6,771,423 | B2 | 8/2004 | Geist |
| 6,837,615 | B2 | 1/2005 | Newman |
| 6,996,256 | B2 | 2/2006 | Pavlidis |
| 7,027,621 | B1 | 4/2006 | Prokoski |
| 7,135,980 | B2 | 11/2006 | Moore et al. |
| 7,138,905 | B2 | 11/2006 | Pavlidis et al. |
| 8,149,273 | B2 | 4/2012 | Liu et al. |
| 8,289,443 | B2 | 10/2012 | MacKenzie |
| 8,334,872 | B2 | 12/2012 | Epps et al. |
| 8,360,986 | B2 | 1/2013 | Farag et al. |
| 8,573,866 | B2 | 11/2013 | Bond et al. |
| 8,585,588 | B2 | 11/2013 | Kovarik et al. |
| 8,723,790 | B1 | 5/2014 | Schaefer |
| 8,768,438 | B2 | 7/2014 | Mestha et al. |
| 8,786,698 | B2 | 7/2014 | Chen et al. |
| 8,855,384 | B2 | 10/2014 | Kyal et al. |
| 8,964,298 | B2 | 2/2015 | Haddick et al. |
| 9,019,174 | B2 | 4/2015 | Jerauld |
| 9,020,185 | B2 | 4/2015 | Mestha et al. |
| 9,194,749 | B2 | 11/2015 | Pompei |
| 9,211,069 | B2 | 12/2015 | Larsen et al. |
| 9,410,854 | B2 | 8/2016 | Padiy |
| 9,569,734 | B2 | 2/2017 | Thieberger et al. |
| 2002/0080094 | A1 | 6/2002 | Biocca et al. |
| 2005/0083248 | A1 | 4/2005 | Biocca et al. |
| 2005/0271117 | A1 | 12/2005 | Grassl et al. |
| 2007/0047768 | A1 | 3/2007 | Gordon et al. |
| 2007/0248238 | A1 | 10/2007 | Abreu |
| 2007/0265507 | A1 | 11/2007 | de Lemos |
| 2008/0260212 | A1 | 10/2008 | Moskal et al. |
| 2009/0221888 | A1 | 9/2009 | Wijesiriwardana |
| 2009/0237564 | A1 | 9/2009 | Kikinis et al. |
| 2010/0191124 | A1 | 7/2010 | Prokoski |
| 2010/0280334 | A1 | 11/2010 | Carlson et al. |
| 2012/0062719 | A1 | 3/2012 | Debevec et al. |
| 2012/0105473 | A1 | 5/2012 | Bar-Zeev et al. |
| 2012/0197093 | A1 | 8/2012 | LeBoeuf et al. |
| 2012/0327194 | A1 | 12/2012 | Shiratori et al. |
| 2013/0124039 | A1 | 5/2013 | Abreu |
| 2013/0215244 | A1 | 8/2013 | Mestha et al. |
| 2013/0241805 | A1 | 9/2013 | Gomez |
| 2013/0257709 | A1 | 10/2013 | Raffle et al. |
| 2014/0180449 | A1 | 6/2014 | Sung |
| 2014/0282911 | A1 | 9/2014 | Bare et al. |
| 2014/0347265 | A1 | 11/2014 | Aimone et al. |
| 2014/0366049 | A1 | 12/2014 | Lehtiniemi et al. |
| 2015/0087924 | A1 | 3/2015 | Li et al. |
| 2015/0148618 | A1 | 5/2015 | Sitko et al. |
| 2015/0157255 | A1 | 6/2015 | Nduka |
| 2015/0297126 | A1 | 10/2015 | Atsumori et al. |
| 2015/0310263 | A1 | 10/2015 | Zhang et al. |
| 2015/0359443 | A1 | 12/2015 | Poh |
| 2016/0015289 | A1 | 1/2016 | Simon et al. |
| 2016/0081622 | A1 | 3/2016 | Abreu |
| 2016/0091877 | A1 | 3/2016 | Fullam et al. |
| 2016/0098592 | A1 | 4/2016 | Lee et al. |
| 2016/0100790 | A1 | 4/2016 | Cantu et al. |
| 2016/0170996 | A1 | 6/2016 | Frank et al. |
| 2016/0216760 | A1 | 7/2016 | Trutna et al. |
| 2016/0224803 | A1 | 8/2016 | Frank et al. |
| 2016/0235324 | A1 | 8/2016 | Mershin et al. |
| 2016/0270656 | A1 | 9/2016 | Samec et al. |
| 2016/0342835 | A1 | 11/2016 | Kaehler |
| 2017/0007167 | A1 | 1/2017 | Kostic et al. |
| 2017/0231490 | A1 | 8/2017 | Toth et al. |
| 2017/0235931 | A1 | 8/2017 | Publicover et al. |

OTHER PUBLICATIONS

Al-Khalidi, F. Q., Saatchi, R., Burke, D., Elphick, H., & Tan, S. (2011). Respiration rate monitoring methods: A review. Pediatric pulmonology, 46(6), 523-529.

Appel, V. C., Belini, V. L., Jong, D. H., Magalhães, D. V., & Caurin, G. A. (Aug. 2014). Classifying emotions in rehabilitation robotics based on facial skin temperature. In Biomedical Robotics and Biomechatronics (2014 5th IEEE RAS & EMBS International Conference on (pp. 276-280). IEEE.

Aryal, A., Ghahramani, A., & Becerik-Gerber, B. (2017). Monitoring fatigue in construction workers using physiological measurements. Automation in Construction.

Boccanfuso, L., & O'Kane, J. M. (Jun. 2012). Remote measurement of breathing rate in real time using a high precision, single-point infrared temperature sensor. In Biomedical Robotics and Biomechatronics (BioRob), 2012 4th IEEE RAS & EMBS International Conference on (pp. 1704-1709). IEEE.

Cardone, D., Pinti, P., & Merla, A. (2015). Thermal infrared imaging-based computational psychophysiology for psychometrics. Computational and mathematical methods in medicine, 2015.

Carine Collé, Re-Experience Big-Data, 3 months group project with Sanya Rai Gupta and Florian Puech, UK, London, RCA, IDE, 2014, Amoeba.

Choi, J. S., Bang, J. W., Heo, H., & Park, K. R. (2015). Evaluation of Fear Using Nonintrusive Measurement of Multimodal Sensors. Sensors, 15(7), 17507-17533.

Clay-Warner, J., & Robinson, D. T. (2015). Infrared thermography as a measure of emotion response. Emotion Review, 7(2), 157-162.

Cross, C. B., Skipper, J. A., & Petkie, D. (May 2013). Thermal imaging to detect physiological indicators of stress in humans. In SPIE Defense, Security, and Sensing (pp. 870501-870501). International Society for Optics and Photonics.

(56) References Cited

OTHER PUBLICATIONS

Fei, J., & Pavlidis, I. (Aug. 2006). Analysis of breathing air flow patterns in thermal imaging. In Engineering in Medicine and Biology Society, 2006. EMBS'06. 28th Annual International Conference of the IEEE (pp. 946-952). IEEE.
Fei, J., & Pavlidis, I. (2010). Thermistor at a distance: unobtrusive measurement of breathing. IEEE Transactions on Biomedical Engineering, 57(4), 988-998.
Fernández-Cuevas, I., Mains, J. C. B., Lastras, J. A., Carmona, P. M. G., Cano, S. P., García-Concepción, M. Á., & Sillero-Quintana, M. (2015). Classification of factors influencing the use of infrared thermography in humans: A review. Infrared Physics & Technology, 71, 28-55.
Ghahramani, A., Castro, G., Becerik-Gerber, B., & Yu, X. (2016). Infrared thermography of human face for monitoring thermoregulation performance and estimating personal thermal comfort. Building and Environment, 109, 1-11.
Hawkes, P. W. (2012). Advances in Imaging and Electron Physics (vol. 171). Academic Press. Chapter 2.
Hong, K., Yuen, P., Chen, T., Tsitiridis, A., Kam, F., Jackman, J., . . . & Lightman+, F. T. S. (Sep. 2009). Detection and classification of stress using thermal imaging technique. In Proc. of SPIE vol. (vol. 7486, pp. 748601-1).
Ioannou, S., Gallese, V., & Merla, A. (2014). Thermal infrared imaging in psychophysiology: potentialities and limits. Psychophysiology, 51(10), 951-963.
Jenkins, S. D., & Brown, R. D. H. (2014). A correlational analysis of human cognitive activity using Infrared Thermography of the supraorbital region, frontal EEG and self-report of core affective state. QIRT.
Johnson, M. L., Price, P. A., & Jovanov, E. (Aug. 2007). A new method for the quantification of breathing. In Engineering in Medicine and Biology Society, 2007. EMBS 2007. 29th Annual International Conference of the IEEE (pp. 4568-4571). IEEE.
Jovanov, E., Raskovic, D., & Hormigo, R. (2001). Thermistor-based breathing sensor for circadian rhythm evaluation. Biomedical sciences instrumentation, 37, 493-498.
Joyal, C. C., & Henry, M. (2013). Long-wave infrared functional brain imaging in human: a pilot study. The open neuroimaging journal, 7(1).
Kimura, S., Fukuomoto, M., & Horikoshi, T. (Sep. 2013). Eyeglass-based hands-free videophone. In Proceedings of the 2013 International Symposium on Wearable Computers (pp. 117-124). ACM.
Kurz, M., Hölzl, G., Riener, A., Anzengruber, B., Schmittner, T., & Ferscha, A. (Sep. 2012). Are you cool enough for Texas Hold'Em Poker?. In Proceedings of the 2012 ACM Conference on Ubiquitous Computing (pp. 1145-1149). ACM.
Lewis, G. F., Gatto, R. G., & Porges, S. W. (2011). A novel method for extracting respiration rate and relative tidal volume from infrared thermography. Psychophysiology, 48(7), 877-887.
Merla, A. (2014). Thermal expression of intersubjectivity offers new possibilities to human-machine and technologically mediated interactions.
Mizuno, T., & Kume, Y. (Aug. 2015). Development of a Glasses-Like Wearable Device to Measure Nasal Skin Temperature. In International Conference on Human-Computer Interaction (pp. 727-732). Springer International Publishing.
Mizuno, T., Sakai, T., Kawazura, S., Asano, H., Akehi, K., Matsuno, S., . . . & Itakura, N. (Jul. 2015). Facial Skin Temperature Fluctuation by Mental Work-Load with Thermography. In the International Conference on Electronics and Software Science (ICESS2015) Proceedings (pp. 212-215).
Murthy, R., & Pavlidis, I. (2006). Noncontact measurement of breathing function. IEEE Engineering in Medicine and Biology Magazine, 25(3), 57-67.
Murthy, R., Pavlidis, I., & Tsiamyrtzis, P. (Sep. 2004). Touchless monitoring of breathing function. In Engineering in Medicine and Biology Society, 2004. IEMBS'04. 26th Annual International Conference of the IEEE (vol. 1, pp. 1196-1199). IEEE.
Nagaraj, S., Quoraishee, S., Chan, G., & Short, K. R. (Apr. 2010). Biometric study using hyperspectral imaging during stress. In SPIE Defense, Security, and Sensing (pp. 76740K-76740K). International Society for Optics and Photonics.
Nhan, B. R., & Chau, T. (2010). Classifying affective states using thermal infrared imaging of the human face. IEEE Transactions on Biomedical Engineering, 57(4), 979-987.
Pavlidis, I., & Levine, J. (2002). Thermal image analysis for polygraph testing. IEEE Engineering in Medicine and Biology Magazine, 21(6), 56-64.
Pavlidis, I., Dowdall, J., Sun, N., Puri, C., Fei, J., & Garbey, M. (2007). Interacting with human physiology. Computer Vision and Image Understanding, 108(1), 150-170.
Puri, C., Olson, L., Pavlidis, I., Levine, J., & Starren, J. (Apr. 2005). StressCam: non-contact measurement of users' emotional states through thermal imaging. In CHI'05 extended abstracts on Human factors in computing systems (pp. 1725-1728). ACM.
Rajoub, B. A., & Zwiggelaar, R. (2014). Thermal facial analysis for deception detection. IEEE transactions on information forensics and security, 9(6), 1015-1023.
Ramirez, G. A., Fuentes, O., Crites Jr, S. L., Jimenez, M., & Ordonez, J. (2014). Color analysis of facial skin: Detection of emotional state. In Proceedings of the IEEE Conference on Computer Vision and Pattern Recognition Workshops (pp. 468-473).
Romera-Paredes, B., Zhang, C., & Zhang, Z. (Jul. 2014). Facial expression tracking from head-mounted, partially observing cameras. In Multimedia and Expo (ICME), 2014 IEEE International Conference on (pp. 1-6). IEEE.
Sharma, N., Dhall, A., Gedeon, T., & Goecke, R. (Sep. 2013). Modeling stress using thermal facial patterns: A spatio-temporal approach. In Affective Computing and Intelligent Interaction (ACII), 2013 Humaine Association Conference on (pp. 387-392). IEEE.
Sharma, N., Dhall, A., Gedeon, T., & Goecke, R. (2014). Thermal spatio-temporal data for stress recognition. EURASIP Journal on Image and Video Processing, 2014(1), 28.
Shastri, D., Papadakis, M., Tsiamyrtzis, P., Bass, B., & Pavlidis, I. (2012). Perinasal imaging of physiological stress and its affective potential. IEEE Transactions on Affective Computing, 3(3), 366-378.
Tsiamyrtzis, P., Dowdall, J., Shastri, D., Pavlidis, I. T., Frank, M. G., & Ekman, P. (2007). Imaging facial physiology for the detection of deceit. International Journal of Computer Vision, 71(2), 197-214.
Yang, M., Liu, Q., Turner, T., & Wu, Y. (Jun. 2008). Vital sign estimation from passive thermal video. In Computer Vision and Pattern Recognition, 2008. CVPR 2008. IEEE Conference on (pp. 1-8). IEEE.
Written opinion of the international searching authority, PCT/IB2017/056066, dated Jan. 29, 2018.
Written opinion of the international searching authority, PCT/IB2017/056067, dated Jan. 29, 2018.
Written opinion of the international searching authority, PCT/IB2017/056069, dated Jan. 29, 2018.

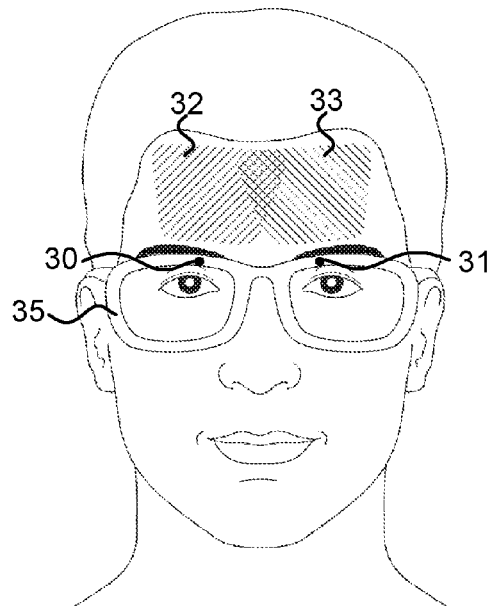
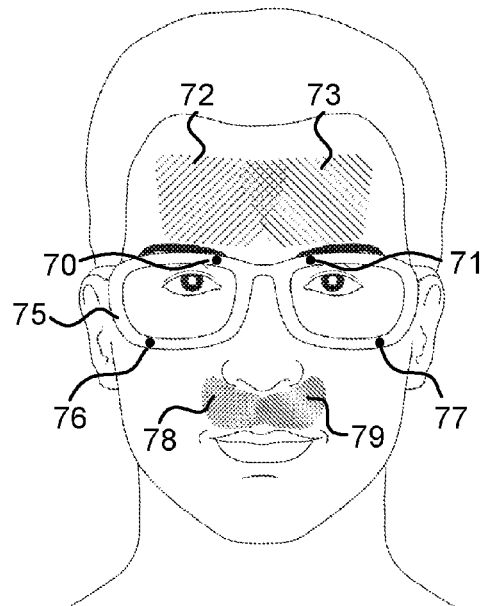
FIG. 6  FIG. 7
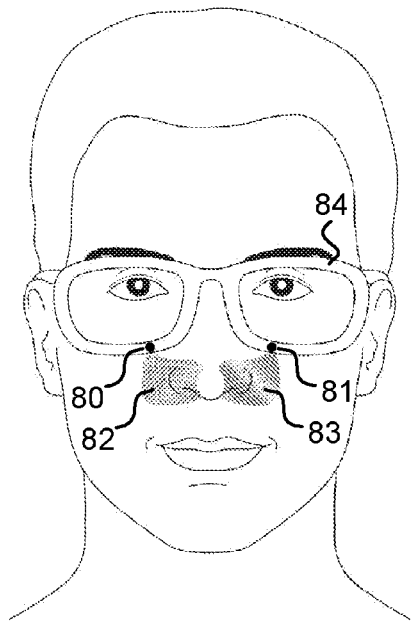
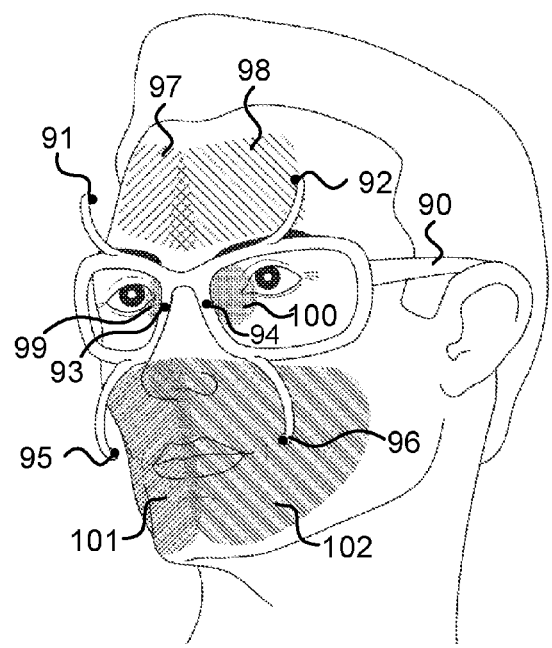
FIG. 8  FIG. 9

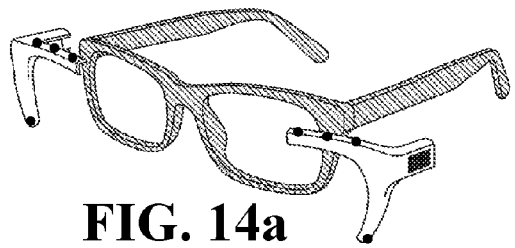
FIG. 14a
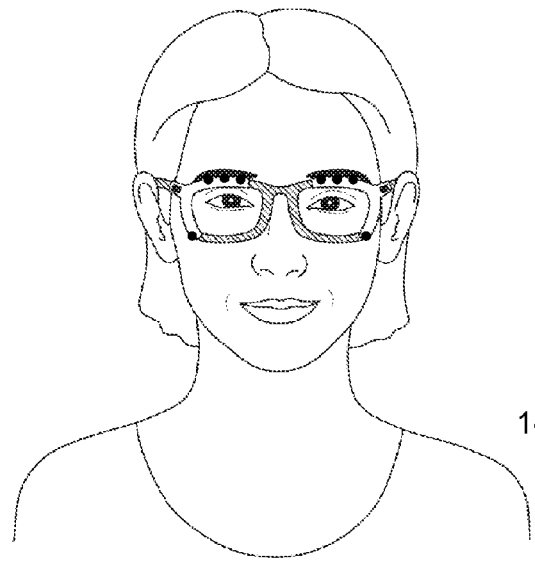
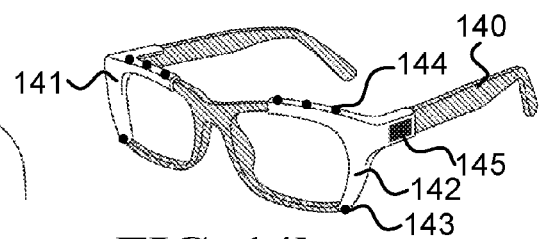
FIG. 14c
FIG. 14b
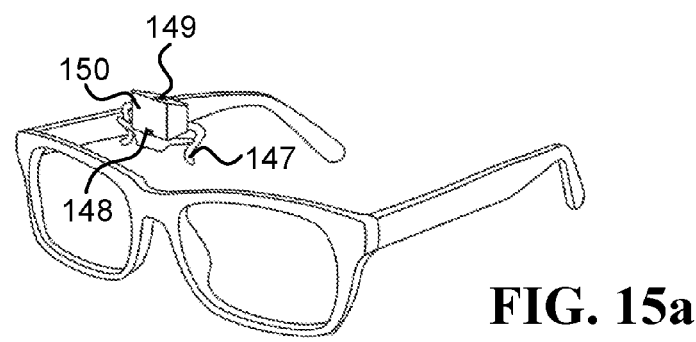
FIG. 15a
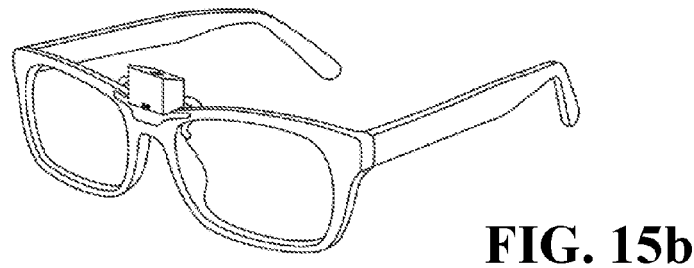
FIG. 15b

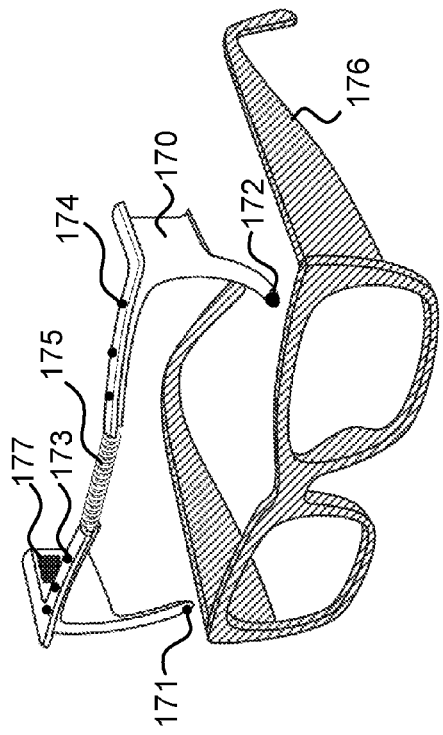
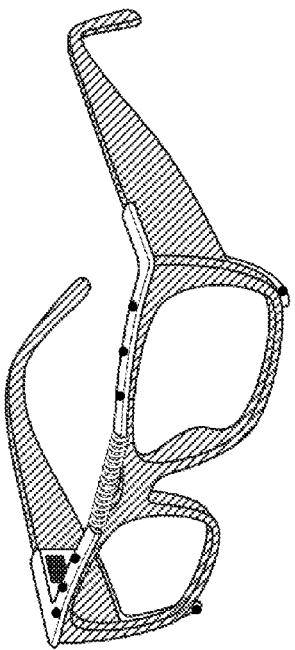
FIG. 17a
FIG. 17b
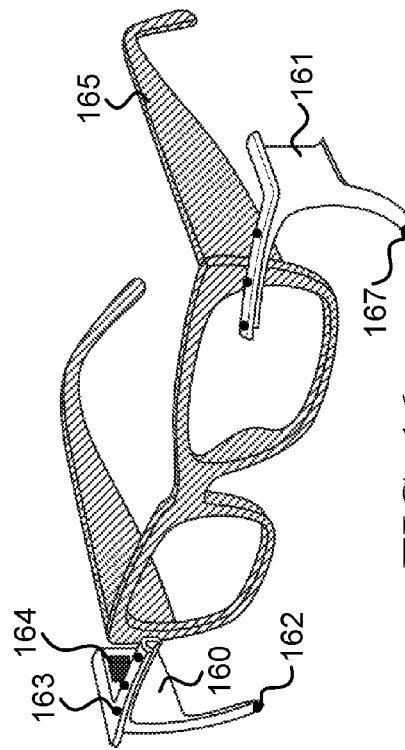
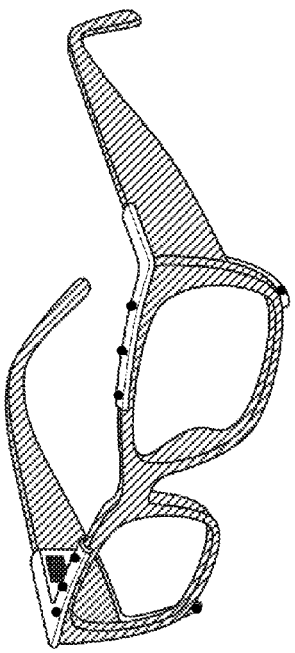
FIG. 16a
FIG. 16b

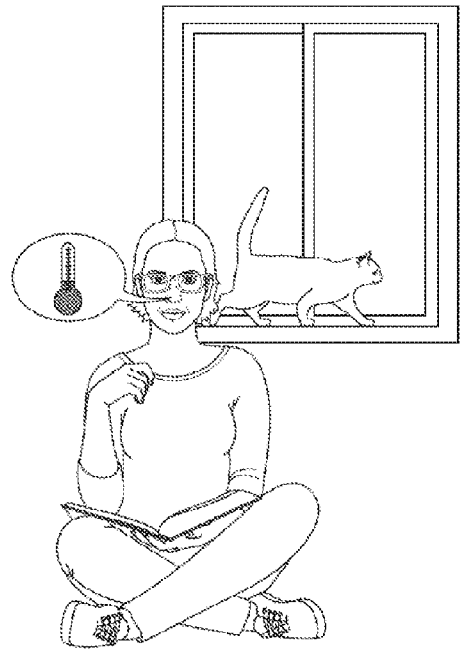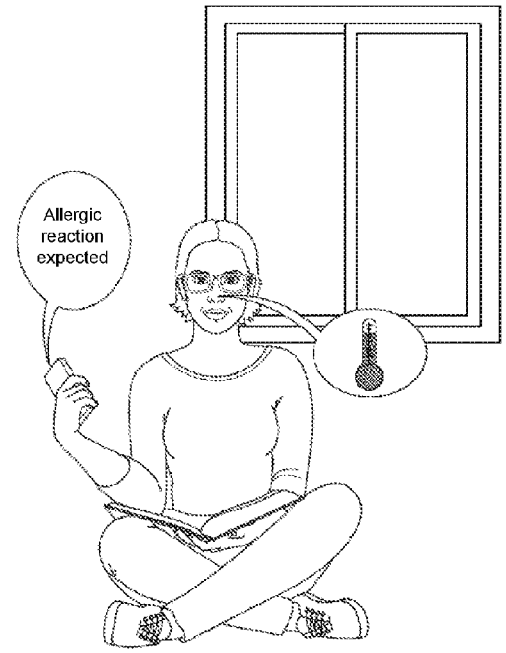
FIG. 24a  FIG. 24b
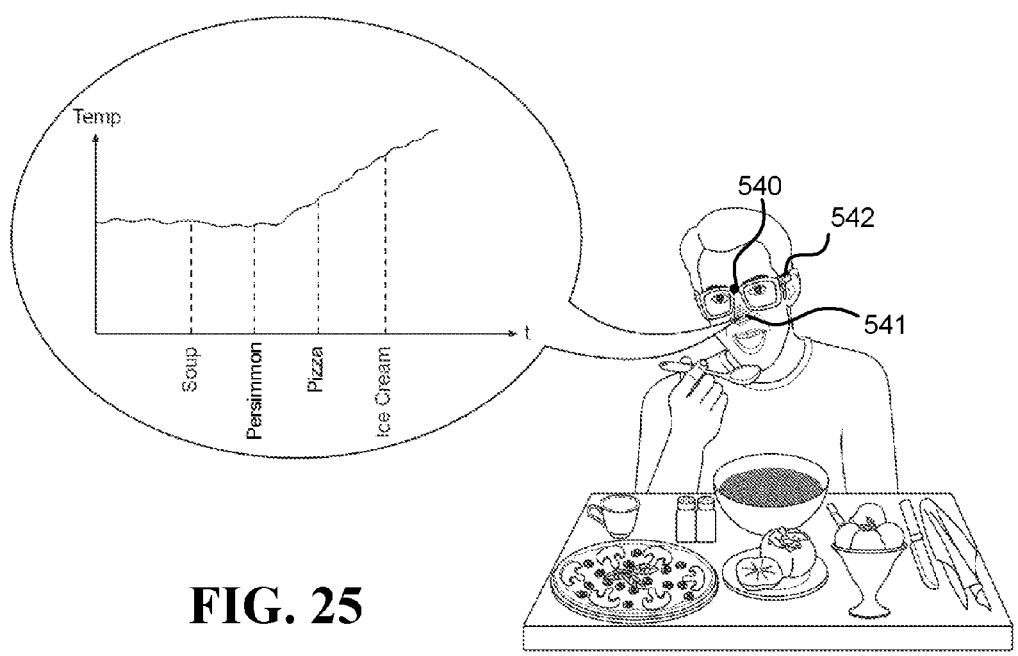
FIG. 25

SELECTING A STRESSOR BASED ON THERMAL MEASUREMENTS OF THE FACE

CROSS-REFERENCE TO RELATED APPLICATIONS

This Application claims priority to U.S. Provisional Patent Application No. 62/456,105, filed Feb. 7, 2017, and U.S. Provisional Patent Application No. 62/480,496, filed Apr. 2, 2017, and U.S. Provisional Patent Application No. 62/566,572, filed Oct. 2, 2017. U.S. Provisional Patent Application No. 62/566,572 is herein incorporated by reference in its entirety.

This Application is a Continuation-In-Part of U.S. application Ser. No. 15/182,566, filed Jun. 14, 2016, now U.S. Pat. No. 9,867,546, which claims priority to U.S. Provisional Patent Application No. 62/175,319, filed Jun. 14, 2015, and U.S. Provisional Patent Application No. 62/202,808, filed Aug. 8, 2015.

This Application is also a Continuation-In-Part of U.S. application Ser. No. 15/182,592, filed Jun. 14, 2016, which claims priority to U.S. Provisional Patent Application No. 62/175,319, filed Jun. 14, 2015, and U.S. Provisional Patent Application No. 62/202,808, filed Aug. 8, 2015.

This Application is also a Continuation-In-Part of U.S. application Ser. No. 15/231,276, filed Aug. 8, 2016, which claims priority to U.S. Provisional Patent Application No. 62/202,808, filed Aug. 8, 2015, and U.S. Provisional Patent Application No. 62/236,868, filed Oct. 3, 2015.

This Application is also a Continuation-In-Part of U.S. application Ser. No. 15/284,528, filed Oct. 3, 2016, which claims priority to U.S. Provisional Patent Application No. 62/236,868, filed Oct. 3, 2015, and U.S. Provisional Patent Application No. 62/354,833, filed Jun. 27, 2016, and U.S. Provisional Patent Application No. 62/372,063, filed Aug. 8, 2016.

This Application is also a Continuation-In-Part of U.S. application Ser. No. 15/635,178, filed Jun. 27, 2017, which claims priority to U.S. Provisional Patent Application No. 62/354,833, filed Jun. 27, 2016, and U.S. Provisional Patent Application No. 62/372,063, filed Aug. 8, 2016.

This Application is also a Continuation-In-Part of U.S. application Ser. No. 15/722,434, filed Oct. 2, 2017, which claims priority to U.S. Provisional Patent Application No. 62/408,677, filed Oct. 14, 2016, and U.S. Provisional Patent Application No. 62/456,105, filed Feb. 7, 2017, and U.S. Provisional Patent Application No. 62/480,496, filed Apr. 2, 2017. U.S. Ser. No. 15/722,434 is also a Continuation-In-Part of U.S. application Ser. No. 15/182,592, filed Jun. 14, 2016, which claims priority to U.S. Provisional Patent Application No. 62/175,319, filed Jun. 14, 2015, and U.S. Provisional Patent Application No. 62/202,808, filed Aug. 8, 2015. U.S. Ser. No. 15/722,434 is also a Continuation-In-Part of U.S. application Ser. No. 15/231,276, filed Aug. 8, 2016, which claims priority to U.S. Provisional Patent Application No. 62/202,808, filed Aug. 8, 2015, and U.S. Provisional Patent Application No. 62/236,868, filed Oct. 3, 2015. And U.S. Ser. No. 15/722,434 is also a Continuation-In-Part of U.S. application Ser. No. 15/284,528, filed Oct. 3, 2016, which claims priority to U.S. Provisional Patent Application No. 62/236,868, filed Oct. 3, 2015, and U.S. Provisional Patent Application No. 62/354,833, filed Jun. 27, 2016, and U.S. Provisional Patent Application No. 62/372,063, filed Aug. 8, 2016.

ACKNOWLEDGMENTS

Gil Thieberger would like to thank his holy and beloved teacher, Lama Dvora-hla, for her extraordinary teachings and manifestation of wisdom, love, compassion and morality, and for her endless efforts, support, and skills in guiding him and others on their paths to freedom and ultimate happiness. Gil would also like to thank his beloved parents for raising him exactly as they did.

BACKGROUND

Experiencing stress is generally detrimental to people's health. Reducing the amount of stress a user experiences in day-to-day life typically requires knowing when the user is stressed, for how long, and in what conditions. While many physiological responses, including stress, are manifested in the temperatures and/or temperature changes at various regions of the human face, collecting such data over time when people are going through their daily activities can be very difficult. Typically, collection of such data involves utilizing thermal cameras that are bulky, expensive and need to be continually pointed at a person's face. Additionally, due to the people's movements in their day-to-day activities, collecting the required measurements often involves performing various complex image analysis procedures, such as procedures involving image registration and face tracking. Thus, there is a need to be able to collect thermal measurements at various regions of a person's face in order to detect stress.

SUMMARY

Throughout a person's daily life, various factors can increase a person's stress level, such as conducting a certain activity, being in a certain location, or interacting with a certain entity. A factor that increases a user's stress may be considered a stressor. There are various factors that may be considered potential stressors; however, they may influence different users differently.

One aspect of this disclosure involves monitoring a user's stress level, which can help detect which of the various potential stressors should in fact be considered actual stressors (since they increase the user's stress). In one embodiment, a system that selects a stressor includes an inward-facing head-mounted thermal camera (CAM) and a computer. CAM takes thermal measurements of a region on a periorbital area ($TH_{ROI1}$) of the user. The computer detects extents of stress based on $TH_{ROI1}$, receives indications of times during which the user was exposed to potential stressors, and selects the stressor, from among the potential stressors, based on the indications and the extents. During most of the time the user was affected by the stressor, the effect of the stressor, as manifested via changes to $TH_{ROI1}$, was higher than the effects of most of the potential stressors.

BRIEF DESCRIPTION OF THE DRAWINGS

The embodiments are herein described by way of example only, with reference to the following drawings:

FIG. 6, FIG. 7, FIG. 8 and FIG. 9 illustrate head-mounted systems (HMSs) configured to measure various ROIs relevant to some of the embodiments describes herein;

FIG. 14a, FIG. 14b, and FIG. 14c illustrate embodiments of two right and left clip-on devices that are configured to attached/detached from an eyeglasses frame;

FIG. 15a and FIG. 15b illustrate an embodiment of a clip-on device that includes inward-facing head-mounted cameras pointed at the lower part of the face and the forehead;

FIG. 16a and FIG. 16b illustrate embodiments of right and left clip-on devices that are configured to be attached behind an eyeglasses frame;

FIG. 17a and FIG. 17b illustrate an embodiment of a single-unit clip-on device that is configured to be attached behind an eyeglasses frame;

FIG. 24a and FIG. 24b illustrate a scenario in which a user is alerted about an expected allergic reaction;

FIG. 25 illustrates how the system may be utilized to identify a trigger of an allergic reaction;

DETAILED DESCRIPTION

Figure 1A:
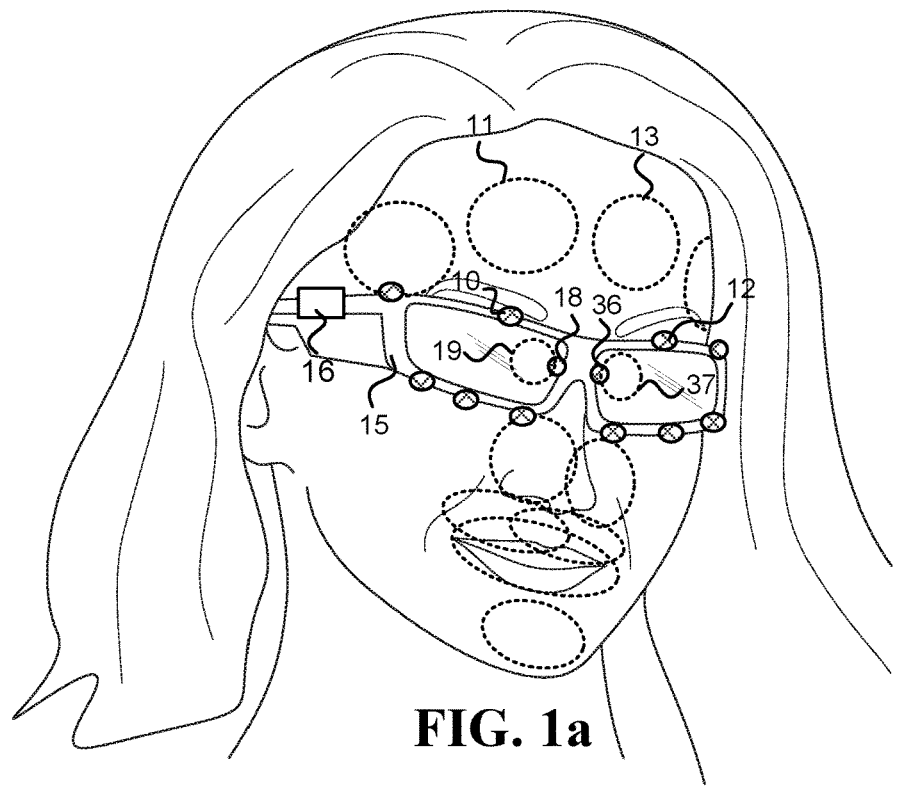
FIG. 1a and FIG. 1b illustrate various inward-facing head-mounted cameras coupled to an eyeglasses frame.

A "thermal camera" refers herein to a non-contact device that measures electromagnetic radiation having wavelengths longer than 2500 nanometer (nm) and does not touch its region of interest (ROI). A thermal camera may include one sensing element (pixel), or multiple sensing elements that are also referred to herein as "sensing pixels", "pixels", and/or focal-plane array (FPA). A thermal camera may be based on an uncooled thermal sensor, such as a thermopile sensor, a microbolometer sensor (where microbolometer refers to any type of a bolometer sensor and its equivalents), a pyroelectric sensor, or a ferroelectric sensor.

Sentences in the form of "thermal measurements of an ROI" (usually denoted $TH_{ROI}$ or some variant thereof) refer to at least one of: (i) temperature measurements of the ROI ($T_{ROI}$), such as when using thermopile or microbolometer sensors, and (ii) temperature change measurements of the ROI ($\Delta T_{ROI}$), such as when using a pyroelectric sensor or when deriving the temperature changes from temperature measurements taken at different times by a thermopile sensor or a microbolometer sensor.

In some embodiments, a device, such as a thermal camera, may be positioned such that it occludes an ROI on the user's face, while in other embodiments, the device may be positioned such that it does not occlude the ROI. Sentences in the form of "the system/camera does not occlude the ROI" indicate that the ROI can be observed by a third person located in front of the user and looking at the ROI, such as illustrated by all the ROIs in FIG. 7, FIG. 11 and FIG. 19. Sentences in the form of "the system/camera occludes the ROI" indicate that some of the ROIs cannot be observed directly by that third person, such as ROIs 19 and 37 that are occluded by the lenses in FIG. 1a, and ROIs 97 and 102 that are occluded by cameras 91 and 96, respectively, in FIG. 9.

Although many of the disclosed embodiments can use occluding thermal cameras successfully, in certain scenarios, such as when using an HMS on a daily basis and/or in a normal day-to-day setting, using thermal cameras that do not occlude their ROIs on the face may provide one or more advantages to the user, to the HMS, and/or to the thermal cameras, which may relate to one or more of the following: esthetics, better ventilation of the face, reduced weight, simplicity to wear, and reduced likelihood to being tarnished.

A "Visible-light camera" refers to a non-contact device designed to detect at least some of the visible spectrum, such as a camera with optical lenses and CMOS or CCD sensor.

The term "inward-facing head-mounted camera" refers to a camera configured to be worn on a user's head and to remain pointed at its ROI, which is on the user's face, also when the user's head makes angular and lateral movements (such as movements with an angular velocity above 0.1 rad/sec, above 0.5 rad/sec, and/or above 1 rad/sec). A head-mounted camera (which may be inward-facing and/or outward-facing) may be physically coupled to a frame worn on the user's head, may be attached to eyeglass using a clip-on mechanism (configured to be attached to and detached from the eyeglasses), or may be mounted to the user's head using any other known device that keeps the camera in a fixed position relative to the user's head also when the head moves. Sentences in the form of "camera physically coupled to the frame" mean that the camera moves with the frame, such as when the camera is fixed to (or integrated into) the frame, or when the camera is fixed to (or integrated into) an element that is physically coupled to the frame. The abbreviation "CAM" denotes "inward-facing head-mounted thermal camera", the abbreviation "$CAM_{out}$" denotes "outward-facing head-mounted thermal camera", the abbreviation "VCAM" denotes "inward-facing head-mounted visible-light camera", and the abbreviation "VCAM$_{out}$" denotes "outward-facing head-mounted visible-light camera".

Sentences in the form of "a frame configured to be worn on a user's head" or "a frame worn on a user's head" refer to a mechanical structure that loads more than 50% of its weight on the user's head. For example, an eyeglasses frame may include two temples connected to two rims connected by a bridge; the frame in Oculus Rift™ includes the foam placed on the user's face and the straps; and the frames in Google Glass™ and Spectacles by Snap Inc. are similar to eyeglasses frames. Additionally or alternatively, the frame may connect to, be affixed within, and/or be integrated with, a helmet (e.g., sports, motorcycle, bicycle, and/or combat helmets) and/or a brainwave-measuring headset.

When a thermal camera is inward-facing and head-mounted, challenges faced by systems known in the art that are used to acquire thermal measurements, which include non-head-mounted thermal cameras, may be simplified and even eliminated with some of the embodiments described herein. Some of these challenges may involve dealing with complications caused by movements of the user, image registration, ROI alignment, tracking based on hot spots or markers, and motion compensation in the IR domain.

In various embodiments, cameras are located close to a user's face, such as at most 2 cm, 5 cm, 10 cm, 15 cm, or 20 cm from the face (herein "cm" denotes to centimeters). The distance from the face/head in sentences such as "a camera located less than 15 cm from the face/head" refers to the shortest possible distance between the camera and the face/head. The head-mounted cameras used in various embodiments may be lightweight, such that each camera weighs below 10 g, 5 g, 1 g, and/or 0.5 g (herein "g" denotes to grams).

Figure 1B:
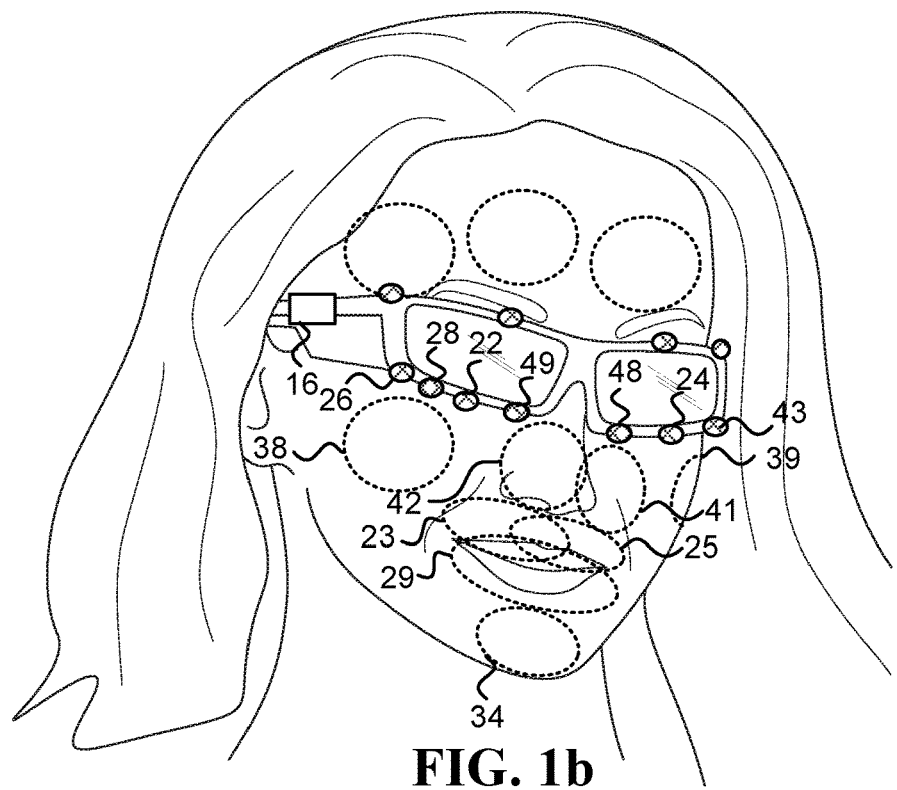

The following figures show various examples of HMSs equipped with head-mounted cameras. FIG. 1a illustrates various inward-facing head-mounted cameras coupled to an eyeglasses frame 15. Cameras 10 and 12 measure regions 11 and 13 on the forehead, respectively. Cameras 18 and 36 measure regions on the periorbital areas 19 and 37, respectively. The HMS further includes an optional computer 16, which may include a processor, memory, a battery and/or a communication module. FIG. 1b illustrates a similar HMS in which inward-facing head-mounted cameras 48 and 49 measure regions 41 and 41, respectively. Cameras 22 and 24 measure regions 23 and 25, respectively. Camera 28 measures region 29. And cameras 26 and 43 measure regions 38 and 39, respectively.

Figure 2:
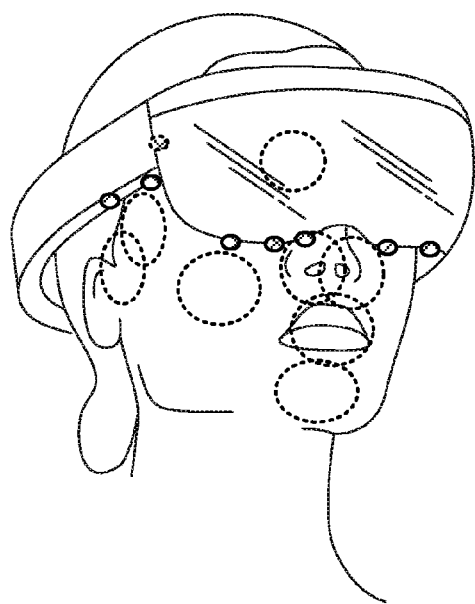
FIG. 2 illustrates inward-facing head-mounted cameras coupled to an augmented reality device.
Figure 3:
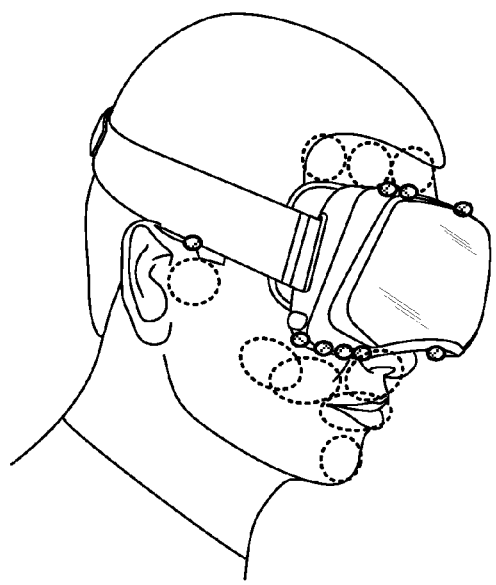
FIG. 3 illustrates head-mounted cameras coupled to a virtual reality device.
Figure 4:
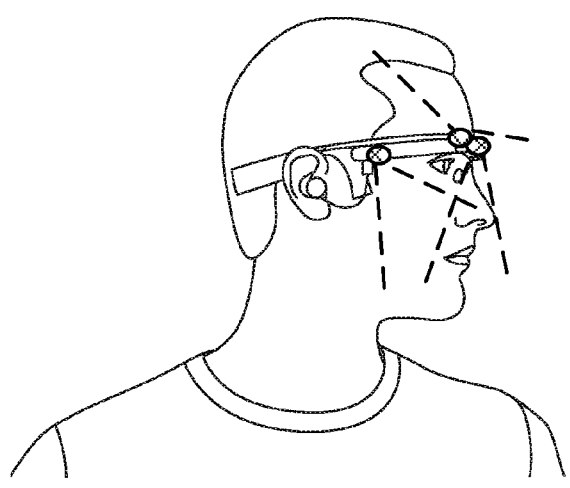
FIG. 4 illustrates a side view of head-mounted cameras coupled to an augmented reality device.
Figure 5:
FIG. 5 illustrates a side view of head-mounted cameras coupled to a sunglasses frame.

FIG. 2 illustrates inward-facing head-mounted cameras coupled to an augmented reality device such as Microsoft HoloLens™. FIG. 3 illustrates head-mounted cameras coupled to a virtual reality device such as Facebook's Oculus Rift™. FIG. 4 is a side view illustration of head-mounted cameras coupled to an augmented reality device such as Google Glass™. FIG. 5 is another side view illustration of head-mounted cameras coupled to a sunglasses frame.

FIG. 6 to FIG. 9 illustrate HMSs configured to measure various ROIs relevant to some of the embodiments describes herein. FIG. 6 illustrates a frame 35 that mounts inward-facing head-mounted cameras 30 and 31 that measure regions 32 and 33 on the forehead, respectively. FIG. 7 illustrates a frame 75 that mounts inward-facing head-mounted cameras 70 and 71 that measure regions 72 and 73 on the forehead, respectively, and inward-facing head-mounted cameras 76 and 77 that measure regions 78 and 79 on the upper lip, respectively. FIG. 8 illustrates a frame 84 that mounts inward-facing head-mounted cameras 80 and 81 that measure regions 82 and 83 on the sides of the nose, respectively. And FIG. 9 illustrates a frame 90 that includes (i) inward-facing head-mounted cameras 91 and 92 that are mounted to protruding arms and measure regions 97 and 98 on the forehead, respectively, (ii) inward-facing head-mounted cameras 95 and 96, which are also mounted to protruding arms, which measure regions 101 and 102 on the lower part of the face, respectively, and (iii) head-mounted cameras 93 and 94 that measure regions on the periorbital areas 99 and 100, respectively.

Figure 10:
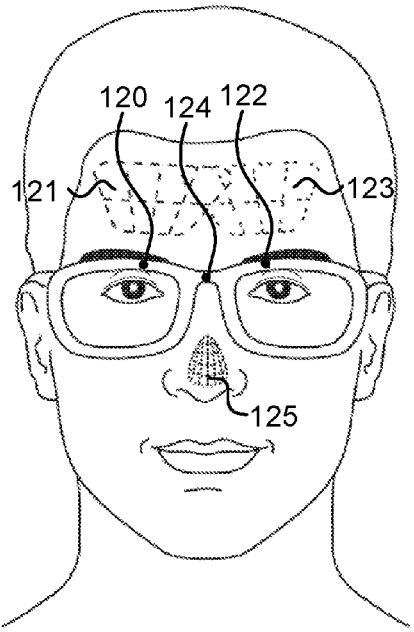
FIG. 10, FIG. 11, FIG. 12 and FIG. 13 illustrate various embodiments of systems that include inward-facing head-mounted cameras having multi-pixel sensors (FPA sensors)
Figure 11:
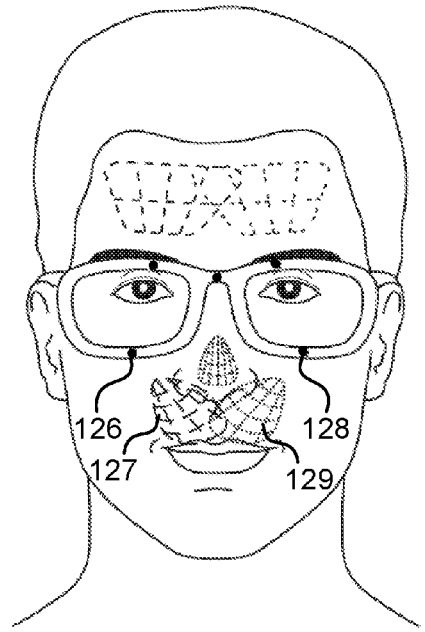
Figure 12:
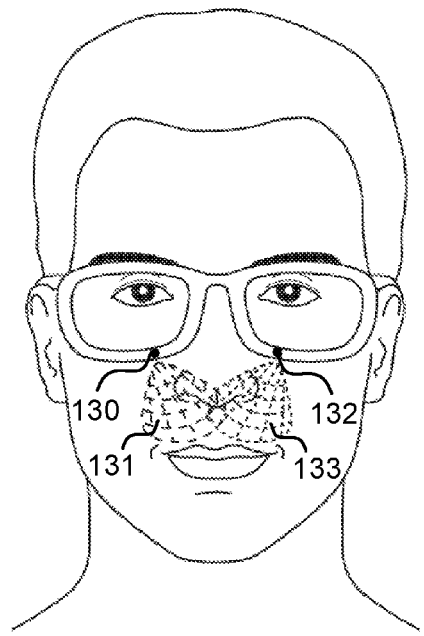
Figure 13:
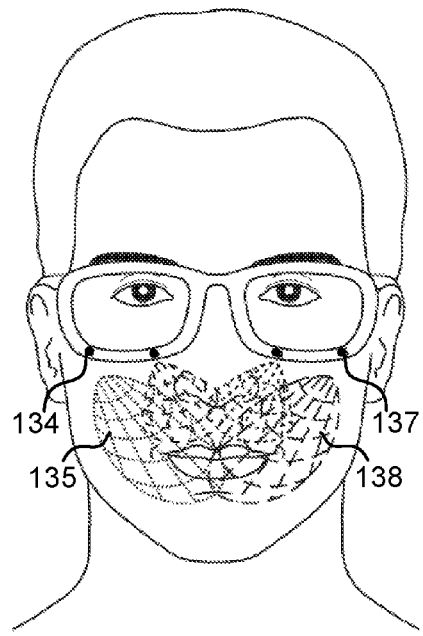

FIG. 10 to FIG. 13 illustrate various inward-facing head-mounted cameras having multi-pixel sensors (FPA sensors), configured to measure various ROIs relevant to some of the embodiments describes herein. FIG. 10 illustrates head-mounted cameras 120 and 122 that measure regions 121 and 123 on the forehead, respectively, and mounts head-mounted camera 124 that measure region 125 on the nose. FIG. 11 illustrates head-mounted cameras 126 and 128 that measure regions 127 and 129 on the upper lip, respectively, in addition to the head-mounted cameras already described in FIG. 10. FIG. 12 illustrates head-mounted cameras 130 and 132 that measure larger regions 131 and 133 on the upper lip and the sides of the nose, respectively. And FIG. 13 illustrates head-mounted cameras 134 and 137 that measure regions 135 and 138 on the right and left cheeks and right and left sides of the mouth, respectively, in addition to the head-mounted cameras already described in FIG. 12.

Figure 18:
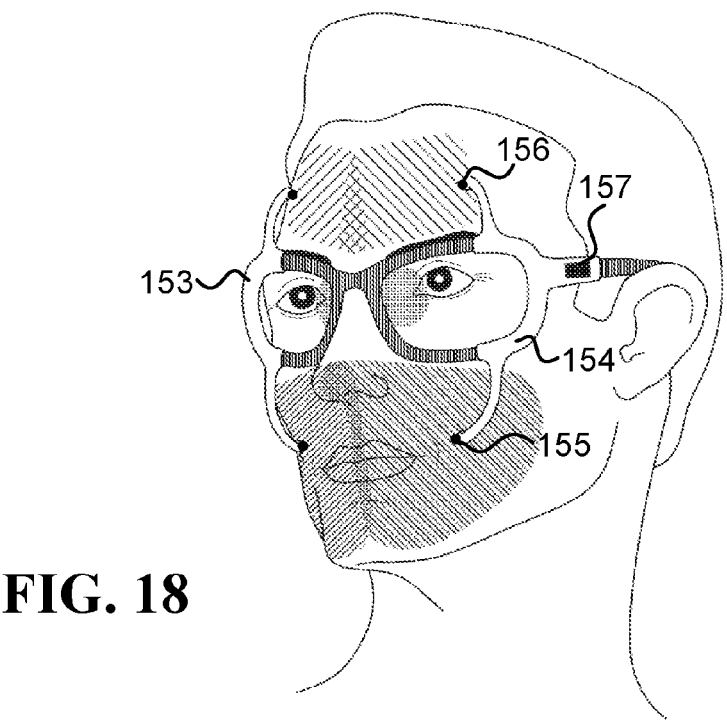
FIG. 18 illustrates embodiments of right and left clip-on devices, which are configured to be attached/detached from an eyeglasses frame, and have protruding arms to hold inward-facing head-mounted cameras.

In some embodiments, the head-mounted cameras may be physically coupled to the frame using a clip-on device configured to be attached/detached from a pair of eyeglasses in order to secure/release the device to/from the eyeglasses, multiple times. The clip-on device holds at least an inward-facing camera, a processor, a battery, and a wireless communication module. Most of the clip-on device may be located in front of the frame (as illustrated in FIG. 14b, FIG. 15b, and FIG. 18), or alternatively, most of the clip-on device may be located behind the frame, as illustrated in FIG. 16b and FIG. 17b.

FIG. 14a, FIG. 14b, and FIG. 14c illustrate two right and left clip-on devices 141 and 142, respectively, configured to attached/detached from an eyeglasses frame 140. The clip-on device 142 includes an inward-facing head-mounted camera 143 pointed at a region on the lower part of the face (such as the upper lip, mouth, nose, and/or cheek), an inward-facing head-mounted camera 144 pointed at the forehead, and other electronics 145 (such as a processor, a battery, and/or a wireless communication module). The clip-on devices 141 and 142 may include additional cameras illustrated in the drawings as black circles.

FIG. 15a and FIG. 15b illustrate a clip-on device 147 that includes an inward-facing head-mounted camera 148 pointed at a region on the lower part of the face (such as the nose), and an inward-facing head-mounted camera 149 pointed at the forehead. The other electronics (such as a processor, a battery, and/or a wireless communication module) is located inside the box 150, which also holds the cameras 148 and 149.

FIG. 16a and FIG. 16b illustrate two right and left clip-on devices 160 and 161, respectively, configured to be attached behind an eyeglasses frame 165. The clip-on device 160 includes an inward-facing head-mounted camera 162 pointed at a region on the lower part of the face (such as the upper lip, mouth, nose, and/or cheek), an inward-facing head-mounted camera 163 pointed at the forehead, and other electronics 164 (such as a processor, a battery, and/or a wireless communication module). The clip-on devices 160 and 161 may include additional cameras illustrated in the drawings as black circles.

FIG. 17a and FIG. 17b illustrate a single-unit clip-on device 170, configured to be attached behind an eyeglasses frame 176. The single-unit clip-on device 170 includes inward-facing head-mounted cameras 171 and 172 pointed at regions on the lower part of the face (such as the upper lip, mouth, nose, and/or cheek), inward-facing head-mounted cameras 173 and 174 pointed at the forehead, a spring 175 configured to apply force that holds the clip-on device 170 to the frame 176, and other electronics 177 (such as a processor, a battery, and/or a wireless communication module). The clip-on device 170 may include additional cameras illustrated in the drawings as black circles.

FIG. 18 illustrates two right and left clip-on devices 153 and 154, respectively, configured to attached/detached from an eyeglasses frame, and having protruding arms to hold the inward-facing head-mounted cameras. Head-mounted camera 155 measures a region on the lower part of the face, head-mounted camera 156 measures regions on the forehead, and the left clip-on device 154 further includes other electronics 157 (such as a processor, a battery, and/or a wireless communication module). The clip-on devices 153 and 154 may include additional cameras illustrated in the drawings as black circles.

It is noted that the elliptic and other shapes of the ROIs in some of the drawings are just for illustration purposes, and the actual shapes of the ROIs are usually not as illustrated. It is possible to calculate the accurate shape of an ROI using various methods, such as a computerized simulation using a 3D model of the face and a model of a head-mounted system (HMS) to which a thermal camera is physically coupled, or by placing a LED instead of the sensor (while maintaining the same field of view) and observing the illumination pattern on the face. Furthermore, illustrations and discussions of a camera represent one or more cameras, where each camera may have the same FOV and/or different FOVs. Unless indicated to the contrary, the cameras may include one or more sensing elements (pixels), even when multiple sensing elements do not explicitly appear in the figures; when a camera includes multiple sensing elements then the illustrated ROI usually refers to the total ROI captured by the camera, which is made of multiple regions that are respectively captured by the different sensing elements. The positions of the cameras in the figures are just for illustration, and the cameras may be placed at other positions on the HMS.

Sentences in the form of an "ROI on an area", such as ROI on the forehead or an ROI on the nose, refer to at least a portion of the area. Depending on the context, and especially when using a CAM having just one pixel or a small number of pixels, the ROI may cover another area (in addition to the area). For example, a sentence in the form of "an ROI on the nose" may refer to either: 100% of the ROI is on the nose, or some of the ROI is on the nose and some of the ROI is on the upper lip.

Various embodiments described herein involve detections of physiological responses based on user measurements. Some examples of physiological responses include stress, an allergic reaction, an asthma attack, a stroke, dehydration, intoxication, or a headache (which includes a migraine). Other examples of physiological responses include manifestations of fear, startle, sexual arousal, anxiety, joy, pain or guilt. Still other examples of physiological responses include physiological signals such as a heart rate or a value of a respiratory parameter of the user. Optionally, detecting a physiological response may involve one or more of the following: determining whether the user has/had the physiological response, identifying an imminent attack associated with the physiological response, and/or calculating the extent of the physiological response.

In some embodiments, detection of the physiological response is done by processing thermal measurements that fall within a certain window of time that characterizes the physiological response. For example, depending on the physiological response, the window may be five seconds long, thirty seconds long, two minutes long, five minutes long, fifteen minutes long, or one hour long. Detecting the physiological response may involve analysis of thermal measurements taken during multiple of the above-described windows, such as measurements taken during different days. In some embodiments, a computer may receive a stream of thermal measurements, taken while the user wears an HMS with coupled thermal cameras during the day, and periodically evaluate measurements that fall within a sliding window of a certain size.

In some embodiments, models are generated based on measurements taken over long periods. Sentences of the form of "measurements taken during different days" or "measurements taken over more than a week" are not limited to continuous measurements spanning the different days or over the week, respectively. For example, "measurements taken over more than a week" may be taken by eyeglasses equipped with thermal cameras, which are worn for more than a week, 8 hours a day. In this example, the user is not required to wear the eyeglasses while sleeping in order to take measurements over more than a week. Similarly, sentences of the form of "measurements taken over more than 5 days, at least 2 hours a day" refer to a set comprising at least 10 measurements taken over 5 different days, where at least two measurements are taken each day at times separated by at least two hours.

Utilizing measurements taken of a long period (e.g., measurements taken on "different days") may have an advantage, in some embodiments, of contributing to the generalizability of a trained model. Measurements taken over the long period likely include measurements taken in different environments and/or measurements taken while the measured user was in various physiological and/or mental states (e.g., before/after meals and/or while the measured user was sleepy/energetic/happy/depressed, etc.). Training a model on such data can improve the performance of systems that utilize the model in the diverse settings often encountered in real-world use (as opposed to controlled laboratory-like settings). Additionally, taking the measurements over the long period may have the advantage of enabling collection of a large amount of training data that is required for some machine learning approaches (e.g., "deep learning").

Detecting the physiological response may involve performing various types of calculations by a computer. Optionally, detecting the physiological response may involve performing one or more of the following operations: comparing thermal measurements to a threshold (when the threshold is reached that may be indicative of an occurrence of the physiological response), comparing thermal measurements to a reference time series, and/or by performing calculations that involve a model trained using machine learning methods. Optionally, the thermal measurements upon which the one or more operations are performed are taken during a window of time of a certain length, which may optionally depend on the type of physiological response being detected. In one example, the window may be shorter than one or more of the following durations: five seconds, fifteen seconds, one minute, five minutes, thirty minute, one hour, four hours, one day, or one week. In another example, the window may be longer than one or more of the aforementioned durations. Thus, when measurements are taken over a long period, such as measurements taken over a period of more than a week, detection of the physiological response at a certain time may be done based on a subset of the measurements that falls within a certain window near the certain time; the detection at the certain time does not necessarily involve utilizing all values collected throughout the long period.

In some embodiments, detecting the physiological response of a user may involve utilizing baseline thermal measurement values, most of which were taken when the user was not experiencing the physiological response. Optionally, detecting the physiological response may rely on observing a change to typical temperatures at one or more ROIs (the baseline), where different users might have different typical temperatures at the ROIs (i.e., different baselines). Optionally, detecting the physiological response may rely on observing a change to a baseline level, which is determined based on previous measurements taken during the preceding minutes and/or hours.

In some embodiments, detecting a physiological response involves determining the extent of the physiological response, which may be expressed in various ways that are indicative of the extent of the physiological response, such as: (i) a binary value indicative of whether the user experienced, and/or is experiencing, the physiological response, (ii) a numerical value indicative of the magnitude of the physiological response, (iii) a categorial value indicative of the severity/extent of the physiological response, (iv) an expected change in thermal measurements of an ROI (denoted $TH_{ROI}$ or some variation thereof), and/or (v) rate of change in $TH_{ROI}$. Optionally, when the physiological response corresponds to a physiological signal (e.g., a heart rate, a breathing rate, and an extent of frontal lobe brain activity), the extent of the physiological response may be interpreted as the value of the physiological signal.

One approach for detecting a physiological response, which may be utilized in some embodiments, involves comparing thermal measurements of one or more ROIs to a threshold. In these embodiments, the computer may detect the physiological response by comparing the thermal measurements, and/or values derived therefrom (e.g., a statistic of the measurements and/or a function of the measurements), to the threshold to determine whether it is reached. Optionally, the threshold may include a threshold in the time domain, a threshold in the frequency domain, an upper threshold, and/or a lower threshold. When a threshold involves a certain change to temperature, the certain change may be positive (increase in temperature) or negative (decrease in temperature). Different physiological responses described herein may involve different types of thresholds, which may be an upper threshold (where reaching the threshold means≥the threshold) or a lower threshold (where reaching the threshold means≤the threshold); for example, each physiological response may involve at least a certain degree of heating, or at least a certain degree cooling, at a certain ROI on the face.

Another approach for detecting a physiological response, which may be utilized in some embodiments, may be applicable when the thermal measurements of a user are treated as time series data. For example, the thermal measurements may include data indicative of temperatures at one or more ROIs at different points of time during a certain period. In some embodiments, the computer may compare thermal measurements (represented as a time series) to one or more reference time series that correspond to periods of time in which the physiological response occurred. Additionally or alternatively, the computer may compare the thermal measurements to other reference time series corresponding to times in which the physiological response did not occur. Optionally, if the similarity between the thermal measurements and a reference time series corresponding to a physiological response reaches a threshold, this is indicative of the fact that the thermal measurements correspond to a period of time during which the user had the physiological response. Optionally, if the similarity between the thermal measurements and a reference time series that does not correspond to a physiological response reaches another threshold, this is indicative of the fact that the thermal measurements correspond to a period of time in which the user did not have the physiological response. Time series analysis may involve various forms of processing involving segmenting data, aligning data, clustering, time warping, and various functions for determining similarity between sequences of time series data. Some of the techniques that may be utilized in various embodiments are described in Ding, Hui, et al. "Querying and mining of time series data: experimental comparison of representations and distance measures." Proceedings of the VLDB Endowment 1.2 (2008): 1542-1552, and in Wang, Xiaoyue, et al. "Experimental comparison of representation methods and distance measures for time series data." Data Mining and Knowledge Discovery 26.2 (2013): 275-309.

Herein, "machine learning" methods refers to learning from examples using one or more approaches. Optionally, the approaches may be considered supervised, semi-supervised, and/or unsupervised methods. Examples of machine learning approaches include: decision tree learning, association rule learning, regression models, nearest neighbors classifiers, artificial neural networks, deep learning, inductive logic programming, support vector machines, clustering, Bayesian networks, reinforcement learning, representation learning, similarity and metric learning, sparse dictionary learning, genetic algorithms, rule-based machine learning, and/or learning classifier systems.

Herein, a "machine learning-based model" is a model trained using machine learning methods. For brevity's sake, at times, a "machine learning-based model" may simply be called a "model". Referring to a model as being "machine learning-based" is intended to indicate that the model is trained using machine learning methods (otherwise, "model" may also refer to a model generated by methods other than machine learning).

In some embodiments, which involve utilizing a machine learning-based model, a computer is configured to detect the physiological response by generating feature values based on the thermal measurements (and possibly other values), and/or based on values derived therefrom (e.g., statistics of the measurements). The computer then utilizes the machine learning-based model to calculate, based on the feature values, a value that is indicative of whether, and/or to what extent, the user is experiencing (and/or is about to experience) the physiological response. Optionally, calculating said value is considered "detecting the physiological response". Optionally, the value calculated by the computer is indicative of the probability that the user has/had the physiological response.

Herein, feature values may be considered input to a computer that utilizes a model to perform the calculation of a value, such as the value indicative of the extent of the physiological response mentioned above. It is to be noted that the terms "feature" and "feature value" may be used interchangeably when the context of their use is clear. However, a "feature" typically refers to a certain type of value, and represents a property, while "feature value" is the value of the property with a certain instance (sample). For example, a feature may be temperature at a certain ROI, while the feature value corresponding to that feature may be 36.9° C. in one instance and 37.3° C. in another instance.

In some embodiments, a machine learning-based model used to detect a physiological response is trained based on data that includes samples. Each sample includes feature values and a label. The feature values may include various types of values. At least some of the feature values of a sample are generated based on measurements of a user taken during a certain period of time (e.g., thermal measurements taken during the certain period of time). Optionally, some of the feature values may be based on various other sources of information described herein. The label is indicative of a physiological response of the user corresponding to the certain period of time. Optionally, the label may be indicative of whether the physiological response occurred during the certain period and/or the extent of the physiological response during the certain period. Additionally or alternatively, the label may be indicative of how long the physiological response lasted. Labels of samples may be generated using various approaches, such as self-report by users, annotation by experts that analyze the training data, automatic annotation by a computer that analyzes the training data and/or analyzes additional data related to the training data, and/or utilizing additional sensors that provide data useful for generating the labels. It is to be noted that herein when it is stated that a model is trained based on certain measurements (e.g., "a model trained based on $TH_{ROI}$ taken on different days"), it means that the model was trained on samples comprising feature values generated based on the certain measurements and labels corresponding to the certain measurements. Optionally, a label corresponding to a measurement is indicative of the physiological response at the time the measurement was taken.

Various types of feature values may be generated based on thermal measurements. In one example, some feature values are indicative of temperatures at certain ROIs. In another example, other feature values may represent a temperature change at certain ROIs. The temperature changes may be with respect to a certain time and/or with respect to a different ROI. In order to better detect physiological responses that take some time to manifest, in some embodiments, some feature values may describe temperatures (or temperature changes) at a certain ROI at different points of time. Optionally, these feature values may include various functions and/or statistics of the thermal measurements such as minimum/maximum measurement values and/or average values during certain windows of time.

It is to be noted that when it is stated that feature values are generated based on data comprising multiple sources, it means that for each source, there is at least one feature value that is generated based on that source (and possibly other data). For example, stating that feature values are generated from thermal measurements of first and second ROIs ($TH_{ROI1}$ and $TH_{ROI2}$, respectively) means that the feature values may include a first feature value generated based on $TH_{ROI1}$ and a second feature value generated based on $TH_{ROI2}$. Optionally, a sample is considered generated based on measurements of a user (e.g., measurements comprising $TH_{ROI1}$ and $TH_{ROI2}$) when it includes feature values generated based on the measurements of the user.

In addition to feature values that are generated based on thermal measurements, in some embodiments, at least some feature values utilized by a computer (e.g., to detect a physiological response or train a mode) may be generated based on additional sources of data that may affect temperatures measured at various facial ROIs. Some examples of the additional sources include: (i) measurements of the environment such as temperature, humidity level, noise level, elevation, air quality, a wind speed, precipitation, and infrared radiation; (ii) contextual information such as the time of day (e.g., to account for effects of the circadian rhythm), day of month (e.g., to account for effects of the lunar rhythm), day in the year (e.g., to account for seasonal effects), and/or stage in a menstrual cycle; (iii) information about the user being measured such as sex, age, weight, height, and/or body build. Alternatively or additionally, at least some feature values may be generated based on physiological signals of the user obtained by sensors that are not thermal cameras, such as a visible-light camera, a photoplethysmogram (PPG) sensor, an electrocardiogram (ECG) sensor, an electroencephalography (EEG) sensor, a galvanic skin response (GSR) sensor, or a thermistor.

The machine learning-based model used to detect a physiological response may be trained, in some embodiments, based on data collected in day-to-day, real world scenarios. As such, the data may be collected at different times of the day, while users perform various activities, and in various environmental conditions. Utilizing such diverse training data may enable a trained model to be more resilient to the various effects different conditions can have on the values of thermal measurements, and consequently, be able to achieve better detection of the physiological response in real world day-to-day scenarios.

Since real world day-to-day conditions are not the same all the time, sometimes detection of the physiological response may be hampered by what is referred to herein as "confounding factors". A confounding factor can be a cause of warming and/or cooling of certain regions of the face, which is unrelated to a physiological response being detected, and as such, may reduce the accuracy of the detection of the physiological response. Some examples of confounding factors include: (i) environmental phenomena such as direct sunlight, air conditioning, and/or wind; (ii) things that are on the user's face, which are not typically there and/or do not characterize the faces of most users (e.g., cosmetics, ointments, sweat, hair, facial hair, skin blemishes, acne, inflammation, piercings, body paint, and food leftovers); (iii) physical activity that may affect the user's heart rate, blood circulation, and/or blood distribution (e.g., walking, running, jumping, and/or bending over); (iv) consumption of substances to which the body has a physiological response that may involve changes to temperatures at various facial ROIs, such as various medications, alcohol, caffeine, tobacco, and/or certain types of food; and/or (v) disruptive facial movements (e.g., frowning, talking, eating, drinking, sneezing, and coughing).

Occurrences of confounding factors may not always be easily identified in thermal measurements. Thus, in some embodiments, systems may incorporate measures designed to accommodate for the confounding factors. In some embodiments, these measures may involve generating feature values that are based on additional sensors, other than the thermal cameras. In some embodiments, these measures may involve refraining from detecting the physiological response, which should be interpreted as refraining from providing an indication that the user has the physiological response. For example, if an occurrence of a certain confounding factor is identified, such as strong directional sunlight that heats one side of the face, the system may refrain from detecting that the user had a stroke. In this example, the user may not be alerted even though a temperature difference between symmetric ROIs on both sides of the face reaches a threshold that, under other circumstances, would warrant alerting the user.

Training data used to train a model for detecting a physiological response may include, in some embodiments, a diverse set of samples corresponding to various conditions, some of which involve occurrence of confounding factors (when there is no physiological response and/or when there is a physiological response). Having samples in which a confounding factor occurs (e.g., the user is in direct sunlight or touches the face) can lead to a model that is less susceptible to wrongfully detect the physiological response (which may be considered an occurrence of a false positive) in real world situations.

When a model is trained with training data comprising samples generated from measurements of multiple users, the model may be considered a general model. When a model is trained with training data comprising at least a certain proportion of samples generated from measurements of a certain user, and/or when the samples generated from the measurements of the certain user are associated with at least a certain proportion of weight in the training data, the model may be considered a personalized model for the certain user. Optionally, the personalized model for the certain user provides better results for the certain user, compared to a general model that was not personalized for the certain user. Optionally, personalized model may be trained based on measurements of the certain user, which were taken while the certain user was in different situations; for example, train the model based on measurements taken while the certain user had a headache/epilepsy/stress/anger attack, and while the certain user did not have said attack. Additionally or alternatively, the personalized model may be trained based on measurements of the certain user, which were taken over a duration long enough to span different situations; examples of such long enough durations may include: a week, a month, six months, a year, and three years.

Training a model that is personalized for a certain user may require collecting a sufficient number of training samples that are generated based on measurements of the certain user. Thus, initially detecting the physiological response with the certain user may be done utilizing a general model, which may be replaced by a personalized model for the certain user, as a sufficiently large number of samples are generated based on measurements of the certain user. Another approach involves gradually modifying a general model based on samples of the certain user in order to obtain the personalized model.

After a model is trained, the model may be provided for use by a system that detects the physiological response. Providing the model may involve performing different operations. In one embodiment, providing the model to the system involves forwarding the model to the system via a computer network and/or a shared computer storage medium (e.g., writing the model to a memory that may be accessed by the system that detects the physiological response). In another embodiment, providing the model to the system involves storing the model in a location from which the system can retrieve the model, such as a database and/or cloud-based storage from which the system may retrieve the model. In still another embodiment, providing the model involves notifying the system regarding the existence of the model and/or regarding an update to the model. Optionally, this notification includes information needed in order for the system to obtain the model.

A model for detecting a physiological response may include different types of parameters. Following are some examples of various possibilities for the model and the type of calculations that may be accordingly performed by a computer in order to detect the physiological response: (a) the model comprises parameters of a decision tree. Optionally, the computer simulates a traversal along a path in the decision tree, determining which branches to take based on the feature values. A value indicative of the physiological response may be obtained at the leaf node and/or based on calculations involving values on nodes and/or edges along the path; (b) the model comprises parameters of a regression model (e.g., regression coefficients in a linear regression model or a logistic regression model). Optionally, the computer multiplies the feature values (which may be considered a regressor) with the parameters of the regression model in order to obtain the value indicative of the physiological response; and/or (c) the model comprises parameters of a neural network. For example, the parameters may include values defining at least the following: (i) an interconnection pattern between different layers of neurons, (ii) weights of the interconnections, and (iii) activation functions that convert each neuron's weighted input to its output activation. Optionally, the computer provides the feature values as inputs to the neural network, computes the values of the various activation functions and propagates values between layers, and obtains an output from the network, which is the value indicative of the physiological response.

A user interface (UI) may be utilized, in some embodiments, to notify the user and/or some other entity, such as a caregiver, about the physiological response and/or present an alert responsive to an indication that the extent of the physiological response reaches a threshold. The UI may include a screen to display the notification and/or alert, a speaker to play an audio notification, a tactile UI, and/or a vibrating UI. In some embodiments, "alerting" about a physiological response of a user refers to informing about one or more of the following: the occurrence of a physiological response that the user does not usually have (e.g., a stroke, intoxication, and/or dehydration), an imminent physiological response (e.g., an allergic reaction, an epilepsy attack, and/or a migraine), and an extent of the physiological response reaching a threshold (e.g., stress and/or anger reaching a predetermined level).

One application for which thermal measurements of the face may be useful is to detect an allergic reaction. In one embodiment, a system configured to detect an allergic reaction of a user includes at least a CAM that takes thermal measurements of a region on the nose ($TH_N$) of the user, and a computer that detects an allergic reaction of the user based on $TH_N$. Optionally, an allergen may be any substance that causes the user to experience an allergic reaction due to the exposure of the user to the allergen (e.g., by consuming, inhaling, and/or coming into physical contact with the allergen). For example, an allergic reaction may be a reaction to a drug, peanuts, eggs, wheat, dairy products, seafood, pollen, dust, and/or perfume.

In one embodiment, CAM is physically coupled to a frame worn on the user's head (e.g., a frame of glasses or an augmented reality display). Optionally, CAM is located less than 15 cm from the user's face. Optionally, CAM weighs less than 10 g, 5 g or 1 g. Optionally, CAM uses a thermopile, a pyroelectric sensor, or a microbolometer sensor, which may be a focal-plane array sensor. For example, CAM may be the thermal cameras 48 and/or 49, which are illustrated in FIG. 1b, or the thermal camera 540 illustrated in FIG. 25.

Optionally, multiple CAMs may be utilized to obtain measurements of various ROIs such as different regions/sides of the nose, mouth and/or cheeks. For example, allergic reaction may cause red eyes, itchy eyes, tearing eyes, swollen eyelids, and/or burning eyes/eyelids. In some cases, a thermal camera that captures a region on the periorbital ($TH_{peri}$) around at least one of the eyes may detect an eye allergy symptom before the user is aware of the allergic reaction and/or used to assess the extent of the allergic reaction. As another example, allergic reaction may cause hives (urticaria) around the mouth and/or other parts of the face. In some cases, a thermal camera that captures the area around the mouth ($TH_{lips}$) may detect the hives around the mouth before the user is aware of the allergic reaction and/or used to assess the extent of the allergic reaction. In still some cases, thermal measurements of regions on the right and/or left cheeks ($TH_{ch}$) may help detecting the allergic reaction.

The computer is configured, in one embodiment, to detect the allergic reaction based on $TH_N$ and optionally other data, such as $TH_{CH}$, $TH_{peri}$, and/or $TH_{lips}$ mentioned above and/or other sources of information mentioned below. In one embodiment, detecting the allergic reaction may involve one or more of the following: determining whether the user is experiencing an allergic reaction, and/or determining the extent of the allergic reaction. Optionally, the extent of the allergic reaction may be indicative of the severity of the allergic reaction, and/or the duration of the allergic reaction (e.g., total time of the allergic reaction and/or the time remaining until the allergic reaction subsides).

In some cases, changes to temperatures at regions of the face (e.g., in the nasal area) occur quickly at the initial stages of an allergic reaction. Thus, the computer may detect the allergic reaction at its initial stages even before the user is aware of the allergic reaction. Thus, in some embodiments, detecting the allergic reaction involves detecting an onset of the allergic reaction, which may involve determining the time until the reaction reaches its peak severity (e.g., a rash, coughing, respiratory distress, sneezing) and/or determining the expected degree of severity (extent) of the allergic reaction.

In some cases, at the time the allergic reaction is identified, a user having the allergic reaction may not be aware of the allergic reaction, e.g., because the symptoms are not strong enough at the time. Thus, being notified about an allergic reaction before its full manifestation may have an advantage, in some embodiments, of allowing the user to take early action to alleviate and/or decrease the symptoms (e.g., take antihistamines) or seek medical attention.

In some allergic reactions, the nasal temperature can rise rapidly within minutes, before other more noticeable symptoms may manifest themselves (e.g., sneezing, itching, and/or respiratory problems). Thus, rising nasal temperatures may serve as an indication of an allergic reaction. For example, a fast increase due to an allergic reaction may correspond to an increase of more than 0.8° C. within a period of less than 10 minutes, or even less than 5 minutes.

FIG. 24a and FIG. 24b illustrate a scenario in which a user is alerted about an expected allergic reaction. In FIG. 24a, the user's nasal temperature is normal. At that time, a cat, to which the user is allergic, walks past the user. FIG. 24b illustrates the situation shortly after. The user's nasal temperature has increased, and based on thermal measurements of the nasal region, a computer issues an alert to the user about the expected allergic reaction. Note that at the time the alert is issued, the user may not be aware of any symptoms of the allergic reaction. Receiving an early warning in this case may enable the user to take measures to alleviate the effects of the allergic reaction, such as taking an antihistamine medicine.

In one embodiment, a system configured to alert about an allergic reaction includes at least CAM (which is discussed above) and a user interface (UI), such as UI 373. CAM is worn on a user's head and takes thermal measurements of a region on the user's nose ($TH_N$). Optionally, CAM weighs below 10 g, is physically coupled to a frame worn on the user's head, and is located less than 15 cm from the user's face. Optionally, the system includes a transmitter that may be used to transmit $TH_N$ to a computer that detects the allergic reaction based on $TH_N$. In one example, the computer may belong to a device of the user, such as a computer of an HMS of which CAM is part, or a computer belonging to a smartphone or a smartwatch carried by the user. In another example, the computer may be remote of the user, such as cloud-based server. Various approaches that may be utilized by the computer to detect the allergic reaction are discussed below. Optionally, responsive to detecting the allergic reaction (e.g., by calculating that an extent of the allergic reaction reaches a threshold), the computer commands the UI to provide the alert. For example, the computer may send a signal to a smartphone app, and/or to a software agent that has control of the UI, to provide the alert. In another example, the computer may send an instruction to the UI to provide the alert. Optionally, the alert is provided as text, image, sound, and/or haptic feedback.

There are various ways the computer may utilize $TH_N$ and possibly other thermal measurements such as $TH_{CH}$, $TH_{peri}$, and/or $TH_{lips}$ in order to detect the allergic reaction. In one embodiment, the computer may compare values derived from $TH_N$ (and/or from $TH_{CH}$, $TH_{peri}$, and/or $TH_{lips}$) to a certain threshold, and determine whether the threshold is reached (which is indicative of an occurrence of the allergic reaction). Optionally, the threshold is determined based on previous thermal measurements of the user. Optionally, the threshold is determined based on previous thermal measurements of other users. In another embodiment, the computer may determine a similarity between a reference time series corresponding to the allergic reaction and $TH_N$ and optionally the other thermal measurements (or a time series derived therefrom). Optionally, when a sufficiently high similarity is detected, the computer may interpret that as an indication of an occurrence of the allergic reaction. The reference time series may be generated based on previous thermal measurements of the user and/or of other users.

In yet another embodiment, the computer may generate feature values based on thermal measurements comprising $TH_N$ and optionally $TH_{CH}$, $TH_{peri}$, and/or $TH_{lips}$, and utilize a machine learning-based model to calculate, based on the feature values, a value indicative of whether the allergic reaction occurred and/or indicative of an extent of the allergic reaction (calculating the value be considered herein as "detecting the allergic reaction"). Optionally, the model was trained based on previous thermal measurements of the user. For example, the previous thermal measurements may include a first set of thermal measurements taken while the user had an allergic reaction, and a second set of thermal measurements taken while the user did not have an allergic reaction. In this example, the model may be considered a personalized model for the user. Additionally or alternatively, the model may be trained on thermal measurements of other users (e.g., a general model). Optionally, different models may be created to detect different types of allergic reactions, to detect allergic reactions to different allergens, and/or to detect different extents of an allergic reaction.

In one example, detection of the allergic reaction may involve the computer performing the following: (i) generating feature values based on thermal measurements comprising $TH_N$ and optionally $TH_{CH}$, $TH_{peri}$, and/or $TH_{lips}$; and (ii) utilizing a model to detect the allergic reaction based on the feature values. Optionally, the model was trained based on previous thermal measurements of the user comprising $TH_N$ and optionally $TH_{CH}$, $TH_{peri}$, and/or $TH_{lips}$, which were taken while the user had an allergic reaction. Alternatively, the model was trained based on a first set of previous thermal measurements of the user comprising $TH_N$ and optionally $TH_{CH}$, $TH_{peri}$, and/or $TH_{lips}$, which were taken while the user had an allergic reaction, and a second set of previous thermal measurements of the user comprising $TH_N$ and optionally $TH_{CH}$, $TH_{peri}$, and/or $TH_{lips}$, which were taken while the user did not have an allergic reaction.

In some embodiments, detecting the allergic reaction may involve utilizing baseline $TH_N$, most of which were taken when the user did not have an allergic reaction. Thus, detecting the allergic reaction may rely on observing a change relative to typical temperatures at the ROIs. In one example, the computer detects the allergic reaction based a difference between $TH_N$ and a baseline value determined based on a set of previous $TH_N$ taken with CAM. In this example, most of $TH_N$ belonging to the set were taken while the user had an allergic reaction, or within thirty minutes before or after the user had an allergic reaction.

Confounding factors such as extensive physical activity, touching the nose, and/or direct sunlight aimed at the nose may lead, in some embodiments, to less accurate detections of an allergic reaction (e.g., by increasing the frequency of false detections of the allergic reaction). In some embodiments, the system may include a sensor that takes additional measurements ($m_{conf}$) of the user, and/or of the environment in which the user was in while $TH_N$ were taken. Optionally, $m_{conf}$ are indicative of an extent to which a confounding factor occurred while $TH_N$ were taken. Another approach that may be utilized by the computer is to generate feature values based on $m_{conf}$ and to utilize these feature values in the detection of the allergic reaction.

Receiving early notice regarding an allergic reaction may be useful in some embodiments, since it may enable a user to take action in order to reduce the severity of the allergic reaction. For example, the user may attempt to reduce exposure to an allergen (e.g., leave an area that has a high concentration of pollen), take certain medication (e.g., antihistamines) to reduce the effects of the allergic reaction, and/or promptly seek medical attention (in anticipation of a more severe allergic reaction that is to come). However, providing such early indications may involve relaxing the conditions under which an allergic reaction is detected (e.g., lowering thresholds for $TH_N$). This can come at a cost of having more false positives in the detection of allergic reactions. Thus, in order to avoid excessive false positives the system may need to be judicious about when it employs more relaxed conditions for detecting an allergic reaction.

One way in which false positive allergic reaction detections may be reduced is to utilize knowledge of conditions and/or times in which it is more likely that the user may experience an allergic reaction. For example, if it is known with high probability that the user was exposed to an allergen to which the user is known, or suspected, to be allergic, then more relaxed conditions for detecting the allergic reaction may be employed. Optionally, if there is no reason to believe that the user was exposed to an allergen, then the more strict conditions may be employed for detecting the allergic reaction.

In some embodiments, the computer receives an indication of whether the user was exposed to an allergen and utilizes the indication in the process of detecting the allergic reactions. This indication may be utilized in various ways, which may depend on how the computer detects allergic reactions, as the following embodiments demonstrate.

In one embodiment, the computer compares $TH_N$ (or certain values computed based on $TH_N$) to a threshold, such that if $TH_N$ reach the threshold, this is indicative of a likely occurrence of the allergic reaction. In this embodiment, the threshold may be selected based on the indication that indicates exposure, or possible exposure, to the allergen. For example, responsive to receiving a first indication indicating that the user was exposed to the allergen, the computer selects a first threshold, and responsive to receiving a second indication indicating that the user was not exposed to the allergen, the computer selects a second threshold that is higher than the first threshold. Thus, the second threshold requires a greater change in $TH_N$ in order to detect the allergic reaction.

In another embodiment, the computer calculates a similarity between $TH_N$ and a reference time series comprising data indicative of temperatures at different points in time during an allergic reaction (e.g., time series of the user having the allergic reaction). When the similarity reaches a certain threshold, this is indicative of an occurrence of the allergic reaction. In this embodiment, the certain threshold may be selected based on the indication that indicates exposure, or possible exposure, to the allergen. For example, responsive to receiving a first indication indicating that the user was exposed to the allergen, the computer selects a first certain threshold, and responsive to receiving a second indication indicating that the user was not exposed to the allergen, the computer selects a second certain threshold that corresponds to a higher extent of similarity than the first certain threshold. Thus, the second certain threshold requires greater similarity to the reference time series in order to detect the allergic reaction.

In yet another embodiment, the computer utilizes $TH_N$ to generate feature values, and to utilize a model to calculate, based on the feature values, an extent of the allergic reaction. In this embodiment, the model is a machine learning-based model that is generated based on previous thermal measurements of regions on the noses of one or more users (which may include the user and/or other users). At least some of the feature values are generated based on the indication, and may describe various properties of the exposure to an allergen, such as the type of allergen, the duration of exposure, the extent of exposure (e.g., dosage), and/or the time that has elapsed since the exposure. Thus, the above factors may be taken into account by the model, which may increase the chances of detecting an allergic reaction when the features indicate sufficient exposure to certain allergens.

The indication that is indicative of exposure to the allergen may be received from various sources. In one embodiment, the indication may be self-reported by the user. For example, the user may provide information about the exposure through interaction with a device such as a smartphone or speaking with a software agent via a microphone. In another embodiment, various camera-based systems may be utilized to take images comprising the allergen or an object associated with the allergen, analyze the images, and generate the indication about the exposure based on the analysis. Such systems that monitor the environment the user is in and/or substances the user consumes are discussed in more detail below. In yet another embodiment, an external source may provide indication based on determining the location of the user. For example, the user's location may be determined based on GPS, cellphone transmissions, and/or Wi-Fi transmissions. Additionally, an external database that includes real-time data about the presence of various allergens (e.g., dust or pollen) may be queried in order to determine whether the user is likely exposed to a potential allergen substance.

Figure 22:
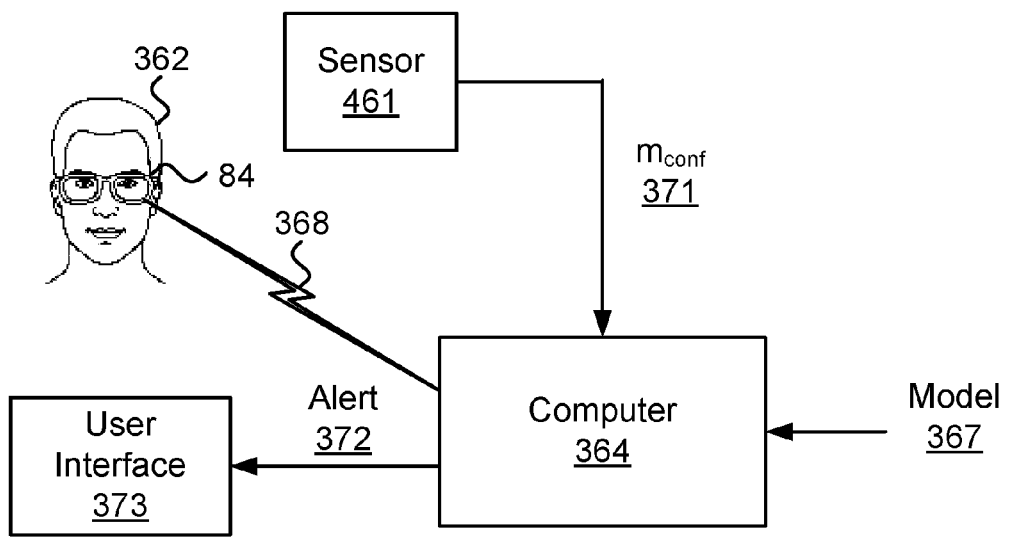
FIG. 22 illustrates an embodiment of a system configured to detect an allergic reaction.

The following method for detecting an allergic reaction of a user may be used, in some embodiments, by systems modeled according to FIG. 22. The steps described below may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform the following steps:

In Step 1, taking thermal measurements of a region on the nose ($TH_N$) of the user using an inward-facing head-mounted thermal camera.

In Step 2, training a model based on previous $TH_N$ taken during different days.

And in Step 3, detecting the allergic reaction based on $TH_N$ and the model. Optionally, the system detects and alerts about the allergic reaction before the user is aware of the symptom of the allergic reaction. Optionally, the alert is provided as text, image, sound, and/or haptic feedback. Optionally, detecting the allergic reaction involves generating feature values based on a subset of $TH_N$ comprising $TH_N$ taken during a window of a certain length, and utilizing a model to calculate, based on the feature values, a value indicative of the extent of allergic reaction. Optionally, the model may be personalized for the user. For example, the model was trained based on previous $TH_N$ of the user, taken during different days, which include: a first set of measurements taken while the user had an allergic reaction, and a second set of measurements taken while the user did not have an allergic reaction. Optionally, the model may be based on measurements of multiple users, taken during different days, which include: a first set of measurements taken while the users had an allergic reaction, and a second set of measurements taken while the users did not have an allergic reaction. The step of generating feature values and utilizing the model may be performed multiple times throughout the period of different days during which $TH_N$ were taken, each time utilizing a subset of $TH_N$ taken during a different window of a certain length; the alerting is done at a certain time for which an allergic reaction of at least a certain extent is detected (which warrants an alert).

Some of the embodiments described herein may be utilized to identify potential causes for the change (e.g., rise) of the temperature at an ROI. These causes may include inhaled allergens, food, drugs, and/or various chemicals which the user might have been exposed to (e.g., via ingestion, inhalation, and/or physical contact). In one embodiment, the computer may identify a potential allergen substance by estimating a time of exposure to the allergen from data indicative of a deviation over time of mean nasal temperature from a baseline and identifying the substances consumed by the user, and/or to which the user was exposed, around that time. For example, by identifying based on $TH_N$ when the nasal temperature started to rise, and taking into account the time required for the allergic reaction to be manifested via a temperature rise, a window of time can be determined during which the user was likely exposed to the allergen. Examining which substances the user was exposed to during the window can yield a list of one or more potential allergen substances. Optionally, the system alerts the user about the one or more potential allergen substances. Optionally, the system stores in a database potential allergen substances identified based on data indicative of a deviation over time of mean nasal temperature from baseline (such as allergens identified based on deviation over time of mean nasal temperature from baseline). In some embodiments, the system includes a camera that captures images of substances consumed by the user. Optionally, the camera is mounted to a frame worn on the user's head. Optionally, the system displays to the user an image of a substance associated with the potential allergen substance.

There are various known systems that may be utilized to monitor what substances a user was exposed to and/or what substances a user consumed. For example, systems that may be utilized to determine what the user ate or drank are described in US patent application 20110318717 (Personalized Food Identification and Nutrition Guidance System), in U.S. Pat. No. 9,053,483 (Personal audio/visual system providing allergy awareness), and in U.S. Pat. No. 9,189,021 (Wearable food nutrition feedback system). Additionally, obtaining indications of possible allergens to which the user was exposed is described in U.S. Pat. No. 9,000,933 (Automated allergy alerts). In one embodiment, upon identifying an increase in nasal temperature, the system can identify the potential cause to be one of the substances to which the user was exposed during a predetermined preceding duration, such as the preceding 20 min, 10 min, or 5 min.

FIG. 25 illustrates how the system may be utilized to identify a trigger of an allergic reaction. CAM 540 is coupled to a frame of eyeglasses worn by the user and takes thermal measurements of a region on the user's nose 541, while the user eats different types of food. The dotted lines on the graph indicate when the user started eating each type of food. The nasal temperature increases shortly after starting eating the persimmon; however, it may reach a threshold indicating an allergic reaction only after some time, during which the user eats the pizza or the ice cream. Thus, in this case, the allergic reaction should likely be attributed to the persimmon or the soup, and not attributed to the pizza or the ice cream. Optionally, outward-facing head-mounted visible-light camera 542 takes images of the food the user eats, and the computer uses image processing to detect the types of food.

Another approach for identifying a cause of an allergic reaction (a "trigger" of an allergic reaction), involves analysis of potential triggers and the user's detected response when affected by the potential triggers. In one embodiment, the computer is further configured to: receive indications of times during which the user was exposed to potential triggers of the allergic reaction, and select a trigger, from among the potential triggers, based on the indications and extents of the allergic reaction detected based on $TH_N$. Optionally, during most of the time the user was affected by the trigger, an effect of the trigger, as manifested via changes to $TH_N$, was higher than effects of most of the potential triggers. Optionally, a camera is utilized to take images of the surroundings of the user, and the computer generates at least some of the indications based on analysis of the images. In one example, the exposure to the potential triggers involves consuming a certain drug and/or a certain food item. In another example, the exposure to the potential triggers involves being exposed to pollen, dust, and/or a certain cosmetics product. In still another example, the exposure to the potential triggers involves the user being at a certain location, and/or the user being in contact with a certain animal.

In some embodiments, determination of the extent of the allergic reaction may be utilized in the context of allergen challenge tests. For example, the system may receive an indication of when a non-invasive intranasal histamine and/or an allergen challenge is performed, and estimate effects of the histamine and/or allergen challenge in the tissues, based on an increase of nasal temperature as observed in $TH_N$. In one example, this involves utilizing a change in $TH_N$, induced by the histamine provocation (of the non-invasive intranasal histamine), as a marker of an intensity of the activity of the histamine in the nose. In another example, this may involve utilizing a change in $TH_N$, induced by the allergen challenge, as a marker of an intensity of the activity of the allergen in the nose.

Figure 21:
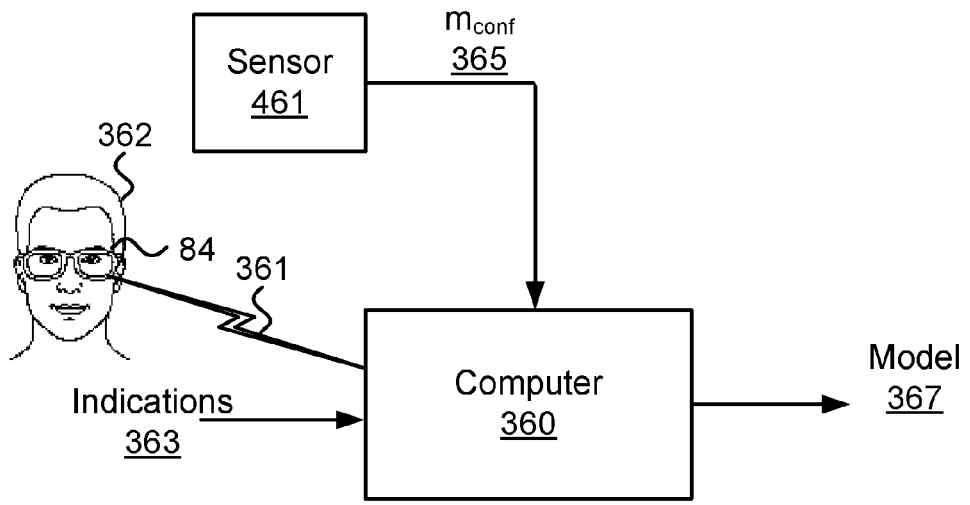
FIG. 21 illustrates an embodiment of a system that generates a model used to detect an allergic reaction.

FIG. 21 illustrates one embodiment of a system that generates a model to detect an allergic reaction. The system includes a CAM and a computer 360. Optionally, CAM is physically coupled to a frame worn on the head of a user 362. CAM takes measurements of a region on the nose ($TH_N$) 361 of the user. Optionally, CAM weighs below 10 g and is located less than 15 cm from the user's face.

In one embodiment, the computer 360 generates samples based on data comprising: (i) $TH_N$ 361, and (ii) indications 363, which correspond to different times, which are indicative of whether the user 362 experienced an allergic reaction at the different times. Optionally, each sample comprises: (i) feature values based on $TH_N$ taken during a certain period (which are from among $TH_N$ 361), and (ii) a label based on an indication from among the indications 363, which is indicative of whether the user 362 had an allergic reaction and/or to what extent the user 362 had the allergic reaction. Optionally, the label is indicative of the extent of the allergic reaction of the user 362 during the certain period and/or up to a certain time after the certain period (e.g., up to 30 minutes after the certain period). Optionally, at least some of the feature values in the sample may be generated based on other sources of information, as explained below. The computer 360 trains a model 367 based on the samples. Optionally, the computer 360 also provides the model 367 to be used by a system that detects an allergic reaction based on $TH_N$, such as the system illustrated in FIG. 22.

The indications 363 may be generated in different ways. In one embodiment, some of the indications 363 are generated by an entity that observes the user 362, such as a human observer or a software program (e.g., a software agent operating on behalf of the user). In another embodiment, some of the indications 363 are provided by the user 362. For example, the user may provide an indication via a smartphone app by pressing a certain button on a screen of a smartphone, and/or by speech that is interpreted by a software agent and/or a program with speech analysis capabilities. In yet another embodiment, some of the indications are determined based on analysis of the user's behavior. For example, monitoring the user using a camera and/or a microphone may indicate that the user is suffering from an allergic reaction by detecting coughing and/or sneezing. And in still another embodiment, some of the indications are determined based on physiological signals of the user, which are not thermal measurements of ROIs on the face, such as measurements of the user's heart rate and/or brainwave activity.

The following are some examples of feature values that may be generated for the samples used to train the model 367. The samples include feature values based on $TH_N$ of the user 362 (from among $TH_N$ 361), which were taken during a certain period, and possibly other information sources mentioned below. Additionally, the samples may include feature values generated based on $m_{conf}$ taken during the certain period (as discussed below).

In one embodiment, the computer 360 receives additional measurements of the user 362 taken during the certain period, and generates feature values based on the additional measurements. Optionally, the additional measurements are indicative of: a heart rate, heart rate variability, brainwave activity, galvanic skin response, muscle activity, and/or an extent of movement. In another embodiment, the computer 360 receives measurements of the environment in which the user 362 was in during the certain period and generates feature values based on the measurements of the environment. Optionally, each measurement of the environment is indicative of: a temperature of the environment, a humidity level of the environment, a noise level of the environment, air quality in the environment, a wind speed in the environment, an extent of precipitation in the environment, and/or an infrared radiation level in the environment.

In another embodiment, the computer 360 generates feature values based on values indicative of exposure of the user 362 to allergens during the certain period. Optionally, the values are indicative of: consumption of a certain drug, consumption of a certain food item, exposure to at least a certain concentration of pollen, exposure to at least a certain concentration of dust, exposure to a certain cosmetics product, and/or exposure to a certain aerosol.

In yet another embodiment, the computer 360 receives measurements (denoted $m_{conf}$ 365), which are indicative of at least one of the following confounding factors: a skin inflammation on the user's face, touching the user's face, a magnitude of thermal radiation directed at the user's face, and a magnitude of direct airflow on the user's face. Optionally, $m_{conf}$ 365 are measured utilizing the sensor 461. Optionally, the computer 360 generates feature values based on $m_{conf}$ from among $m_{conf}$ 365, which were taken during the certain period.

The sensor 461 may involve different types of sensors in embodiments described herein. In one example, the sensor 461 is physically coupled to a frame worn on the head of the user 362. In another example, the sensor 461 is coupled to a device carried by the user 362, such as a smartphone, a smartwatch, and/or smart clothing (e.g., clothing embedded with sensors that can measure the user and/or the environment). In yet another example, the sensor 461 may be an external sensor that is not carried by the user 362. The following are some examples of specific types of sensors that the sensor 461 may include. In one example, the sensor 461 is a visible-light camera physically coupled to the frame, and configured to take images of a region on the user's face that includes at least 25% of the nose. Optionally, in this example, the confounding factor includes inflammation of the skin, skin blemishes, and/or touching the face. In another example, the sensor 461 includes a movement sensor that measures a movement of the user 362 and the confounding factor involves the user walking, running, exercising, bending over, and/or getting up from a sitting or lying position. And in yet another example, the sensor 461 measures at least one of the following environmental parameters: a temperature of the environment, a humidity level of the environment, a noise level of the environment, air quality in the environment, a wind speed in the environment, an extent of precipitation in the environment, and an infrared radiation level in the environment.

In one embodiment, the model 367 is trained on samples that were generated based on $TH_N$ taken while the user 362 had an allergic reaction, and samples that were generated based on $TH_N$ taken while the user 362 did not have an allergic reaction.

The samples utilized to train the model 367 may be generated based on feature values taken while user 362 was in different environments during first and second periods, optionally with different environmental conditions, such as (i) the environment temperature was at least 10° C. higher during the first period than during the second period; (ii) the humidity level in the environment during the first period was at least 30% higher than the humidity level during the second period; and (iii) the user was exposed to rain, hail, and/or snow during the first period, while the user was not exposed to any of rain, hail, and snow during the second period.

Additionally or alternatively, the samples utilized to train the model 367 may be generated based on feature values taken while the user 362 was in various situations during first and second periods, such as (i) the user 362 was sedentary during the first period, while the user 362 was walking, running, or biking during the second period; and/or (ii) the user 362 was indoors during the first period, while the user 362 was outdoors during the second period.

Additionally or alternatively, the samples utilized to train the model 367 may be based on $TH_N$ taken over a long period of time, such as more than a day, more than a week, more than a month, or more than a year.

Training the model 367 may involve various computational approaches. In one example, training the model 367 may involve selecting, based on the samples, a threshold; if a certain feature value reaches the threshold then an allergic reaction is detected. In another example, the computer 360 utilizes a machine learning-based training algorithm to train the model 367 based on the samples. Optionally, the model includes parameters of at least one of the following models: a regression model, a model utilized by a neural network, a nearest neighbor model, a model for a support vector machine for regression, and a model of a decision tree.

In some embodiments, the computer 360 may utilize deep learning algorithms to train the model 367. In one example, the model 367 may include parameters describing multiple hidden layers of a neural network. In one embodiment, when $TH_N$ include measurements of multiple pixels, such as when CAM includes a FPA, the model 367 may include parameters of a convolution neural network (CNN). In another embodiment, detecting the allergic reaction may be done based on multiple, possibly successive, measurements. For example, the allergic reaction may involve a progression of a state of the user (e.g., a gradual warming of the nose). In such cases, detecting the allergic reaction may involve retaining state information that is based on previous measurements. Optionally, the model 367 may include parameters that describe an architecture that supports such a capability. In one example, the model 367 may include parameters of a recurrent neural network (RNN), which is a connectionist model that captures the dynamics of sequences of samples via cycles in the network's nodes. This enables RNNs to retain a state that can represent information from an arbitrarily long context window. In one example, the RNN may be implemented using a long short-term memory (LSTM) architecture. In another example, the RNN may be implemented using a bidirectional recurrent neural network architecture (BRNN).

FIG. 22 illustrates one embodiment of a system configured to detect an allergic reaction. The system includes a CAM and a computer 364. CAM takes measurements of a region on the nose ($TH_N$) 368 of the user 362. Optionally, CAM weighs below 10 g and is located less than 15 cm from the user's face.

The computer 364 generates feature values and utilize the model 367 to detect an allergic reaction of the user 362 based on the feature values. Some feature values are generated based on $TH_N$ 368, and some feature values may be generated based on other data (as described below). Optionally, the model 367 was trained based on previous $TH_N$ of the user 362 (e.g., $TH_N$ 361). Optionally, the previous $TH_N$ of the user 362 were taken during different days and/or over more than a week. Optionally, the previous $TH_N$ include: a first set of $TH_N$ taken while the user had an allergic reaction, and a second set of $TH_N$ taken while the user did not have an allergic reaction.

The feature values generated by the computer 364 are similar in their nature to the feature values generated by the computer 360, which were discussed in more detail above. Optionally, the same modules and/or procedures are used by the computer 364 and the computer 360 to generate feature values based on $TH_N$ (and possibly other data). Some examples of feature values that may be generated by the computer 364 based on $TH_N$ 368 and possibly other data include: (i) values comprised in $TH_N$ 368 (optionally these values may undergo various forms of filtering and/or normalization), (ii) values of one or more respiratory parameters calculated based on $TH_N$ 368, (iii) values generated based on additional measurements of the user 362 (e.g., measurements of heart rate, heart rate variability, brainwave activity, galvanic skin response, muscle activity, and an extent of movement), and/or (iv) measurements of the environment in which the user 362 was in while $TH_N$ 368 were taken.

In one embodiment, the computer 364 may receive indications indicative of exposure of the user 362 to an allergen while $TH_N$ 368 were taken, or up to a predetermined duration before $TH_N$ 368 were taken (e.g., up to twelve hours before), and generate feature values based on the indications. Optionally, the indications are indicative of consumption of a certain drug, consumption of a certain food item, exposure to at least a certain concentration of pollen, exposure to at least a certain concentration of dust, exposure to a certain cosmetics product, and/or exposure to a certain aerosol. Optionally, determining exposure of the user 362 to the allergen may be done by analyzing images received from a camera that captures substances consumed by the user 362.

In another embodiment, the computer 364 may receive measurements ($m_{conf}$ 371), which are indicative of at least one of the following confounding factors: a skin inflammation on the user's face, touching the user's face, a magnitude of thermal radiation directed at the user's face, and/or a magnitude of direct airflow on the user's face. Optionally, $m_{conf}$ 371 are measured utilizing the sensor 461. In one embodiment, the computer 364 generates at least some of feature values based on $m_{conf}$ 371 and utilizes the at least some feature values to detect the allergic reaction.

In one embodiment, the computer 364 utilizes the model 367 to calculate, based on the feature values, a value indicative of the extent of an allergic reaction of the user 362. Optionally, the extent is presented to the user 362 via UI 373. Optionally, responsive to the extent reaching a threshold, the computer 364 generates an alert 372 that is presented to the user 362 via the UI 373.

In one embodiment, the extent of the allergic reaction may be indicative of whether there is an allergic reaction, the severity of the allergic reaction (e.g., a level of manifestation of symptoms on a scale of 1 to 10), and/or the duration of the allergic reaction (e.g., total time of the allergic reaction and/or time remaining until the allergic reaction subsides). Optionally, the extent may be indicative of the time until the allergic reaction reaches its peak severity (e.g., a rash, coughing, respiratory distress, sneezing), and/or the expected degree of severity of the allergic reaction.

In one embodiment, the computer 364 detects an early rise in nasal temperature of the user 362, which is detectable before the user 362 is aware of a manifestation of a symptom of the allergic reaction. Optionally, the UI 373 may present the user 362 with the alert 372 that is indicative of a possible allergic reaction, before the user 362 is aware of the symptom. In one example, an early rise in nasal temperature may involve a rise of at least 0.5° C. within less than 10 minutes and/or a rise of at least 0.75° C. within less than 20 minutes.

The system may optionally include additional CAMs, and thermal measurements of the additional CAMs may be used to generate feature values similarly to how $TH_N$ 368 are utilized. Optionally, the additional CAMs are physically coupled to a frame worn on the head of the user 362. For example, the system may include a second CAM, or second and third CAMs (CAM2 and CAM3, respectively), each of which weighs below 10 g and is located less than 15 cm from the user's face. CAM2 and CAM3 are located to the right and to the left of the vertical symmetry axis that divides the face of the user 362, respectively, and take thermal measurements of regions on the right and left cheeks ($TH_{ROI1}$ and $TH_{ROI2}$, respectively), respectively. Optionally, the computer 364 generates additional feature values based on $TH_{ROI1}$ and $TH_{ROI2}$, and utilizes the additional features values to detect the allergic reaction. In another example, the system includes a second CAM, or second and third CAMs (CAM2 and CAM3), each of which weighs below 10 g and is located less than 15 cm from the user's face. CAM2 and CAM3 are located to the right and to the left of the vertical symmetry axis, respectively, and take thermal measurements of regions on the right and left periorbital areas ($TH_{ROI1}$ and $TH_{ROI2}$, respectively). Optionally, the computer 364 generates additional feature values based on $TH_{ROI1}$ and $TH_{ROI2}$, and utilizes the additional feature values to detect the allergic reaction.

Analysis of detections of allergic reactions combined with information regarding potential triggers that affected the user at different times can reveal what are likely triggers of the allergic reaction. Some examples of potential triggers that may be considered triggers for certain users include ingested substances such as food (e.g., eggs, dairy, or peanuts) or certain drugs and chemicals and/or compounds to which the user may be exposed (e.g., pollen, dust, a certain cosmetics product, and a certain aerosol). Additionally, a trigger may be an indirect potential trigger that is correlated with allergic reactions of the user, such as being at a certain location, being in contact with a certain animal, conducting in a certain activity, and being in contact with a certain object.

Figure 23:
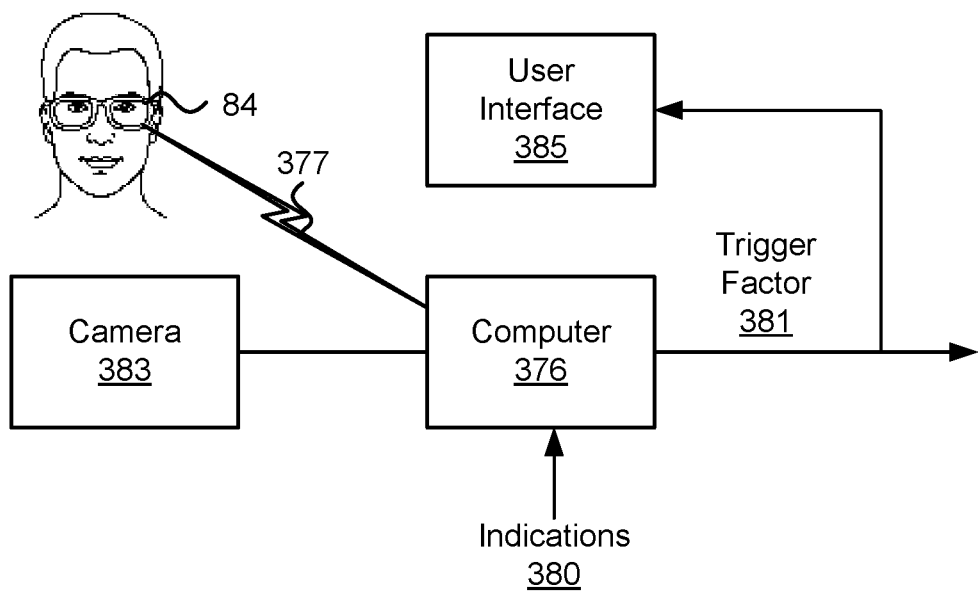
FIG. 23 illustrates an embodiment of a system configured to select a trigger of an allergic reaction of a user.

FIG. 23 illustrates one embodiment of a system configured to select a trigger of an allergic reaction of a user. The system includes a CAM and a computer 376. The system may optionally include a frame 84, a camera 383, and/or a UI 385. CAM takes thermal measurements of a region on the nose ($TH_N$, 377) of the user.

In one embodiment, the thermal camera used to take $TH_N$ 377 is a head-mounted thermal camera. In another embodiment, the thermal camera used to take $TH_N$ 377 is not a head-mounted thermal camera. Examples of non-head-mounted thermal cameras include (i) thermal cameras embedded in a device such as a smartphone or a smartwatch, (ii) a thermal camera embedded in a device such as a laptop computer, a tablet, a television, or a gaming console, and/or (iii) a standalone thermal camera.

In some embodiments, multiple thermal cameras may be utilized to measure $TH_N$ 377. Additionally or alternatively, $TH_N$ 377 may include thermal measurements of multiple ROIs on the user's nose and/or thermal measurements of additional ROIs on other regions of the user's face (besides the nose).

$TH_N$ 377 are provided, in one embodiment, to the computer 376, which detects, based on $TH_N$ 377, extents of the allergic reaction of the user at different times. Optionally, the computer 376 employs a similar approach for detecting the extents of the allergic reaction to the approach described above involving the computer 364.

In some embodiments, detecting the extents of the allergic reaction of the user at different times may involve utilizing thermal measurements of other regions on the face, in addition to $TH_N$ 377.

In one example, the system includes second and third CAMs located to the right and to the left of the vertical symmetry axis that divides the user's face, which take thermal measurements of regions on the right and left cheeks ($TH_R$ and $TH_L$, respectively). Optionally, the computer 376 detects the extents of the allergic reaction also utilizing $TH_R$ and $TH_L$ (in addition to $TH_N$ 377).

In another example, the system includes second and third CAMs located to the right and left of a vertical symmetry axis that divides the user's face, respectively, which take thermal measurements of regions on the right and left periorbital areas ($TH_R$ and $TH_L$, respectively). Optionally, the computer 376 detects the extents of the allergic reaction also utilizing $TH_R$ and $TH_L$ (in addition to $TH_N$ 377).

The computer 376 is configured, in one embodiment, to receive indications 380 of potential triggers that affected the user at various times. Optionally, each of the indications 380 is indicative of a time during which the user was exposed to a certain potential trigger. Additionally or alternatively, each of the indications 380 may be indicative of a time during which the user was affected by a certain potential trigger. In some embodiments, at any given time, the user may be exposed to more than one of the potential triggers. Optionally, at least some of $TH_N$ 377, and optionally all of $TH_N$ 377, were taken while the user was exposed to two or more of the potential triggers.

The computer 376 selects a trigger 381, from among the potential triggers, based on the indications 380 and the extents of the allergic reaction. Optionally, an effect of a potential trigger is indicative how much the potential trigger influences the extent of the user's allergic reaction, which can range from no influence to a profound influence. Optionally, during most of the time the user is affected by the trigger 381, the effect of the trigger 381 on the extent of the allergic reaction of the user is higher than the effect of most of the other potential triggers on the allergic reaction of the user.

In one embodiment, the indications 380 include a list of periods of time during which various potential triggers affected the user. Optionally, the indications 380 are provided via a data structure and/or a queryable system that provides information for different points in time about which of the potential triggers affected the user at the points in time. Following are three examples of types of potential triggers that may be analyzed.

In a first example, some of the potential triggers relate to allergens in various foods, beverages, and/or other substances that may be consumed and digested by the user and may lead to an allergic reaction. For instance, the indications 380 may comprise a certain indication of a potential trigger that is indicative of the user consuming a certain drug and/or a certain food item.

In a second example, some of the potential triggers relate to allergens to which the user may be exposed in the environment. Optionally, an allergic reaction may occur after such an allergen is inhaled by the user and/or comes in contact with the user's skin. For instance, the indications 380 may comprise a certain indication of a potential trigger that is indicative of the user being exposed to pollen, dust, a certain cosmetics product, and/or a certain aerosol (e.g., a certain perfume fragrance).

In a third example, some of the potential triggers indirectly relate to the allergic reaction (e.g., they may be correlated with allergic reactions of the user). For instance, the indications 380 may include a certain indication of a potential trigger that is indicative of the user being at a certain location, the user being in contact with a certain animal, the user conducting in a certain activity, and/or the user being in contact with a certain object.

The extent of an allergic reaction may depend on quantitative aspects of the potential triggers. For example, a person who is allergic to dairy products may not have a noticeable allergic reaction following digestion of a small amount of dairy (e.g., adding milk to a cup of coffee), but may have a noticeable allergic reaction following a consumption of a larger amount of a dairy product (e.g., drinking a large milkshake). Thus, in some embodiments, the indications 380 include values that quantify how much at least some of the potential triggers affected the user. For example, these values may corresponds to amounts of substances consumed by the user, time spent by the user in certain environments, and/or values of environmental parameters (e.g., a concentration of pollen in the air).

The trigger 381 may be correlated with the occurrence of an allergic reaction of the user. Additionally, in some embodiments, the trigger 381 may be considered a direct cause of the allergic reaction (e.g., when the trigger 381 is a substance to which the user's immune system has an excessive reaction). Optionally, during most of the time the user was affected by the trigger 381, an effect of the trigger 381, as manifested via changes to $TH_N$, was higher than effects of most of the potential triggers. Optionally, the trigger 381 has a maximal effect (i.e., there is no other potential triggers that have a higher effect). Optionally, the trigger 381 has an effect that reaches a threshold, while the effect of most of the potential triggers does not reach the threshold.

In some embodiments, the effect of the trigger 381 is higher than the effect observed when the trigger 381 does not affect the user. For example, based on the values indicative of the extents of the allergic reaction and indications 380, an average extent of the allergic reaction of the user at a time $t+\Delta$ when the user was affected by the trigger 381 at some time during $[t, t+\Delta]$, is greater than an average extent of the allergic reaction of the user at a time $t+\Delta$ when the user was not affected by the trigger 381 at any time during $[t, t+\Delta]$. Here $\Delta$ may be some predetermined period of time that is greater than five minutes, fifteen minutes, one hour, four hours, or twelve hours.

There are various ways in which the computer 376 may select, based on the indications 380 and the extents of the allergic reaction, the trigger 381 from among the multiple potential triggers being considered.

In some embodiments, the computer 376 performs a direct analysis of the effect of each of the potential triggers in order to identify which have a large effect (meaning they are likely to cause an allergic reaction with the user). Optionally, the effect of each potential trigger is calculated by determining, based on the indications 380, times at which the user was affected by each potential trigger, and observing the extent of the allergic reaction of the user at one or more times that are up to a certain period $\Delta$ later (where $\Delta$ may be for example a period of time up to 12 hours long or shorter, depending on the type of allergic reaction). In one example, an observed extent of the allergic reaction following being affected by a potential trigger is the maximum extent of the allergic reaction that is observed from the time t the user was affected by the potential trigger until the time $t+\Delta$. In another example, the observed extent of the allergic reaction following being affected by a potential trigger is the extent of the allergic reaction that is observed at the time $t+\Delta$ (when the user was affected by the potential trigger at time t). Optionally, the observed extent of allergic reaction may be normalized based on a quantitative value representing how much the user was affected by the potential trigger (e.g., the observed extent may be normalized based on a dosage of a drug taken or the amount of time spent outdoors). Optionally, the effect of each potential trigger is calculated based on the observed extents of the allergic reactions following being affected by the potential trigger, as described above. In one example, the effect may be an average of the observed extents. In another example, the effect may be a value indicative of the proportion of the observed extents that reach a threshold. Following a calculation of the effects of the potential triggers, in one embodiment, the computer 376 selects the trigger 381 from among the potential triggers based on the effects.

In one embodiment, in order to increase confidence in the selection of the trigger 381, the trigger 381 is selected based on at least a certain number of times in which the user was affected by the trigger 381. For example, the certain number may be at least 3, 5, or 10 different times. Thus, in this embodiment, potential triggers that did not affect the user at least the certain number of times are not selected.

In some embodiments, the computer 376 generates a machine learning-based model based on the indications 380 and the extents of the allergic reaction, and selects the trigger 381 based on an analysis of the model. Optionally, the computer 376 generates samples used to train the model. In one embodiment, the samples may correspond to different times, with each sample corresponding to a time $t=\Delta$ including feature values and a label (target value) indicative of the extent of the allergic reaction of the user at the time $t+\Delta$ (where depending on the embodiment $\Delta$ may have a value between several minutes to 12 or even 24 hours). Optionally, $\Delta$ is at least one minute. Optionally, the label of each sample is determined based on values indicative of the extent of the allergic reaction at the time $t+\Delta$ or thereabouts (e.g., up to an hour before or after the time $t+\Delta$). Optionally, the feature values are based on indications, from among the indications 380, which are indicative of the degree various potential trigger affected the user during a period $[t, t+\Delta]$. Optionally, some of the feature values are indicative of how long before $t+\Delta$ some of the potential triggers affected the user and/or magnitudes of some of the potential triggers (e.g., amounts of food items consumed, dosages of drugs taken, etc.)

Each of the samples described above may be considered to represent a snapshot of potential triggers that affected the user during a certain period and a label that is indicative of the extent of the allergic reaction of the user following being affected by those potential triggers. Given multiple such samples, a machine learning training algorithm can be utilized to train a model for a predictor module that can predict the extent of the user's allergic reaction at a certain time based on feature values that describe the potential triggers that affected the user during a certain period of time leading up to the certain time. For example, if the model is a regression model, the predictor module may perform a dot product multiplication between a vector of regression coefficients (from the model) and a vector of the feature values in order to calculate a value corresponding to the predicted extent of the allergic reaction of the user at the certain time.

When such a predictor module is capable of predicting extents of the allergic reaction of the user based on the feature values described above, this may mean that the model captures, at least to some extent, the effects of at least some of the potential triggers on the extent of the allergic reaction of the user.

Training the model based on the samples described above may involve utilizing various training algorithms. Some examples of models that may be generated in order to be utilized by the predictor module described above include the following models: a regression model (e.g., a regression model), a naïve Bayes model, a Bayes network, a support vector machine for regression, a decision tree, and a neural network model, to name a few possibilities. There are various training algorithms known in the art for generating these models and other models with similar properties.

In some embodiments, the predictor module may be provided multiple inputs representing the potential triggers that affected the user at different points of time. For example, the predictor module may be provided with a series of vectors of feature values, each representing the potential triggers that affect the user during a period (e.g., during one minute, five minutes, thirty minutes, an hour, or six hours). In these embodiments, the predictor module may have a capability to store state information of previous inputs corresponding to earlier times when it comes to predict the extent of the allergic reaction of the user at a certain time. One example of a predictor module with such a capability is a predictor module that is based on a recurrent neural network.

Once the model is trained, it may be analyzed by the computer 376 to determine the effects of one or more of the potential triggers on the extent of the allergic reaction. Depending on the type of model that was trained, this analysis may be performed in different ways.

In one embodiment, the computer 376 performs the analysis of the model by evaluating parameters of the model that correspond to the potential triggers. Optionally, the computer 376 selects as the trigger 381 a certain potential trigger that has a corresponding parameter that is indicative of an effect that reaches a threshold while effects indicated in parameters corresponding to most of the potential triggers do not reach the threshold. In one example, the model may be a linear regression model in which each potential trigger corresponds to a regression variable. In this example, a magnitude of a value of a regression coefficient may be indicative of the magnitude of the effect of its corresponding potential trigger. In another example, the model may be a naïve Bayes model in which various classes correspond to extents of an allergic reaction (e.g., a binary classification model that is used to classify a vector of feature values to classes corresponding to allergic reaction vs. no allergic reaction). In this example, each feature value may correspond to a potential trigger, and the class conditional probabilities in the model are indicative of the magnitude of the effect of each of the potential triggers on the user.

In another embodiment, the computer 376 performs an analysis of the model, which may be characterized as "black box" analysis. In this approach, the predictor module is provided with various inputs that correspond to different potential triggers that affect the user, and calculates, based on the inputs and the model, various predicted extents of an allergic reaction of the user. The various inputs can be used to independently and individually increase the degree to which each of the potential triggers affects the user. This type of the model probing can help identify certain potential triggers that display an increase in the predicted extent of the allergic reaction, which corresponds to an increase in the degree to which the potential triggers affect the user (according to the model). Optionally, with the trigger 381 there is a positive correlation observed between increasing the degree to which the trigger 381 affects that user, and the predicted extent of the allergic reaction of the user. Optionally, the trigger 381 is selected from among the potential triggers, responsive to identifying that that: (i) based on a first subset of the various predicted extents of an allergic reaction of the user, an effect of the trigger 381 reaches a threshold, and (ii) based on a second subset of the various predicted extents of an allergic reaction of the user, effects of most of the potential triggers do not reach the threshold.

The indications 380 may be received from various sources. In one embodiment, the user may provide at least some of the indications 380 (e.g., by inputting data via an app and/or providing vocal annotations that are interpreted by a speech analysis software). In other embodiments, some indications 380 are provided by analysis of data sources. Optionally, the computer 376 generates some indications 380 based on the analysis of data obtained from the data sources. The following are some examples of data sources that may be utilized to identify potential triggers that affected the user at different times.

In a first example, a camera 383 captures images of the surroundings of the user. The camera 383 may be head-mounted or belong to a device of the user (e.g., a smartphone or a webcam). In one example, the camera 383 may belong to a camera-based systems such as OrCam (http://www.orcam.com/), which is utilized to identify various objects, products, faces, and/or recognize text. In another example, images captured by the camera 383 may be utilized to determine the nutritional composition of food a user consumes. Such an approach in which images of meals are utilized to generate estimates of food intake and meal composition, is described in Noronha, et al., "Platemate: crowdsourcing nutritional analysis from food photographs", Proceedings of the 24th annual ACM symposium on User interface software and technology, ACM, 2011.

In a second example, other sensors such as microphones, accelerometers, thermometers, pressure sensors, and/or barometers may be used to identify potential triggers that affect the user, by identifying what the user is doing (e.g., by analyzing movement patterns) and/or under what conditions (e.g., by analyzing ambient noise, temperature, and/or pressure).

In a third example, measurements of the environment that user is in are another source of information for determining potential stressor. The measurements may be received from a third party (e.g., a website that provides environmental information for various locations), and may indicate temperature, pressure, humidity, and/or particle counts for various types of chemicals or compounds (e.g. pollutants and/or allergens).

In a fourth example, Internet of Things (IoT) devices provide information when they are moved and/or utilized. Additionally or alternatively, communications of the user (e.g., email, text messages, voice conversations, and/or video conversations) may also be analyzed to provide context and/or to identify some potential stressors. Similarly, the user's calendar and/or schedule, as well as billing information, may provide information that may be used in some embodiments to identify potential stressors.

There are various approaches known in the art for identifying, indexing, and/or searching for potential triggers that may affect the user, which may be utilized in embodiments described herein. In one example, identifying potential triggers that may be done according to the teachings described in U.S. Pat. No. 9,087,058 titled "Method and apparatus for enabling a searchable history of real-world user experiences", which describes a searchable history of real-world user experiences of a user utilizing data captured by a mobile computing device. In another example, identifying potential triggers may be done according to the teachings described in U.S. Pat. No. 8,762,102 titled "Methods and systems for generation and rendering interactive events having combined activity and location information", which describes identification of events based on sensor data of mobile devices.

Knowledge of the trigger 381 may be utilized for various purposes. In one embodiment, the trigger 381 is utilized by a software agent operating on behalf of the user in order to better serve the user. For example, the software agent may ensure that food items that are ordered for the user do not include components that are known to trigger an allergic reaction (e.g., if the trigger 381 is a type of food). In another example, the software agent may plan routes for the user that do not include environments in which the trigger 381 may be present (e.g., if the trigger 381 is bloom).

In some embodiments, information about the trigger 381 is provided to the user via a UI 385. UI 385 may be utilized on a day-to-day basis to warn the user when the trigger 381 is detected. Optionally, a database may be consulted to determine whether the identified food items contain the trigger 381. If the trigger 381 is detected, the UI 385 may indicate that to the user.

Due to the mostly symmetric nature of the human body, when the face undergoes temperature changes, e.g., due to external factors such as the temperature in the environment or internal factors such as an activity-related rise in body temperature, the changes to the face are generally symmetric. That is, the temperature changes at a region of interest (ROI) on the left side of the face (e.g., the left side of the forehead) are similar to the temperature changes at the symmetric ROI on the right side of the face (e.g., the right side of the forehead). However, when the temperature on the face changes in an asymmetric way, this can be indicative of various physiological responses and/or undesirable phenomena. Some examples of phenomena that may be identified by detecting asymmetric thermal patterns ("thermal asymmetry") on a user's face include a headache, sinusitis, nerve damage, some types of strokes, orofacial pain, and Bell's palsy. Additionally, some forms of disorders such as Attention Deficit Hyperactivity Disorder (ADHD), stress, anxiety, and/or depression can also be identified based on thermal asymmetry of the forehead, and in some cases of other regions of the face.

In other cases, and sometime depending on personal characteristics of the user, certain physiological responses may manifest differently on different sides of the face. In particular, the temperatures at different positions on the right side of the face may not be a mirror image of the temperatures at the corresponding positions on the left side of the face. Thus, having two or more thermal cameras pointed at different areas of the face can, in some embodiments, help make more accurate detections of a physiological response. For example, stress may be manifested with some people by the cooling of an area on one side of the nose more than the symmetric area on the other side. Similarly, with some people, an allergic reaction may manifest by the nose heating to different extents on each of its sides. Thus, having, in this example, two or more thermal cameras pointed at different sides of the nose, may enable a more accurate detection of the physiological response.

Measuring and utilizing the asymmetric data also improves the robustness of the system against interferences that may cause an asymmetric thermal effect, such as an external heat source located to the user's side, a cooling air-conditioner that blows air from the top, touching and/or wiping one side of the face, and for some people also eating and/or conducting a physical activity. Therefore, utilizing thermal cameras pointed at symmetric ROIs may improve the system's ability to detect a physiological response compared to the case in which just one thermal camera is used.

In one embodiment, a system configured to collect thermal measurements indicative of thermal asymmetry on a user's face includes first and second inward-facing head-mounted thermal cameras (CAM1 and CAM2). Optionally, CAM1 and CAM2 are physically coupled to a frame worn on the user's head, and are located less than 15 cm, 5 cm, or 2 cm from the user's face. Optionally, CAM1 and CAM2 are located at least 0.5 cm to the right and to the left of the vertical symmetry axis that divides the face, respectively. Optionally, each of CAM1 and CAM2 weighs below 10 g, 5 g, or 1 g.

CAM1 and CAM2 take thermal measurements of regions on the right and left sides of the face ($TH_{ROI1}$ and $TH_{ROI2}$, respectively) of the user, and optionally do not occlude $ROI_1$ and $ROI_2$. Optionally, CAM1 and CAM2 are based on thermopile, microbolometer, or pyroelectric sensors, which may be focal-plane array sensors. Optionally, $ROI_1$ and $ROI_2$ have symmetric overlapping above 60%. In one example, CAM1 and CAM2 may be thermal cameras 120 and 122 in FIG. 10. In another example, CAM1 and CAM2 are thermal cameras 126 and 128 in FIG. 11.

The symmetric overlapping is considered with respect to the vertical symmetry axis that divides the face to the right and left portions. The symmetric overlapping between $ROI_1$ and $ROI_2$ may be observed by comparing the overlap between $ROI_1$ and a mirror image of $ROI_2$, where the mirror image is with respect to a mirror that is perpendicular to the front of the face and whose intersection with the face is along the vertical symmetry axis (which goes through the middle of the forehead and the middle of the nose). Depending on the application for which the thermal measurements are utilized, the ROIs may have different degrees of symmetric overlapping. In one example, the symmetric overlapping between $ROI_1$ and $ROI_2$ is above 80% of the smallest area from among the areas of $ROI_1$ and $ROI_2$. In another example, the overlap between $ROI_1$ and $ROI_2$ is above 25% and below 80% of the smallest area from among the areas of $ROI_1$ and $ROI_2$.

Depending on the locations of $ROI_1$ and $ROI_2$, in different embodiments, CAM1 and CAM2 may be located in specific locations on the frame and/or with respect to the face. In one example, $ROI_1$ and $ROI_2$ are on the nose and/or a region on the mouth, and CAM1 and CAM2 are located outside the exhale streams of the mouth and/or nostrils.

In one embodiment, each of CAM1 and CAM2 is located less than 10 cm from the face and there are angles greater than 20° between the Frankfort horizontal plane and the optical axes of CAM1 and CAM2.

Due to the angle between the optical axis of CAM1 and CAM2 and the Frankfort horizontal plane, in some embodiments, the Scheimpflug principle, may be employed in order to capture sharper images. For example, when the user wears the frame, CAM1 and/or CAM2 may have a certain tilt greater than 2° between their sensor and lens planes, in order to produce the sharper images.

In one embodiment, CAM1 and CAM2 utilize focal-plane array (FPA) sensors. Optionally, each FPA includes at least 6 or at least 12 sensing elements (pixels). Optionally, there are angles greater than 20° between the Frankfort horizontal plane and the optical axes of CAM1 and CAM2. Optionally, CAM1 is located to the right of the vertical symmetry axis and takes thermal measurements of a first region of interest ($TH_{ROI1}$), where $ROI_1$ covers more of the right side of the face than of the left side of the face; CAM2 is located to the left of the vertical symmetry axis and takes thermal measurements of a second region of interest ($TH_{ROI2}$), where $ROI_2$ covers more of the left side of the face than of the right side of the face. Optionally, the cameras do not occlude $ROI_1$ and $ROI_2$. Alternatively, the cameras occlude at least part of $ROI_1$ and $ROI_2$.

In some embodiments, the system for collecting thermal measurements indicative of thermal asymmetry on a user's face includes a computer. Optionally, the computer detects a physiological response based on the thermal measurements.

In one embodiment, the detection of the physiological response utilizes a personalized model of the user. Optionally, the computer (i) generates feature values based on $TH_{ROI1}$ and $TH_{ROI2}$, and (ii) utilizes a model to detect the physiological response based on the feature values. Optionally, at least some feature values used to detect the physiological response may be generated based on additional sources of information (other than CAM1 and CAM2), such as additional thermal cameras, additional sensors that measure physiological signals of the user (e.g., heart rate or galvanic skin response), and/or additional sensors that measure the environment. Optionally, the model is trained based on previous $TH_{ROI1}$ and $TH_{ROI2}$ taken while the user had the physiological response. Optionally, the physiological response involves the user experiencing stress, mental workload, fear, sexual arousal, anxiety, pain, a headache, dehydration, intoxication, and/or a stroke. Optionally, the physiological response is associated with facial thermal asymmetry, and the model was trained based on previous feature values taken during different days. Optionally, the previous feature values include: a first set of feature values generated based on $TH_{ROI1}$ and $TH_{ROI2}$ taken while the user had the physiological response, and a second set of feature values generated based on $TH_{ROI1}$ and $TH_{ROI2}$ taken while the user did not have the physiological response.

In different embodiments, the difference between $TH_{ROI1}$ and $TH_{ROI2}$ may be interpreted in different ways. In one embodiment, an extent of a physiological response may be proportional to the difference between $TH_{ROI1}$ and $TH_{ROI2}$ when the value of the difference is in a certain range. Optionally, when the value of the difference is outside of the range, this may be indicative of the occurrence of other phenomena (which are not the physiological response). In another embodiment, when the value of the difference between $TH_{ROI1}$ and $TH_{ROI2}$ reaches a threshold, that is indicative of an occurrence of the physiological response. In yet another embodiment, at least one feature value utilized by a predictor that predicts occurrences of the physiological response is based on the value of the difference between $TH_{ROI1}$ and $TH_{ROI2}$.

Often a change in the thermal asymmetry may be indicative of a physiological response. Optionally, the computer detects a change to thermal asymmetry on the face based on a change between thermal measurements taken at different times. The computer may further calculate the extent of the physiological response based on the change. This calculation can be performed in different ways, as described below.

In one embodiment, the computer calculates the change between the thermal measurements as follows: calculate a temperature difference between $ROI_1$ and $ROI_2$ at time x ($\Delta T_x$) based on [$TH_{ROI1}$, $TH_{ROI2}$] taken at time x, calculate a temperature difference between $ROI_1$ and $ROI_2$ at time y ($\Delta T_y$) based on [$TH_{ROI1}$, $TH_{ROI2}$] taken at time y, and calculate the output indicative of the change in the thermal asymmetry on the face based on a difference between $\Delta T_x$ and $\Delta T_y$.

The embodiment described above may optionally be implemented using a differential amplifier that receives $TH_{ROI1}$ and $TH_{ROI2}$ as inputs, and output the temperature difference between $ROI_1$ and $ROI_2$. Optionally, CAM1 and CAM2 are based on thermopile sensors. Alternatively, CAM1 and CAM2 are based on pyroelectric sensors. In one example, pairs of thermal sensor elements are wired as opposite inputs to a differential amplifier in order for the thermal measurements to cancel each other and thereby remove the average temperature of the field of view from the electrical signal. This allows CAM1 and CAM2 to be less prone to provide false indications of temperature changes in the event of being exposed to brief flashes of radiation or field-wide illumination. This embodiment may also minimize common-mode interference, and as a result improve the accuracy of the thermal cameras.

In another embodiment, the computer calculates the change between the thermal measurements as follows: calculate a temperature change between $TH_{ROI1}$ taken at times $t_1$ and $t_2$ ($\Delta TH_{ROI1}$), calculate a temperature change between $TH_{ROI2}$ taken at times $t_1$ and $t_2$ ($\Delta TH_{ROI2}$), and then calculate the output indicative of the thermal asymmetry on the face based on a difference between $\Delta TH_{ROI1}$ and $\Delta TH_{ROI2}$.

It is noted that sentences such as "calculate a difference between X and Y" or "detect a difference between X and Y" may be achieved by any function that is proportional to the difference between X and Y.

The computer may utilize the change in thermal asymmetry in order to detect a physiological response in various ways. For example, the change may be compared to a threshold, which if reached, is indicative of the occurrence of the physiological response. Optionally, the threshold needs to be reached a certain number of times and/or for a certain amount time, before it is assumed that the user experienced the physiological response. In another example, time series data that include changes to thermal asymmetry of the face may be compared to reference time series comprising changes in thermal asymmetry observed with the physiological response. In still another example, changes in thermal asymmetry may be utilized to generate feature values that are used along with a machine learning-based model to detect an occurrence of a physiological response (as discussed above).

Additional CAMs may be utilized to take thermal measurements used for detecting the physiological response. FIG. 9 illustrates one embodiment of a system that collects thermal measurements indicative of thermal asymmetry on a user's face, which involves additional CAMs. The system includes a frame 90, which has six CAMs coupled to it (some embedded in protruding arms). CAMs 91 and 92 are located on arms on the right and left sides of the top of the frame 90, respectively, and take thermal measurements of regions on the right and left sides of the forehead (97 and 98, respectively). CAMs 93 and 94 are located on the right and left sides of the frame 90 near the nose, respectively, and take thermal measurements of regions on the right and left periorbital areas (99 and 100), respectively. CAMs 95 and 96 are located on arms connected to the bottom of right and left rims, respectively, and take thermal measurements of right and left lower regions of the face (101 and 102, respectively). Optionally, some (or all) of the cameras contain multiple sensing elements.

In one embodiment, the system for collecting thermal measurements indicative of thermal asymmetry on a user's face further includes third and fourth CAMs (in addition to CAM1 and CAM2), each of which: weighs below 10 g, is physically coupled to the frame, and is located less than 15 cm from the face. The third and fourth CAMs take thermal measurements of regions on the right and left sides of the upper lip ($TH_{ROI3}$ and $TH_{ROI4}$, respectively) of the user, without occluding the upper lip. Optionally, the symmetric overlapping between the regions on the right and left sides of the upper lip is above 60%. Optionally, the system includes a computer that (i) generates feature values based on $TH_{ROI1}$, $TH_{ROI2}$, $TH_{ROI3}$, and $TH_{ROI4}$, and (ii) utilizes a model to detect a physiological response based on the feature values. Optionally, the model was trained based on previous $TH_{ROI1}$, $TH_{ROI2}$, $TH_{ROI3}$, and $TH_{ROI4}$ taken while the user had a physiological response associated with at least one of the following: stress, mental workload, fear, sexual arousal, anxiety, pain, a headache, dehydration, intoxication, and a stroke.

In another embodiment, $ROI_1$ and $ROI_2$ are on the right and left sides of the forehead, respectively, and the system further includes at least third and fourth CAMs, located less than 10 cm from the face, which take thermal measurements of regions on the right and left periorbital areas ($TH_{ROI3}$ and $TH_{ROI4}$, respectively). Optionally, the system includes a computer that utilizes a model to detect an emotional state and/or stress level based on $TH_{ROI1}$, $TH_{ROI2}$, $TH_{ROI3}$, and $TH_{ROI4}$. Optionally, the model was trained based on previous $TH_{ROI1}$, $TH_{ROI2}$, $TH_{ROI3}$, and $TH_{ROI1}$ taken during different days. Optionally, the system includes additional fifth and sixth CAMs, located less than 10 cm from the face, which take thermal measurements of regions on the right and left cheeks ($TH_{ROI5}$ and $TH_{ROI6}$, respectively). Optionally, the computer detects the physiological response also based on $TH_{ROI5}$ and $TH_{ROI6}$ (e.g., by generating based on $TH_{ROI5}$ and $TH_{ROI6}$ at least some of the feature values used to detect the physiological response).

In yet another embodiment, the system further includes third and fourth CAMs for taking thermal measurements of the environment to the right and to the left of the face ($TH_{ENV1}$ and $TH_{ENV2}$, respectively). The computer utilizes $TH_{ENV1}$ and $TH_{ENV2}$ to identify asymmetry resulting from the environment rather than from a physiological response. For example, the computer may generate feature values based on $TH_{ENV1}$ and $TH_{ENV2}$, and utilize these feature values, in addition to feature values generated based on thermal measurements of the ROIs on the face, in order to detect the physiological response. Optionally, the third and fourth CAMs are based on at least one of the following sensor types: a thermopile, a pyroelectric sensor, and a microbolometer. Optionally, the environmental cause of the asymmetry involves at least one of the following: sunlight, air blowing from an air-conditioner, radiation from a heater, and radiation from an oven.

The following examples of physiological responses may be identified utilizing embodiments of the system for collecting thermal measurements indicative of thermal asymmetry on a user's face.

There are various forms of sinusitis that may be detected utilizing different embodiments of the system. In one embodiment, $ROI_1$ and $ROI_2$ are on the right and left anterior sinuses, respectively. Optionally, the computer utilizes a model to detect sinusitis based on $TH_{ROI1}$ and $TH_{ROI2}$ (as described above). Optionally, the data used to train the model includes $TH_{ROI1}$ and $TH_{ROI2}$ taken from other users who suffer from maxillary sinusitis, frontal sinusitis, unilateral frontal sinusitis, and/or unilateral maxillary sinusitis. In a first example, $ROI_1$ and $ROI_2$ are on the right and left anterior sinus group, respectively. Optionally, the right/left anterior sinus group includes the right/left frontal sinus, the right/left maxillary sinus, and the right/left anterior ethmoid sinus. In a second example, $ROI_1$ and $ROI_2$ are on the user's right and left frontal sinuses, respectively, and the computer detects an occurrence of a unilateral frontal sinusitis. In a third example, $ROI_1$ and $ROI_2$ are on the user's right and left maxillary sinuses, respectively, and the computer detects an occurrence of a unilateral maxillary sinusitis.

Some forms of strokes may be detected using embodiments of the system. In a first example, $ROI_1$ and $ROI_2$ are on the right and left superficial temporal arteries. In a second example, each of $ROI_1$ and $ROI_2$ cover above 20%, or above 40%, of the right and left sides of the face that include exposed facial skin between the mouth level and the eyebrow level, respectively (e.g., the right and left cheeks and/or the right and left sides of the upper lip). Herein, "exposed facial skin" refers to facial skin that does not have excessive hair growth, such as a beard that usually damages the ability of CAM to measure the skin under the beard. In these two examples, a computer may detect whether the user has a stroke based on changes observed by comparing $TH_{ROI1}$ and $TH_{ROI2}$ taken from the user during different days. Optionally, if the probability that the user has a stroke reaches a certain threshold, such as at least 5%, 25%, or 50%, then the user and/or a third party are alerted about this finding so the user can receive immediate medical attention.

Figure 19:
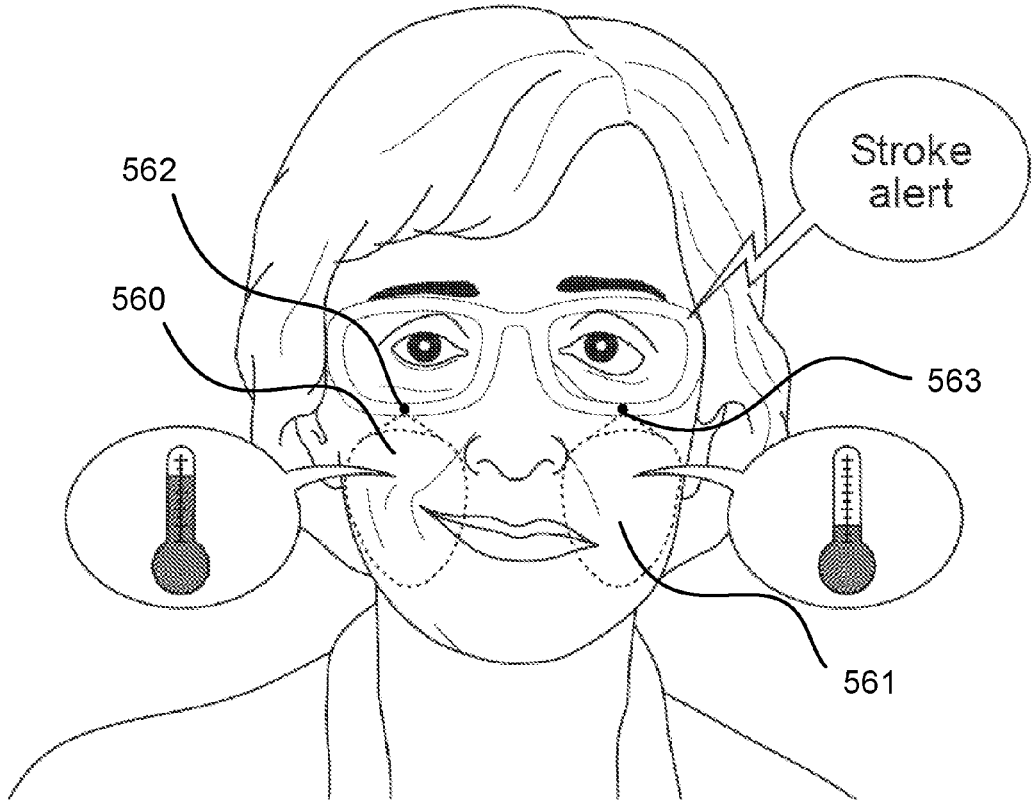
FIG. 19 illustrates a scenario in which an alert regarding a possible stroke is issued.

FIG. 19 illustrates a scenario in which an alert regarding a possible stroke is issued. The figure illustrates a user wearing a frame with at least two CAMs (562 and 563) for measuring ROIs on the right and left cheeks (ROIs 560 and 561, respectively). The measurements indicate that the left side of the face is colder than the right side of the face. Based on these measurements, and possibly additional data, the system detects the stroke and issues an alert. Optionally, the user's facial expression is slightly distorted and asymmetric, and a VCAM provides additional data in the form of images that may help detecting the stroke.

Various forms of nerve damage often cause detectable thermal differences on the face. At times, the thermal differences may manifest prior to changes to the appearance of the face. Thus, thermal measurements may be utilized for early detection of nerve damage, which may improve the outcome of a treatment. For example, in one embodiment, $ROI_1$ and $ROI_2$ may each be on the periorbital area around the eyes, the nose, and/or the mouth. Optionally, the computer may identify nerve damage based on changes observed by comparing $TH_{ROI1}$ and $TH_{ROI2}$ taken from the user during different days, and/or by using a model trained based on measurements of other users taken while they had nerve damages.

Headaches (which also include migraines), symptomatic behavior of Attention Deficit Hyperactivity Disorder (ADHD), and/or anger attacks are physiological responses that may also be detected by embodiments described herein. In one embodiment, detecting these physiological responses is done with a system in which $ROI_1$ and $ROI_2$ are on the right and left sides of the user's forehead. Alternatively, $ROI_1$ and $ROI_2$ may cover right and left regions on the periorbital areas, the nose, and/or the mouth. Optionally, the computer detects headaches utilizing a model that was trained based on previous $TH_{ROI1}$ and $TH_{ROI2}$ taken during different days, optionally including samples taken while the user had a headache and while the user did not have a headache.

Additionally, in some embodiments, a relationship between the stress the user feels and headache the user has may be studied. Optionally, the computer receive training data comprising physiological measurements indicative of levels of stress of the user, values indicative of durations during which the user felt stressed, and values indicative of durations during which the user had a headache. The computer utilizes a machine learning-based training algorithm to train the model based on the training data. The model may be used to detect a headache based on $TH_{ROI1}$ and $TH_{ROI2}$ and optionally, additional values indicative of stress the user felt.

Orofacial pain often results from dental causes (e.g., toothache caused by pulpitis or a dental abscess). Such pain may also be detected utilizing some embodiments of the system. In one embodiment, $ROI_1$ and $ROI_2$ are on the right and left sides of at least one of the jaws. Optionally, the computer detects orofacial pain based on $TH_{ROI1}$ and $TH_{ROI2}$ utilizing a model that was trained based on previous $TH_{ROI1}$ and $TH_{ROI2}$ taken during different days.

Bell's palsy is another medical disorder that may be identified based on thermal measurements. In one embodiment, the system includes a computer that detects Bell's palsy based on comparing $TH_{ROI1}$ and $TH_{ROI2}$ taken from the user during different days. Optionally, the system further includes a VCAM for taking photos of the face, and the computer analyzes the photos for asymmetry in order to improve the probability of identifying Bell's palsy. For example, the detection of Bell's palsy may be done based on feature values that include feature values generated based on the thermal measurements (e.g., corresponding to differences in values of thermal measurements at the same locations during different times), and feature values generated based on images taken by VCAM (e.g., corresponding to differences in facial features at the same locations during different times). Optionally, the system suggests the user to take a medical examination when the facial thermal asymmetry reaches a threshold for more than a predetermined duration (such as 1 minute, 5 minutes, or more than 30 minutes).

In one embodiment, a method for detecting a physiological response that causes a thermal asymmetry on a user's face includes the following steps: In step 1, taking, using first and second CAMs (CAM1 and CAM2), thermal measurements of regions on the right and left sides of the face ($TH_{ROI1}$ and $TH_{ROI2}$, respectively). The regions on the right and left sides of the face have a symmetric overlapping above 60%. CAM1 and CAM2 are less than 10 cm away from the face, and the angles between the Frankfort horizontal plane and the optical axes of CAM1 and CAM2 are greater than 20°. And in Step 2, detecting the physiological response based on $TH_{ROI1}$ and $TH_{ROI2}$.

In one embodiment, the method further includes the steps of (i) generating feature values based on $TH_{ROI1}$ and $TH_{ROI2}$, and (ii) utilizing a model to detect the physiological response based on the feature values. Optionally, the model was trained based on previous $TH_{ROI1}$ and $TH_{ROI2}$ taken while the user had a physiological response associated with stress, mental workload, fear, sexual arousal, anxiety, pain, a headache, dehydration, intoxication, and/or a stroke. Optionally, the previous $TH_{ROI1}$ and $TH_{ROI2}$ were taken on different days. Optionally, the method further alerts about the physiological response that causes the thermal asymmetry.

Some of the disclosed embodiments may be utilized to detect a stress level of a user based on thermal measurements of the user's face, such as the periorbital areas (i.e., areas around the eyes). In one embodiment, a system configured to detect a stress level includes a CAM and a computer. CAM takes thermal measurements of a region on a periorbital area ($TH_{ROI1}$) of the user, and is located less than 10 cm from the user's head. The computer detects the stress level based on $TH_{ROI1}$.

In one embodiment, in which the region is on the periorbital area of the right eye, the system further includes a second inward-facing head-mounted thermal camera (CAM2), which is located less than 10 cm from the user's head and takes thermal measurements of a region on the periorbital area of the left eye ($TH_{ROI2}$). Optionally, the computer detects the stress level based on both $TH_{ROI1}$ and $TH_{ROI2}$. Optionally, CAM and CAM2 are located at least 0.5 cm to the right and to the left of the vertical symmetry axis (which goes through the middle of the forehead and the middle of the nose), respectively. Optionally, each of CAM and CAM2 weighs below 10 g and is based on a thermopile, a microbolometer, or a pyroelectric sensor, which may be a focal-plane array sensor.

It is to be noted that while various embodiments may utilize a single CAM, due to asymmetrical placement of blood vessels in the face, thermal emissions of faces of many people are asymmetric to a certain extent. That is, the pattern of thermal emission from the left side of the face may be different (possibly even noticeably different) from the pattern of thermal emission from the right side of the face. Thus, for example, the temperature changes at the periorbital areas, in response to experiencing at least a certain level of stress, may be asymmetric for some users. The fact that various embodiments described below may include two (or more) CAMs that take measurements of ROIs covering different sides of the face (referred to as $TH_{ROI1}$ and $TH_{ROI2}$) can enable the computer to account for the thermal asymmetry when detecting the stress level.

In some cases, interferences (such as an external heat source, touching one of the eyes, or an irritated eye) cause an asymmetric effect on the right and left periorbital areas. As a result, utilizing right and left CAMs, which are located in different angles relative to the interfering source, provides the computer additional data that can improve its performances. The following are some examples of various ways in which the computer may account for the asymmetry when detecting the stress level based on $TH_{ROI1}$ and $TH_{ROI2}$, which include measurements of the of regions on the periorbital areas of the right and left eyes of the user, respectively.

In one embodiment, when comparing $TH_{ROI1}$ and $TH_{ROI2}$ to thresholds, the computer may utilize different thresholds for $TH_{ROI1}$ and $TH_{ROI2}$, in order to determine whether the user experienced a certain level of stress. Optionally, the different thresholds may be learned based on previous $TH_{ROI1}$ and $TH_{ROI2}$, which were measured when the user experienced the certain level of stress and/or suffered from certain interferences.

In another embodiment, the computer may utilize different reference time series to which $TH_{ROI1}$ and $TH_{ROI2}$ are compared in order to determine whether the user experienced the certain level of stress. Optionally, accounting for the asymmetric manifestation of the stress is reflected in the fact that a reference time series to which $TH_{ROI1}$ is compared is different from a reference time series to which $TH_{ROI2}$ is compared.

In yet another embodiment, when the computer utilizes a model to calculate a stress level based on feature values generated based on $TH_{ROI1}$ and/or $TH_{ROI2}$. Optionally, the feature values include: (i) at least first and second feature values generated based on $TH_{ROI1}$ and $TH_{ROI2}$, respectively; and/or (ii) a third feature value indicative of the magnitude of a difference between $TH_{ROI1}$ and $TH_{ROI2}$. In this embodiment, the computer may provide different results for first and second events that involve the same average change in $TH_{ROI1}$ and $TH_{ROI2}$, but with different extents of asymmetry between $TH_{ROI1}$ and $TH_{ROI2}$, and/or different magnitudes of interferences on the right and left eyes.

In still another embodiment, the computer may utilize the fact that asymmetric temperature changes occur when the user experiences stress in order to distinguish between stress and other causes of temperature changes in the periorbital areas. For example, drinking a hot beverage or having a physical exercise may cause in some people a more symmetric warming pattern to the periorbital areas than stress. Thus, if such a more symmetric warming pattern is observed, the computer may refrain from identifying the temperature changes as being stress-related. However, if the warming pattern is asymmetric and corresponds to temperature changes in the periorbital areas of the user when the user experiences stress, then the computer may identify the changes in the temperatures being stress-related.

The computer may employ different approaches when detecting the stress level based on $TH_{ROI1}$ (and possibly other sources of data such as $TH_{ROI2}$). In one embodiment, the computer may compare $TH_{ROI1}$ (and possibly other data) to a threshold(s), which when reached would indicate a certain stress level. In another embodiment, the computer may generate feature values based on $TH_{ROI1}$ and $TH_{ROI2}$, and utilize a model (also referred to as a "machine learning-based model") to calculate a value indicative of the stress level based on the feature values (calculating the value indicative of the stress level may be considered herein as "detecting the stress level"). At least some of the feature values are generated based on $TH_{ROI1}$. Optionally, at least some of the feature values may be generated based on other sources of data, such as $TH_{ROI2}$ and/or $TH_{ROI3}$ (described below). Optionally, the model was trained based on samples comprising feature values generated based on previous $TH_{ROI1}$ (and possibly other data, as explained below), and corresponding labels indicative of a stress level of the user. Optionally, the data used to train the model includes previous $TH_{ROI1}$ taken while the user was under elevated stress, and other previous $TH_{ROI1}$ taken while the user was not under elevated stress. Optionally, "elevated stress" refers to a stress level that reaches a certain threshold, where the value of the threshold is set according to a predetermined stress scale (examples of stress scales are given further below). Optionally, "elevated stress" refers to a physiological state defined by certain threshold values of physiological signals (e.g., pulse, breathing rate, and/or concentration of cortisol in the blood).

In a first embodiment, when the stress level exceeds a certain value, $TH_{ROI1}$ reach a threshold, and when the stress level does not exceed the certain value, $TH_{ROI1}$ do not reach the threshold. Optionally, the stress level is proportional to the values of $TH_{ROI1}$ (which are thermal measurements of the region on the periorbital area), such that the higher $TH_{ROI1}$ and/or the higher the change to $TH_{ROI1}$ (e.g., with reference to a baseline), the higher the stress level.

In a second embodiment, the computer detects the stress level based on a difference between $TH_{ROI1}$ and a baseline value determined based on a set of previous measurements taken by CAM. Optionally, most of the measurements belonging to the set were taken while the user was not under elevated stress.

In a third embodiment, the stress level is detected using a model and feature values generated based on additional measurements ($m_{conf}$) of the user and/or of the environment in which the user was in while $TH_{ROI1}$ were taken. $m_{conf}$ may be taken by sensor 461. Optionally, $m_{conf}$ are indicative of an extent to which a confounding factor occurred while $TH_{ROI1}$ were taken. The following are some examples of sources of information for $m_{conf}$, which may be used to detect the stress level.

In a first example, $m_{conf}$ are physiological signals such as a heart rate, heart rate variability, galvanic skin response, a respiratory rate, and respiratory rate variability, which are taken using sensors such as PPG, ECG, EEG, GSR and/or a thermistor.

In a second example, $m_{conf}$ represent an environmental condition and/or a situation of the user that may be considered a confounding factor, such as an indication of whether the user touched at least one of the eyes, an indication of whether the user is engaged in physical activity (and possibly the type and/or extent of the physical activity), temperature, humidity, IR radiation level, and a noise level. Optionally, the one or more values are obtained based on using an accelerometer, a pedometer, a humidity sensor, a miniature radar (such as low-power radar operating in the range between 30 GHz and 3,000 GHz), a miniature active electro-optics distance measurement device (such as a miniature Lidar), an anemometer, an acoustic sensor, and/or a light meter.

In a third example, $m_{conf}$ represent properties describing the user, such as the user's age, gender, marital status, occupation, education level, health conditions, and/or mental health issues that the user may have.

Stress may be thought of as the body's method of reacting to a challenge. Optionally, stress may be considered a physiological reaction to a stressor. Some examples of stressors include mental stressors that may include, but are not limited to, disturbing thoughts, discontent with something, events, situations, individuals, comments, or anything a user may interpret as negative or threatening. Other examples of stressors include physical stressors that may put strain on the body (e.g., very cold/hot temperatures, injury, chronic illness, or pain). In one example, a (high) workload may be considered a stressor. The extent to which a user feels stressed is referred to herein as a "stress level" and being under a certain level of stress may be referred to herein as "experiencing a certain stress level". Depending on the embodiment, a stress level may be expressed via various types of values, such as a binary value (the user is "stressed" or "not stressed", or the user is under "elevated stress" or "not under elevated stress"), a categorical value (e.g., no stress/low stress/medium stress/high stress), and/or a numerical value (e.g., a value on a scale of 0 to 10). In some embodiments, a "stress level" may refer to a "fight or flight" reaction level.

Evaluation of stress typically involves determining an amount of stress a person may be feeling according to some standard scale. There are various approaches known in the literature that may be used for this task. One approach involves identifying various situations the person may be in, which are associated with certain predefined extents of stress (which are empirically derived based on observations). Example of popular approaches include the Holmes and Rahe stress scale, the Perceived Stress Scale, and the Standard Stress Scale (SSS). A common trait of many the various stress scales is that they require a manual evaluation of situations a user undergoes, and do not measure the actual physiological effects of stress.

In some embodiments, the computer may receive an indication of a type of stressor, and utilize the indication to detect the stress level. Optionally, the indication is indicative of a period and/or duration during which the user was affected by the stressor. In one example, the indication is utilized to select a certain threshold value, which is appropriate for the type of stressor, and to which $TH_{ROI1}$ may be compared in order to determine whether the user is experiencing a certain stress level. Optionally, the certain threshold is determined based on thermal measurements of the user when the user reacted to a stressor of the indicated type. In another example, the indication is utilized to select a certain reference time series, which corresponds to the type of stressor, and to which $TH_{ROI1}$ may be compared in order to determine whether the user is experiencing a certain stress level. Optionally, the certain time series is based on thermal measurements of the user taken when the user reacted to a stressor of the indicated type. In yet another example, the computer generates one or more feature values based on the indication, and the one or more feature values are utilized to detect the stress level using a model (in addition to feature values generated based on $TH_{ROI1}$). In still another example, the computer may select a window of time based on the indication, which corresponds to the expected duration of stress induced by the type of stressor indicated in the indication. In this example, in order to detect the stress level of the user, the computer evaluates thermal measurements from among $TH_{ROI1}$ that were taken at a time that falls in the window.

Additional CAMs may be utilized to detect the stress level. The thermal measurements of the additional CAMs, typically denoted $TH_{ROI2}$ below, may be utilized to generate one or more of the feature values that are used along with the machine learning-based model to detect the stress level.

In one embodiment, the system includes a second inward-facing head-mounted thermal camera (CAM2) that takes thermal measurements of an additional ROI on the face ($TH_{ROI2}$), such as the forehead, the nose, and/or a region below the nostrils. The region below the nostrils refer to one or more regions on the upper lip, the mouth, and/or air volume through which the exhale streams from the nose and/or mouth flow, and it's thermal measurements are indicative of the user's breathing.

Given $TH_{ROI2}$, the computer may generate feature values based on $TH_{ROI1}$ and $TH_{ROI2}$ (and possibly other sources of data) and utilizes a model to detect the stress level based on the feature values. Optionally, the model was trained based on previous $TH_{ROI1}$ and $TH_{ROI2}$ taken while the user had at least two different stress levels according to a predetermined stress scale. For example, a first set of previous $TH_{ROI1}$ and $TH_{ROI2}$ taken while the user was under elevated stress, and a second set of previous $TH_{ROI1}$ and $TH_{ROI2}$ taken while the user was not under elevated stress.

In another embodiment, the system further includes second and third CAMs that take thermal measurements of regions on the right and left cheeks, respectively. Optionally, the computer detects the stress level also based on the thermal measurements of the cheeks.

Figure 26:
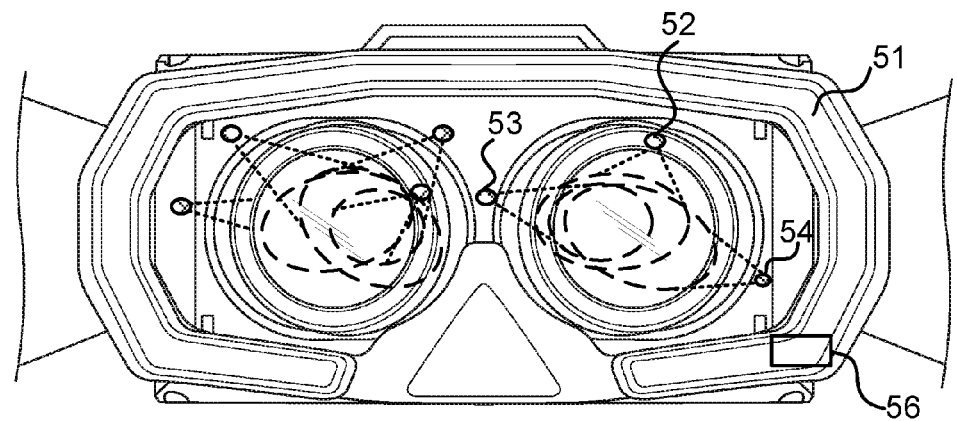
FIG. 26 illustrates an embodiment of an HMS able to measure stress level.

FIG. 26 illustrates one embodiment of an HMS able to measure stress level. The system includes a frame 51, CAMs (52, 53, 54), and a computer 56. CAMs are physically coupled to the frame and take thermal measurements of ROIs on the periorbital areas. Because CAMs are located close to their respective ROIs, they can be small, light-weight, and may be placed in many potential locations having line of sight to their respective ROIs. The computer 56, which may by located on the HMS, worn by the user, and/or remote such as in the cloud, detects the stress level based on changes to temperature of the periorbital areas received from the CAMs.

Due to the asymmetry of blood vessels in human faces and different shapes of human faces, having CAMs pointed at the right and left periorbital areas may enable a more accurate detection of physiological phenomena such as stress, and/or may enable detection of stress that is harder to detect based on measuring only a single periorbital area.

Figure 27:
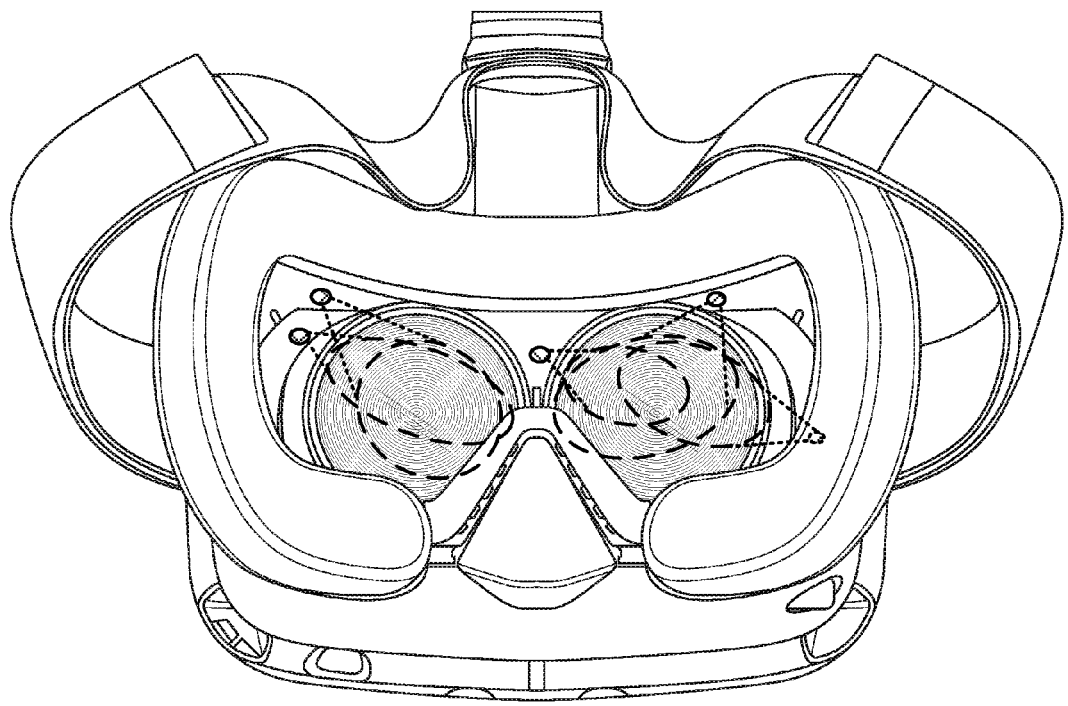
FIG. 27 illustrates examples of asymmetric locations of inward-facing head-mounted thermal cameras (CAMs) that measure the periorbital areas.
Figure 28:
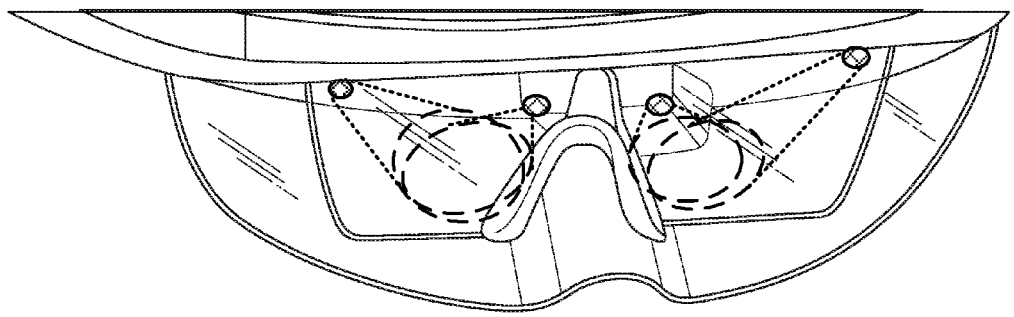
FIG. 28 illustrates an example of symmetric locations of the CAMs that measure the periorbital areas.

While FIG. 26 and FIG. 27 illustrate examples of asymmetric locations of CAMs that measure the right periorbital area relative to the locations of CAMs that measure the left periorbital area, FIG. 28 illustrates an example of symmetric locations of the CAMs that measure the right periorbital area relative to the locations of the CAMs that measure the left periorbital area. In some embodiments, using thermal measurements from both symmetric and asymmetric located CAMs may improve the system's adaptability to different faces having different proportions.

Figure 30A:
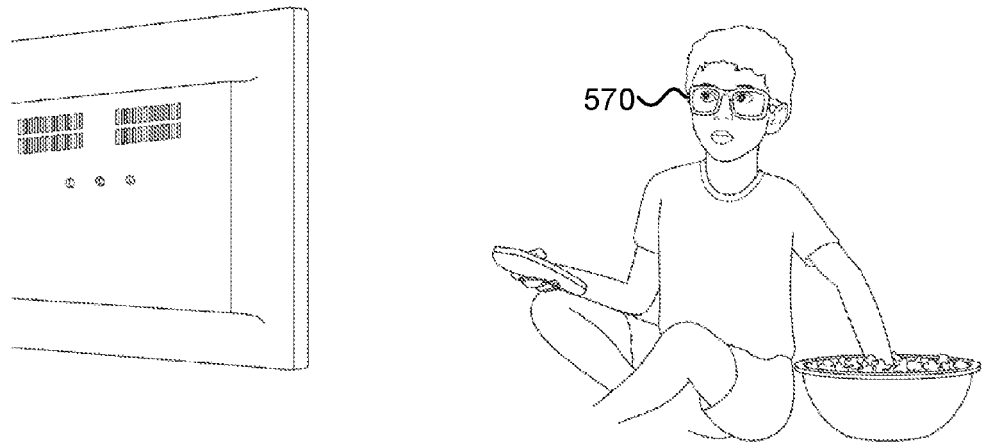
FIG. 30a illustrates a child watching a movie while wearing an eyeglasses frame with at least five CAMs.
Figure 30B:
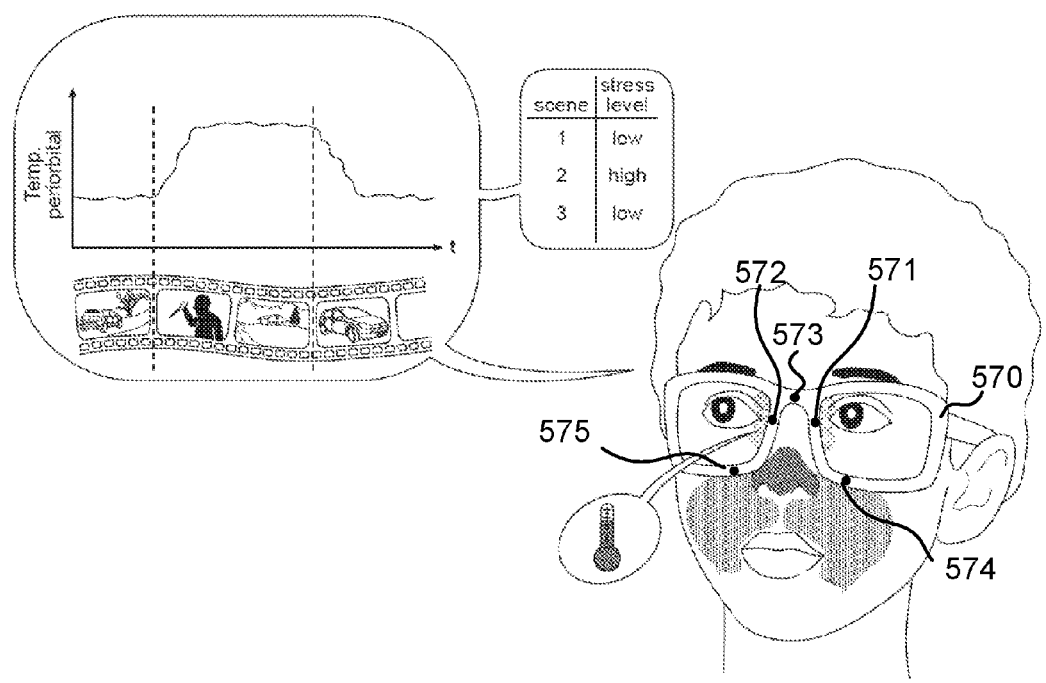
FIG. 30b illustrates generation of a graph of the stress level of the child detected at different times while different movie scenes were viewed.

FIG. 30a and FIG. 30b illustrate one scenario of detecting a user's stress level. FIG. 30a illustrates a child watching a movie while wearing an eyeglasses frame 570 with at least five CAMs. FIG. 30b illustrates the at least five CAMs 571, 572, 573, 574, and 575, which measure the right and left periorbital areas, the nose, and the right and left cheeks, respectively (the different ROIs are designated by different patterns). The figure further illustrates how the system produces a graph of the stress level detected at different times while different movie scenes were viewed.

In one embodiment, the system may include a head-mounted display (HMD) that presents digital content to the user and does not prevent CAM from measuring the ROI. In another embodiment, the system may include an eye tracker to track the user's gaze, and an optical see through HMD that operates in cooperation with the following components: a visible-light camera that captures images of objects the user is looking at, and a computer that matches the objects the user is looking at with the detected stress levels. Optionally, the eye tracker is coupled to a frame worn by the user. In yet another embodiment, the system may include a HMD that presents video comprising objects, and an eye tracker. The computer utilizes data generated by the eye tracker to match the objects the user is looking at with the detected stress levels. It is to be noted that there may be a delay between being affected by a stressor and a manifestation of stress as a reaction, and this delay may be taken into account when determining what objects caused the user stress.

Figure 32:
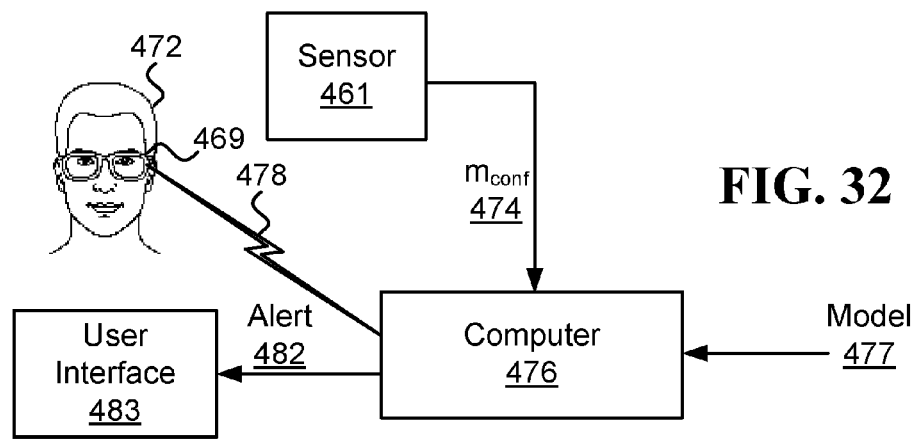
FIG. 32 illustrates an embodiment of a system that includes a user interface, which notifies a user when the stress level of the user reaches a predetermined threshold.

In one embodiment, the system further includes a user interface (UI), such as user interface 483 illustrated in FIG. 32, which notifies the user when the stress level reaches a predetermined threshold. Optionally, the UI notifies the user by an audio indication, a visual indication, and/or a haptic notification. Optionally, the greater the change to the temperature of the periorbital areas, the higher the detected stress level, and the indication is proportional to the stress level. Optionally, the UI also provides the user with encouragement not to engage in certain behavior that causes stress, such as displaying anger, screaming, denigrating others, lying, and/or cheating. In one example, the encouragement may include evidence based on detected stress levels of the user, which indicates that conducting in the certain behavior increases stress. In another example, the encouragement may include reminding the user that the certain behavior is against the user's beliefs and/or the certain behavior is contrary to the user's goals, interests, and/or resolutions.

In one embodiment, a system configured to alert about stress includes at least CAM1 and CAM2 located at least 0.5 cm to the right and to the left of the vertical symmetry axis that divides the user's face, respectively. CAM1 and CAM2 take thermal measurements of regions on the periorbital areas of the right and left eyes ($TH_{ROI1}$ and $TH_{ROI2}$, respectively) of the user. UI 483 provides an alert about a stress level reaching a threshold. Optionally, the system includes a frame that is worn on the user's head, CAM1 and CAM2 are physically coupled to the frame, weighs below 10 g each, and located less than 15 cm from the user's face. Optionally, the system includes a transmitter that may be used to transmit $TH_{ROI1}$ and $TH_{ROI2}$ to a computer that detects the stress level based on $TH_{ROI1}$ and $TH_{ROI2}$. Optionally, responsive to detecting a stress level that reaches a threshold, the computer commands the user interface to provide the alert. For example, the computer may send a signal to a smartphone app, and/or to a software agent that has control of the user interface, to provide the alert.

One embodiment of a method for alerting about stress includes at least the following steps: In Step 1, taking thermal measurements of regions on the periorbital areas of the right and left eyes ($TH_{ROI1}$ and $TH_{ROI2}$, respectively) of a user utilizing first and second CAMs worn on the user's head and located at least 0.5 cm to the right and to the left of the vertical symmetry axis that divides the user's face, respectively. And in Step 2, alerting about a stress level that is detected based on $TH_{ROI1}$ and $TH_{ROI2}$. Optionally, the alert about the allergic reaction is provided as text, image, sound, and/or haptic feedback.

Optionally, the method further includes generating feature values based on $TH_{ROI1}$ and $TH_{ROI2}$, and using a model for detecting the stress level based on the feature values. The model was trained based on previous $TH_{ROI1}$ and $TH_{ROI2}$ of the user, taken during different days, which include: a first set of measurements taken while the user had a first stress level according to a predetermined stress scale, and a second set of measurements taken while the user had a second stress level according to the predetermined stress scale.

Optionally, the method further includes generating feature values based on $TH_{ROI1}$ and $TH_{ROI2}$, and using a model for detecting the stress level based on the feature values. The model was trained based on previous $TH_{ROI1}$ and $TH_{ROI2}$ of one or more users, taken during different days, which comprise: a first set of measurements taken while the one or more users had a first stress level according to a predetermined stress scale, and a second set of measurements taken while the one or more users had a second stress level according to the predetermined stress scale.

The above steps of generating the feature values and utilizing the model may be performed multiple times throughout the period of the different days during which $TH_{ROI1}$ and $TH_{ROI2}$ were taken, each time utilizing a subset of $TH_{ROI1}$ and $TH_{ROI2}$ taken during a different window of a certain length. In these embodiments, the alerting in Step 2 may be done at a certain time for which a certain stress level is detected (which warrants an alert).

Figure 29:
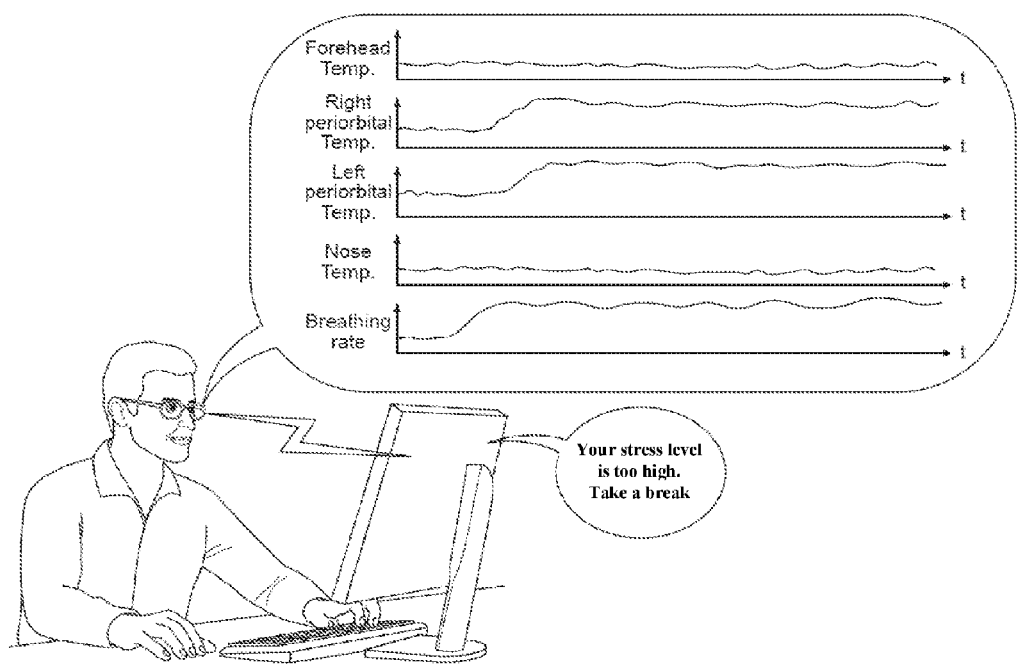
FIG. 29 illustrates a scenario in which a system suggests to the user to take a break in order to reduce the stress level.

FIG. 29 illustrates a scenario in which a system (which measures the forehead, right and left periorbital areas, nose, and below the nostrils) suggests to the user to take a break in order to reduce the stress level of the user. The system may suggest the user to partake in at least one of the following activities when the stress level reaches a first threshold: practice pranayama, physical exercise, listen to brainwave entrainment, and listen to positive loving statements. Optionally, the computer suggests to the user to stop the activity when the stress level gets below a second threshold. Optionally, the system shows the user video comprising objects, and the detected stress level associated with the objects.

Figure 31:
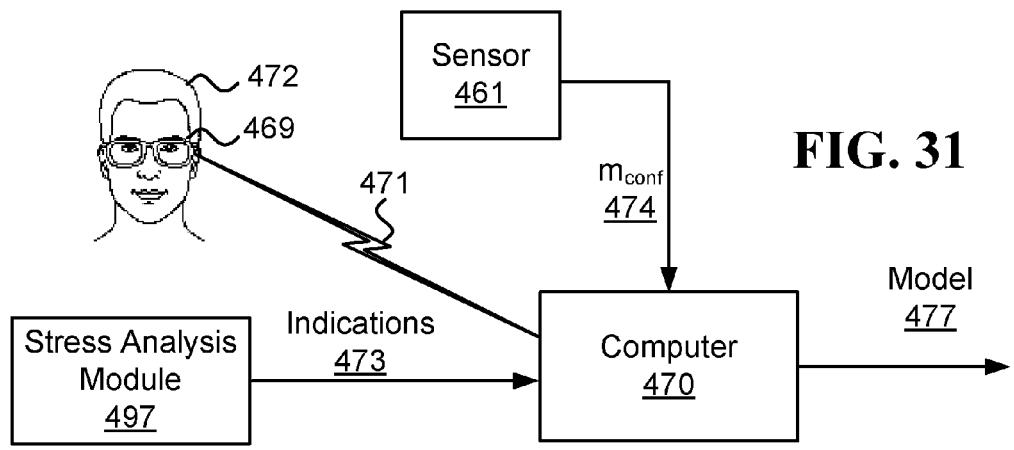
FIG. 31 illustrates an embodiment of a system that generates a personalized model for detecting stress based on thermal measurements of the face.

FIG. 31 illustrates one embodiment of a system configured to generate a personalized model for detecting stress based on thermal measurements of the face. The system includes a frame, first and second CAMs, and a computer 470. The first and second CAMs take thermal measurements 471 of regions on the periorbital areas of the right and left eyes ($TH_{ROI1}$ and $TH_{ROI2}$, respectively) of the user 472.

The computer 470 generates samples based on data comprising: (i) $TH_{ROI1}$ and $TH_{ROI2}$ 471, and (ii) indications 473 corresponding to different times, which are indicative of stress levels of the user at the different times. Optionally, each sample comprises: (i) feature values generated values based on $TH_{ROI1}$ and $TH_{ROI2}$ taken during a certain period, and (ii) a label indicative of a stress level of the user during the certain period. Optionally, at least one of the feature values in a sample may be generated based on other sources of information such as physiological measurements of the user 472 and/or measurements of the environment in which the user 472 was in when while $TH_{ROI1}$ and $TH_{ROI2}$ 471 were taken. Optionally, the stress levels indicated in the indications 473 correspond to levels of a known stress level scale. The computer 470 trains a model 477 based on the samples. Optionally, the computer 470 also provides the model 477 to be used by a system that detects stress based on $TH_{ROI1}$ and $TH_{ROI2}$.

The indications 473 may be generated in different ways, in different embodiments. One or more of the indications 473 may be (i) generated by an entity that observes the user 472, such as a human observer or a software program (e.g., a software agent operating on behalf of the user 472), (ii) provided by the user 472, such as via a smartphone app by pressing a certain button on a screen of a smartphone, and/or by speech that is interpreted by a software agent and/or a program with speech analysis capabilities, (iii) determined based on analysis of behavior of the user 472, such as by analyzing measurements of a camera and/or a microphone that indicate that the user 472 is experiencing a certain stress level, and (iv) determined based on physiological signals of the user 472 that are not thermal measurements of one or more ROIs on the face, such as measurements of the user's heart rate and/or brainwave activity.

Optional stress analysis module 497 receives descriptions of events corresponding to when at least some of $TH_{ROI1}$ and $TH_{ROI2}$ 471 were taken, and generates one or more of the indications 473 based on analyzing the descriptions. The stress analysis module 497 is implemented by the computer 470 or another computer. Optionally, all of the indications 473 are generated by the stress analysis module 497. Optionally, the stress analysis module 497 may be a module of a software agent operating on behalf of the user 472. The descriptions received by the stress analysis module 497 may include various forms of information. In one example, the descriptions include content of a communication of the user 472, and the stress analysis module 497 utilizes semantic analysis in order to determine whether the communication is indicative a stressful event for the user 472 (e.g., the communication is indicative of something going wrong at work). Optionally, the stress analysis module 497 utilizes a machine learning-based model to calculate based on features derived from the communication, a predicted stress level for the user 472. In another example, the stress analysis module 497 receives images of an event, such as images taken by an outward-facing head-mounted visible-light camera, utilizes image analysis to determine whether the event corresponds to a stressful event, and utilizes a machine learning-based model to calculate the predicted stress based on features derived from the images.

The model is trained on samples comprising feature values based on $TH_{ROI1}$ and $TH_{ROI2}$, and additional feature values described in the following examples:

In a first example, the additional feature values include additional thermal measurements, taken with another CAM, of an ROI that includes the nasal and/or mouth regions.

In a second example, the additional feature values are indicative of one or more of the following signals of the user 472: a heart rate, heart rate variability, brainwave activity, galvanic skin response, muscle activity, and an extent of movement.

In a third example, the additional feature values are measurements ($m_{conf}$ 474) of the user 472 and/or of the environment in which the user 472 was in while $TH_{ROI1}$ and $TH_{ROI2}$ 471 were taken. Optionally, $m_{conf}$ 474 are taken by a sensor 461, which may be physically coupled to the frame. In another example, the sensor 461 is coupled to a device carried by the user, such as a smartphone, a smartwatch, and/or smart clothing (e.g., clothing embedded with sensors that can measure the user and/or the environment). In yet another example, the sensor 461 may be an external sensor that is not carried by the user. Optionally, the computer 470 is generates, based on $m_{conf}$ 474, one or more feature values of at least some of the samples. $m_{conf}$ 474 are indicative of an extent to which one or more confounding factors occurred while $TH_{ROI1}$ and $TH_{ROI2}$ 471 were taken.

In one embodiment, the sensor 461 is a visible-light camera physically coupled to the frame, which takes images of a region on the face of the user 472, which includes at least 25% of the $ROI_1$ and/or $ROI_2$. Optionally, the confounding factor in this embodiment involves inflammation of the skin, skin blemishes, food residues on the face, talking, eating, drinking, and/or touching the face. In another embodiment, the sensor 461 includes a movement sensor that measures a movement of the user 472. Optionally, the confounding factor in this embodiment involves the user 472 walking, running, exercising, bending over, and/or getting up from a sitting or lying position. In yet another embodiment, the sensor 461 measures at least one of the following environmental parameters: a temperature of the environment, a humidity level of the environment, a noise level of the environment, air quality in the environment, a wind speed in the environment, an extent of precipitation in the environment, and an infrared radiation level in the environment.

In some embodiments, the samples used to train the model 477 include samples that were generated based on $TH_{ROI1}$ and $TH_{ROI2}$ of the user 472 taken while the user 472 had different stress levels. In one embodiment, one or more samples that were generated based on $TH_{ROI1}$ and $TH_{ROI2}$ of the user 472 taken while a stress level of the user 472 reached a threshold. Optionally, the stress level is evaluated using one or more known stress level scales. Optionally, a user whose stress level reaches the threshold is considered "stressed". Additionally, in this embodiment, the samples include one or more samples that were generated based $TH_{ROI1}$ and $TH_{ROI2}$ of the user 472, which were taken while a stress level of the user 472 did not reach the threshold. Optionally, a user whose stress level does not reach the threshold is not considered "stressed". Thus, the samples may be utilized to train a model that can help distinguish between cases in which $TH_{ROI1}$ and $TH_{ROI2}$ of the user 472 are taken while the user 472 is stressed (and/or the user 472 has a certain stress level), and cases in which $TH_{ROI1}$ and $TH_{ROI2}$ of the user 472 are taken while the user 472 is not stressed (and/or the user 472 does not have a certain stress level).

The samples used to train the model 477 may include samples generated based on measurements taken while user 472 was in different environments. In one example, the samples comprise first and second samples that are based on $TH_{ROI1}$ and $TH_{ROI2}$ of the user 472 taken during first and second periods, respectively. Optionally, different environmental conditions prevailed during the first and second periods, which involved one or more of the following differences: (i) the temperature of the environment in which the user 472 was during the first period was at least 10° C. higher than the temperature of the environment in which the user 472 was during the second period; (ii) the humidity level in the environment in which the user 472 was during the first period was at least 30% higher than the humidity level in the environment in which the user 472 was during the second period; and (iii) the user 472 was exposed to rain, hail, and/or snow during the first period and the user was not exposed to any of rain, hail, and snow during the second period.

Additionally or alternatively, the samples utilized to train the model 477 may include samples generated based on measurements taken while the user 472 was in various situations. In one example, the samples comprise first and second samples that are based on $TH_{ROI1}$ and $TH_{ROI2}$ of the user 472 taken during first and second periods, respectively. Optionally, the user 472 was in different situations during the first and second periods, which involved one or more of the following differences: (i) the user 472 was sedentary during the first period, while the user 472 was walking, running, and/or biking during the second period; and (ii) the user 472 was indoors during the first period, while the user 472 was outdoors during the second.

Additionally or alternatively, the samples utilized to train the model 477 may be based on $TH_{ROI1}$ and $TH_{ROI2}$ taken during different days and/or over a long period, such as more than a week, more than a month, or more than a year.

Training the model 477 may involve one or more of the various computational approaches mentioned in this disclosure for training a model used to detect a physiological response. In one example, training the model 477 may involve selecting, based on the samples, a threshold; if a certain feature value reaches the threshold then a certain level of stress of the user is detected. In another example, the computer 470 utilizes a machine learning-based training algorithm to train the model 477 based on the samples. Optionally, the model comprises parameters of at least one of the following models: a regression model, a model utilized by a neural network, a nearest neighbor model, a model for a support vector machine for regression, and a model of a decision tree.

In some embodiments, the computer 470 may utilize deep learning algorithms to train the model 477. In one example, the model 477 may include parameters describing multiple hidden layers of a neural network. In one embodiment, when $TH_{ROI1}$ and $TH_{ROI2}$ include measurements of multiple pixels, such as when CAM includes a FPA, the model 477 may include parameters of a convolution neural network (CNN). In one example, a CNN may be utilized to identify certain patterns in the thermal images, such as patterns of temperatures on the forehead that may be indicative of a certain physiological response (e.g., a headache, stress, or anger). In another embodiment, detecting the stress level may be done based on multiple, possibly successive, measurements. For example, stress may involve a progression of a state of the user (e.g., a gradual warming of certain areas of the forehead). In such cases, detecting the stress level may involve retaining state information that is based on previous measurements. Optionally, the model 477 may include parameters that describe an architecture that supports such a capability. In one example, the model 477 may include parameters of a recurrent neural network (RNN), which is a connectionist model that captures the dynamics of sequences of samples via cycles in the network's nodes. This enables RNNs to retain a state that can represent information from an arbitrarily long context window. In one example, the RNN may be implemented using a long short-term memory (LSTM) architecture. In another example, the RNN may be implemented using a bidirectional recurrent neural network architecture (BRNN).

In one embodiment, training the model 477 involves altering parameters of another model, which is generated based on $TH_{ROI1}$ and $TH_{ROI2}$ of one or more other users. For example, the computer 470 may utilize the other model as an initial model. As the samples are acquired from measurements of the user 472, the computer 470 may update parameters of the initial model based on the samples. Thus, this process may be considered personalizing a general model according to measurements of the user 472.

Once the model 477 is generated, it may be utilized to detect stress of the user 472 based on other $TH_{ROI1}$ and $TH_{ROI2}$ of the user 472, which are not among $TH_{ROI1}$ and $TH_{ROI2}$ 471 that were used for training the model 477. Such utilization of the model 477 is illustrated in FIG. 32, which illustrates one embodiment of a system configured to perform personalized detection of stress based on thermal measurements of the periorbital area. One embodiment of the illustrated system includes a frame 469, first and second CAMs, and a computer 476.

The computer 476 is configured to: generate feature values based on $TH_{ROI1}$ and $TH_{ROI2}$ 478 and utilize the model 477 to detect the stress level of the user 472 based on the feature values. Optionally, the model 477 was trained based on previous $TH_{ROI1}$ and $TH_{ROI2}$ of the user 472 (e.g., $TH_{ROI1}$ and $TH_{ROI2}$ 471), which were taken during different days. The feature values generated based on $TH_{ROI1}$ and $TH_{ROI2}$ 478 are similar in their nature to the feature values generated based on $TH_{ROI1}$ and $TH_{ROI2}$ 471, which were discussed in more detail above. Optionally, the computer 476 and the computer 470 may utilize the same modules and/or procedures to generate feature values based on $TH_{ROI1}$ and $TH_{ROI2}$ (and possibly other data). Optionally, the computer 476 receives measurements $m_{conf}$ 474 indica-tive of an extent to which a confounding factor occurred while $TH_{ROI1}$ and $TH_{ROI2}$ 478 were taken, as discussed above.

Since the model 477 is personalized for the user 472, when such a model is trained for different users, it may lead to different detections of stress, even when provided with similar $TH_{ROI1}$ and $TH_{ROI2}$ of the users. In one example, first and second models are generated based on previous $TH_{ROI1}$ and $TH_{ROI2}$ of first and second different users, respectively. Responsive to utilizing the first model, a first value is detected based on first feature values generated based on $TH_{ROI1}$ and $TH_{ROI2}$ of the first user, which is indicative of a first stress level. Responsive to utilizing the second model, a second value is detected based on second feature values generated based on $TH_{ROI1}$ and $TH_{ROI2}$ of the second user, which is indicative of a second stress level. In this example, $TH_{ROI1}$ and $TH_{ROI2}$ of the first user indicate a greater temperature change at the periorbital areas of the first user compared to the change at the periorbital areas of the second user indicated by $TH_{ROI1}$ and $TH_{ROI2}$ of the second user. However, in this example, the first stress level is lower than the second stress level.

Some aspects of this disclosure involve monitoring a user over time with CAM that takes thermal measurements of a region on a periorbital area ($TH_{ROI1}$) of the user. One application for which $TH_{ROI1}$ may be useful is to detect the stress level of the user. Analysis of these detections combined with information regarding factors that affected the user at different times, which may be considered potential stressors, can reveal which of the factors may be stressor that increase the stress level of the user.

Some examples of factors that may be considered potential stressors for certain users include being in certain locations, interacting with certain entities, partaking in certain activities, or being exposed to certain content. Having knowledge of which potential stressor are likely to actually be stressors for a certain user can help that user avoid the stressors and/or take early measures to alleviate the effects of the stress they cause.

Figure 33:
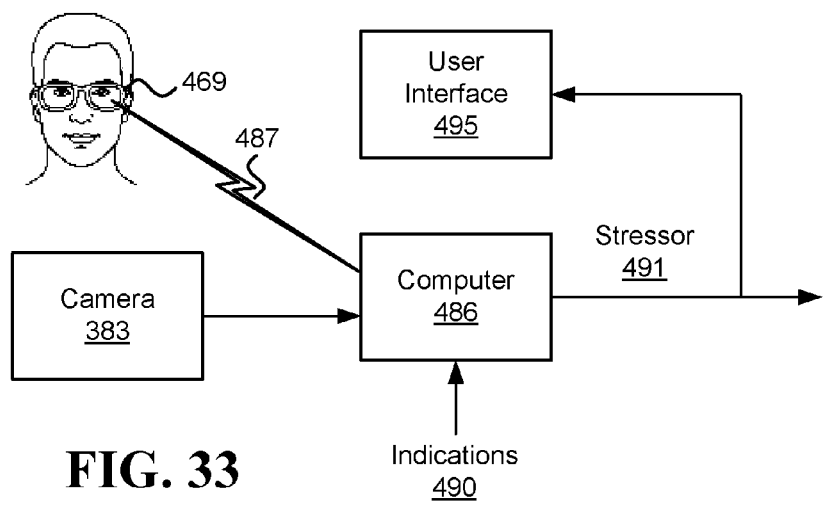
FIG. 33 illustrates an embodiment of a system that selects a stressor.

FIG. 33 illustrates one embodiment of a system configured to select a stressor. The system includes at least a computer 486 and CAM. The system may optionally include a frame 469, a camera 383, and/or a UI 495. In one example, CAM takes thermal measurements of the periorbital area of the right eye, and an additional CAM (CAM2) takes thermal measurements of a region on the periorbital area of the left eye ($TH_{ROI2}$) of the user.

In one embodiment, computer 486 calculates, based on the thermal measurements 487 (e.g., $TH_{ROI1}$ and $TH_{ROI2}$), values that are indicative of stress levels of the user at different times (i.e., detect the stress levels of the user at the different times). Optionally, $TH_{ROI1}$ and $TH_{ROI2}$ include thermal measurements taken while the user had at least two different stress levels according to a predetermined stress scale. Optionally, the thermal measurements 487 comprise thermal measurements taken during different days.

In some embodiments, the system that selects a stressor may include additional CAMs that take thermal measurements of one or more regions on the user's forehead, nose, and/or below the nostrils. Optionally, thermal measurements taken by the additional CAMs are utilized by the computer 486 when calculating the user's stress level.

Furthermore, the computer 486 may receive indications 490 of factors that affected the user at various times, which may be considered potential stressors. The computer 486 also selects a stressor 491, from among the potential stressors, based on the indications 490 and the values that are indicative of stress levels of the user at different times. Optionally, each of the indications 490 is indicative of a time during which the user was exposed to a potential stressor. Additionally or alternatively, each of the indications 490 may be indicative of a time during which the user was affected by a potential stressor. In some embodiments, at any given time, the user may be exposed to more than one of the potential stressors. Thus, in some embodiments, at least some of the thermal measurements 487, and optionally all of the thermal measurements 487, were taken while the user was exposed to two or more potential stressors.

In one embodiment, the indications 490 include a list of periods of time during which various potential stressors affected the user. Optionally, the indications 490 are provided via a data structure and/or a queryable system that provides information for different points in time about which of the potential stressors affected the user at the points in time. There are various types of potential stressors that may be indicated by the indications 490.

In one embodiment, one or more of the potential stressors may relate to various locations the user was at (e.g., work, school, doctor's office, in-laws house, etc.) and/or to various activities the user partakes in (e.g., driving, public speaking, operating machinery, caring for children, choosing clothes to wear, etc.)

In another embodiment, one or more of the potential stressors may relate to entities with which the user interacts. For example, an entity may be a certain person, a person with a certain role (e.g., a teacher, a police officer, a doctor, etc.), a certain software agent, and/or an avatar (representing a person or a software agent).

In yet another embodiment, one or more of the potential stressors may relate to situations in which the user is in, which can increase stress. For example, a situation may be being unemployed, having financial difficulties, being separated after being in a relationship with another person, being alone, or awaiting an important event (e.g., an exam, a job interview, or results of an important medical test). In another example, a situation may relate to a physical condition of the user, such as being sick or suffering from a certain chronic disease. Optionally, when the situations described above are applicable to another person who the user cares about (e.g., a spouse, child, parent, or close friend), then those situations, which relate to the other person, may be considered potential stressors that can lead to stress in the user.

In still another embodiment, one or more of the potential stressors may relate to the user's behavior. For example, behaving in a way that is argumentative, manipulative, deceptive, and/or untruthful may increase the stress level.

When a user is affected by one or more potential stressors, in some embodiments, the stress level of the user may depend on quantitative aspects of the potential stressors. In some examples, the degree to which a potential stressor affects the user's stress level may depend on the amount of time the potential stressor affected the user (e.g., the duration the user spent at a certain location) and/or the magnitude of the potential stressor (e.g., the extent to which an argument was heated—which may be expressed by the level of noise in peoples shouting). In some embodiments, the indications 490 include values that quantify how much at least some of the potential stressors affected the user.

The stressor 491 is a potential stressor that is correlated with an increase in the stress level of the user. Additionally, in some embodiments, the stressor 491 may be a potential stressor that may be considered a direct cause of the increase in the stress level of the user. When considering how being affected by the potential stressors relates to the stress level of the user, an effect of the stressor 491 is higher than effects of most of the potential stressors.

The effect of a potential stressor may be considered a measure of how much the potential stressor influences the stress level the user. This can range from no influence to a profound influence. More specifically, in one embodiment, the effect of a potential stressor is a value indicative of the average extent of change to the stress level of the user at a time $t+\Delta$ after being affected by the potential stressor at time t. Here, $\Delta$ corresponds to the typical time it may take the stress to manifest itself in the user after being affected by the potential stressor. This time may range from a short period e.g., several seconds or minutes, to hours.

There are various ways in which the computer 486 may select, based on the indications 490 and the thermal measurements 487, the stressor 491 from among the potential stressors being considered.

In some embodiments, the computer 486 performs a direct analysis of the effect of each of the potential stressors in order to identify which ones have a large effect on the user. Optionally, the effect of each potential stressor is indicative of the extent to which it increases the stress level of the user. Optionally, the effect of each potential stressor is calculated by determining, based on the indications 490, times at which the user was affected by the potential stressor, and observing the stress level of the user at one or more times that are up to a certain period $\Delta$ later (where $\Delta$ depends on the user and the type of stressor). In one example, $\Delta$ is ten seconds, thirty seconds, or one minute. In another example, $\Delta$ is one minute, ten minutes, or one hour.

In one embodiment, a stress level (or change to the stress level) following being affected by a potential stressor is the maximum stress level that is detected from the time t the user was affected by the potential stressor until the time $t+\Delta$. In another example, the stress level (or change to the stress level) following being affected by the potential stressor is the extent of the stress level and/or change to the stress level that is detected at a time $t+\Delta$ (when the user was affected by the potential stressor at time t). Optionally, the extent may be normalized based on a quantitative value representing how much the user was affected by the potential stressor. Optionally, the stress level may be normalized with respect to a stress level detected prior to being affected by the potential stressor.

Following a calculation of the effects of the potential stressors, in one embodiment, the computer 486 selects the stressor 491 from among the potential stressors. Optionally, the stressor 491 is a potential stressor that has a maximal effect (i.e., there is no other potential stressor that has a higher effect). Optionally, the stressor 491 is a potential stressor that has an effect that reaches a threshold, while the effects of most of the potential stressors do not reach the threshold.

In one embodiment, in order to increase confidence in the selection of the stressor, the stressor 491 is selected based on at least a certain number of times in which the user was affected by the stressor 491. For example, the certain number may be at least 3 or 10 different times. Thus, in this embodiment, potential stressors that did not affect the user at least the certain number of times are not selected.

In some embodiments, the computer 486 generates a machine learning-based model based on the indications 490 and the values indicative of the stress levels of the user, and selects the stressor 491 based on an analysis of the model. Optionally, the computer 486 generates samples used to train the model. The samples used to train the model may correspond to different times, with each sample corresponding to a time t+Δ including feature values and a label indicative of the stress level of the user at the time t+Δ. Each sample may be considered to represent a snapshot of potential stressors that affected the user during a certain period, and a label that is indicative of the stress level of the user following being affected by those potential stressors. Given multiple such samples, a machine learning training algorithm can be utilized to train a model for a predictor module that can predict the stress level at a certain time based on feature values that describe potential stressors that affected the user during a certain period of time leading up to the certain time. For example, if the model is a regression model, the predictor module may perform a dot product multiplication between a vector of regression coefficients (from the model) and a vector of the feature values in order to calculate a value corresponding to the predicted stress level of the user at the certain time.

When such a predictor module is capable of predicting stress level of the user based on the feature values described above, this may mean that the model captures, at least to some extent, the effects of at least some of the potential stressors on the stress level of the user.

Training the model based on the samples described above may involve utilizing one or more of various training algorithms. Some examples of models that may be generated in order to be utilized by the predictor module described above include the following models: a regression model (e.g., a regression model), a naïve Bayes model, a Bayes network, a support vector machine for regression, a decision tree, and a neural network model, to name a few possibilities. There are various training algorithms known in the art for generating these models and other models with similar properties.

The predictor module may be provided multiple inputs representing the potential stressors that affected the user at different points of time, and have a capability to store state information of previous inputs corresponding to earlier times when it comes to predict the stress level of the user at a certain time. For example, the predictor module may be based on a recurrent neural network.

Once the model is trained, in some embodiments, it is analyzed by the computer 486 in order to determine the effects of one or more of the stressors on the stress level of the user. Depending on the type of model that was trained, this analysis may be performed in different ways.

In one embodiment, the computer 486 performs the analysis of the model by evaluating parameters of the model that correspond to the potential stressors. Optionally, the computer 486 selects as the stressor 491 a certain potential stressor that has a corresponding parameter that is indicative of an effect that reaches a threshold while effects indicated in parameters corresponding to most of the stressors do not reach the threshold. In one example, the model may be a linear regression model in which each potential stressor corresponds to a regression variable. In this example, a magnitude of a value of a regression coefficient may be indicative of the extent of the effect of its corresponding potential stressor. In another example, the model may be a naïve Bayes model in which various classes correspond to stress levels (e.g., a binary classification model that is used to classify a vector of feature values to classes corresponding to "stressed" vs. "not stressed"). In this example, each feature value may correspond to a potential stressor, and the class conditional probabilities in the model are indicative of the effect of each of the potential stressors on the user.

In another embodiment, the computer 486 performs an analysis of the model, which may be characterized as "black box" analysis. In this approach, the predictor module is provided with various inputs that correspond to different potential stressors that affect the user, and calculates, based on the inputs and the model, various predicted stress levels of the user. The various inputs can be used to independently and/or individually increase the extent to which each of the potential stressors affects the user. This type of the model probing can help identify certain potential stressors that display an increase in the predicted stress level, which corresponds to an increase in the extent to which the potential stressors affect the user (according to the model). Optionally, the stressor 491 is a potential stressor for which a positive correlation is observed between increasing the extent to which the potential stressor affects that user, and the predicted stress level of the user. Optionally, the stressor 491 is selected from among the potential stressors, responsive to identifying that: (i) based on a first subset of the various predicted stress levels of the user, an effect of the stressor 491 reaches a threshold, and (ii) based on a second subset of the various predicted stress levels of the user, effects of most of the potential stressors do not reach the threshold.

The indications 490 may be received from various sources. In one embodiment, the user may provide at least some of the indications 490 (e.g., by inputting data via an app and/or providing vocal annotations that are interpreted by a speech analysis software). In other embodiments, at least some of the indications 490 are provided by analysis of one or more sources of data. Optionally, the computer 486 generates one or more of the indications 490 based on an analysis of data obtained from the one or more sources. The following four examples, discussed herein in relation to allergy, are also relevant as examples of sources of data that may be utilized to identify potential stressors that affected the user at different times: (i) a camera 383 captures images of the surroundings of the user, (ii) sensors such as microphones, accelerometers, thermometers, pressure sensors, and/or barometers may be used to identify potential stressors by identifying what the user is doing and/or under what conditions, (iii) measurements of the environment that user is in, and (iv) IoT devices, communications of the user, calendar, and/or billing information may provide information that may be used in some embodiments to identify potential stressors.

Knowledge of the stressor 491 may be utilized for various purposes. Optionally, the knowledge of the stressor 491 is utilized by a software agent operating on behalf of the user in order to better serve the user. In some embodiments, information about the stressor 491 is provided to the user via a UI 495, such as a smartphone, HMD, and/or an earphone).

UI 495 may be utilized on a day-to-day basis to warn the user when the stressor 491 is detected. For example, the computer 486 may provide real-time indications of potential stressors. Upon detecting that those potential stressors include the stressor 491, the UI notifies the user about the stressor in order for the user to take action, such as reducing exposure to the stressor (e.g., by leaving a certain location or ceasing a certain activity) and/or performing actions aimed at reducing stress (e.g., a breathing exercises).

In one embodiment, a software agent identifies that the user is going to be affected by the stressor 491 (e.g., by analyzing the user's calendar schedule and/or communications), and suggests the user, via UI 495, to perform various exercises (e.g., breathing exercises) and/or prepare himself for the stressor 491 in order to reduce its effect.

With little modifications, the system illustrated in FIG. 33 may be utilized to detect a calming factor that reduces the user's stress, rather than one that increases it. In particular, instead of selecting a stressor that has a large effect (or maximal effect) on the user, a factor that has a large negative effect on the stress level may be selected. Optionally, in the event that a high stress level of the user is detected, the calming factor may be suggested to the user (to reduce the user's stress level).

The following is a description of steps involved in one embodiment of a method for selecting a stressor. The steps described below may be used by systems modeled according to FIG. 33, and may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform operations of the method. In one embodiment, the method for alerting about stress includes at least the following steps:

In Step 1, taking, utilizing a CAM, thermal measurements of a region on a periorbital area ($TH_{ROI1}$) of a user who wears CAM. Optionally, the region on the periorbital area is a region of the periorbital area of the right eye, and this step also involves taking, utilizing a second inward-facing head-mounted thermal camera (CAM2), thermal measurements of a region on the periorbital area of the left eye ($TH_{ROI2}$).

In Step 2, detecting extents of stress based on $TH_{ROI1}$. Optionally, detecting the extents may be done utilizing the computer, as discussed above. Optionally, the extents are also detected based on $TH_{ROI2}$ (and/or other thermal measurements mentioned below).

In Step 3, receiving indications of times during which the user was exposed to potential stressors.

And in Step 4, selecting the stressor, from among the potential stressors, based on the indications and the extents. Optionally, during most of the time the user was affected by the stressor, an effect of the stressor, as manifested via changes to $TH_{ROI1}$, was higher than effects of most of the potential stressors.

In one embodiment, the method may optionally include a step of taking images of the surroundings of the user and generating at least some of the indications based on analysis of the images. Optionally, the images are taken with the camera 383, as discussed above.

In one embodiment, selecting the stressor is done by generating a machine learning-based model based on the indications and extents, and selecting the stressor based on an analysis of the model. In one example, performing the analysis of the model involves evaluating parameters of the model that correspond to the potential stressors. In this example, a certain potential stressor is selected as a stress. The certain potential stressor has a corresponding parameter in the model that is indicative of an effect that reaches a threshold, while effects indicated in parameters corresponding to most of the other potential stressors do not reach the threshold. In another example, performing the analysis of the model involves: (i) providing a predictor module with various inputs that correspond to different potential stressors that affect the user; (ii) calculating, based on the inputs and the model, various predicted stress levels; (iii) determining, based on the various predicted stress levels, effects of the potential stressors; and (iv) selecting the stressor based on the effects. In this example, the effect of the stressor reaches a threshold, while effects of most of the other potential stressors do not reach the threshold.

Normally, the lens plane and the sensor plane of a camera are parallel, and the plane of focus (PoF) is parallel to the lens and sensor planes. If a planar object is also parallel to the sensor plane, it can coincide with the PoF, and the entire object can be captured sharply. If the lens plane is tilted (not parallel) relative to the sensor plane, it will be in focus along a line where it intersects the PoF. The Scheimpflug principle is a known geometric rule that describes the orientation of the plane of focus of a camera when the lens plane is tilted relative to the sensor plane.

Figure 20A:
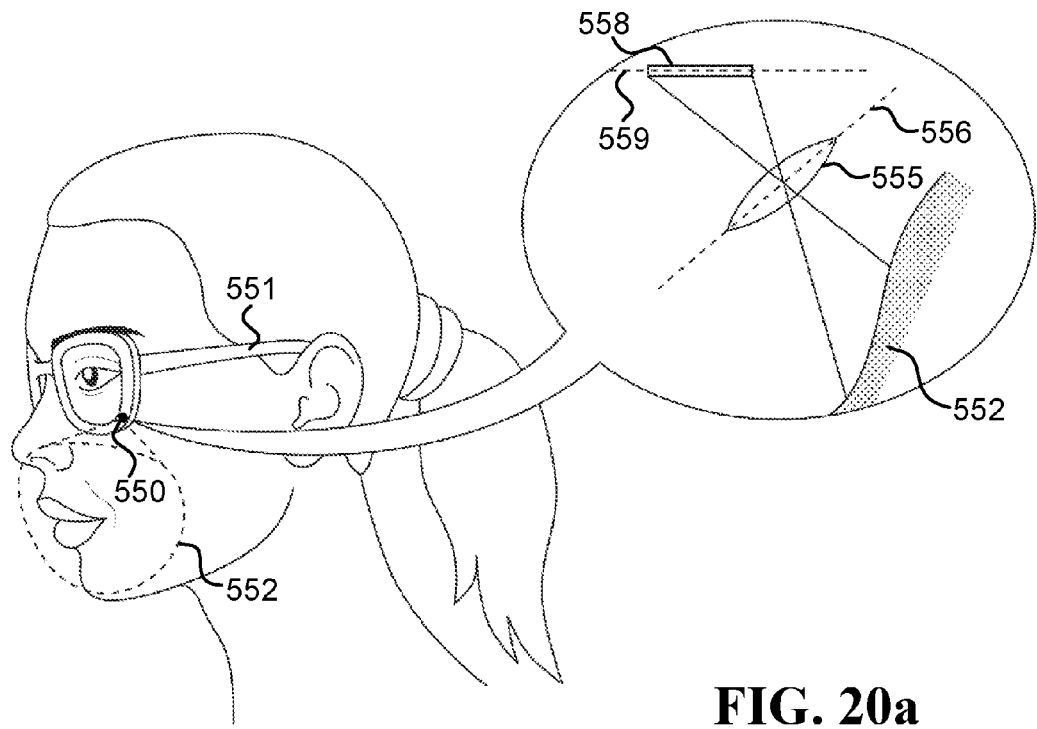
FIG. 20a is a schematic illustration of an inward-facing head-mounted camera embedded in an eyeglasses frame, which utilizes the Scheimpflug principle.

FIG. 20a is a schematic illustration of an inward-facing head-mounted camera 550 embedded in an eyeglasses frame 551, which utilizes the Scheimpflug principle to improve the sharpness of the image taken by the camera 550. The camera 550 includes a sensor 558 and a lens 555. The tilt of the lens 555 relative to sensor 558, which may also be considered as the angle between the lens plane 555 and the sensor plane 559, is determined according to the expected position of the camera 550 relative to the ROI 552 when the user wears the eyeglasses. For a refractive optical lens, the "lens plane" 556 refers to a plane that is perpendicular to the optical axis of the lens 555. Herein, the singular also includes the plural, and the term "lens" refers to one or more lenses. When "lens" refers to multiple lenses (which is usually the case in most modern cameras having a lens module with multiple lenses), then the "lens plane" refers to a plane that is perpendicular to the optical axis of the lens module.

Figure 20B:
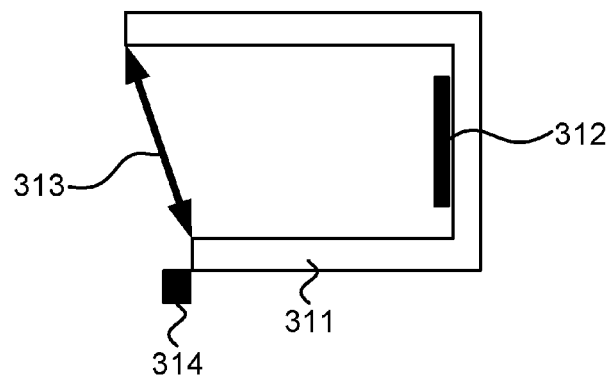
FIG. 20b is a schematic illustration of a camera that is able to change the relative tilt between its lens and sensor planes according to the Scheimpflug principle.

The Scheimpflug principle may be used for both thermal cameras (based on lenses and sensors for wavelengths longer than 2500 nm) and visible-light and/or near-IR cameras (based on lenses and sensors for wavelengths between 400-900 nm). FIG. 20b is a schematic illustration of a camera that is able to change the relative tilt between its lens and sensor planes according to the Scheimpflug principle. Housing 311 mounts a sensor 312 and lens 313. The lens 313 is tilted relative to the sensor 312. The tilt may be fixed according to the expected position of the camera relative to the ROI when the user wears the HMS, or may be adjusted using motor 314. The motor 314 may move the lens 313 and/or the sensor 312.

In one embodiment, an HMS device includes a frame configured to be worn on a user's head, and an inward-facing camera physically coupled to the frame. The inward-facing camera may assume one of two configurations: (i) the inward-facing camera is oriented such that the optical axis of the camera is above the Frankfort horizontal plane and pointed upward to capture an image of a region of interest (ROI) above the user's eyes, or (ii) the inward-facing camera is oriented such that the optical axis is below the Frankfort horizontal plane and pointed downward to capture an image of an ROI below the user's eyes. The inward-facing camera includes a sensor and a lens. The sensor plane is tilted by more than 2° relative to the lens plane according to the Scheimpflug principle in order to capture a sharper image.

In another embodiment, an HMS includes an inward-facing head-mounted camera that captures an image of an ROI on a user's face, when worn on the user's head. The ROI is on the user's forehead, nose, upper lip, cheek, and/or lips. The camera includes a sensor and a lens. And the sensor plane is tilted by more than 2° relative to the lens plane according to the Scheimpflug principle in order to capture a sharper image.

Because the face is not planar and the inward-facing head-mounted camera is located close to the face, an image captured by a camera having a wide field of view (FOV) and a low f-number may not be perfectly sharp, even after applying the Scheimpflug principle. Therefore, in some embodiments, the tilt between the lens plane and the sensor plane is selected such as to adjust the sharpness of the various areas covered in the ROI according to their importance for detecting the user's physiological response (which may be the user's emotional response in some cases). In one embodiment, the ROI covers first and second areas, where the first area includes finer details and/or is more important for detecting the physiological response than the second area. Therefore, the tilt between the lens and sensor planes is adjusted such that the image of the first area is shaper than the image of the second area.

In another embodiment, the ROI covers both a first area on the upper lip and a second area on a cheek, and the tilt is adjusted such that the image of the first area is shaper than the image of the second area, possibly because the upper lip usually provides more information and has more details relative to the cheek.

In still another embodiment, the ROI covers both a first area on the upper lip and a second area on the nose, and the tilt is adjusted such that the image of the first area is shaper than the image of the second area, possibly because the upper lip usually provides more information relative to the nose.

In still another embodiment, the ROI covers a first area on the cheek straight above the upper lip, a second area on the cheek from the edge of the upper lip towards the ear, and a third area on the nose. And the tilt between the lens plane and the sensor plane is adjusted such that the image of the first area is shaper than both the images of the second and third areas.

In still another embodiment, the ROI covers both a first area on the lips and a second area on the chin, and the tilt is adjusted such that the image of the first area is shaper than the image of the second area, possibly because the lips usually provides more information than the chin.

In still another embodiment, the camera is a visible-light camera, and the ROI covers both a first area on the lower forehead (including an eyebrow) and a second area on the upper forehead, and the tilt is adjusted such that the image of the first area is shaper than the image of the second area, possibly because the eyebrow provides more information about the user's emotional response than the upper forehead.

In still another embodiment, the camera is a thermal camera, and the ROI covers an area on the forehead, and the tilt is adjusted such that the image of a portion of the middle and upper part of the forehead (below the hair line) is shaper than the image of a portion of the lower part of the forehead, possibly because the middle and upper parts of the forehead are more indicative of prefrontal cortex activity than the lower part of the forehead, and movements of the eyebrows disturb the thermal measurements of the lower part of the forehead.

In one embodiment, the tilt between the lens plane and sensor plane is fixed. The fixed tilt is selected according to an expected orientation between the camera and the ROI when a user wears the frame. Having a fixed tilt between the lens and sensor planes may eliminate the need for an adjustable electromechanical tilting mechanism. As a result, a fixed tilt may reduce the weight and cost of the camera, while still providing a sharper image than an image that would be obtained from a similar camera in which the lens and sensor planes are parallel. The magnitude of the fixed tilt may be selected according to facial dimensions of an average user expected to wear the system, or according to a model of the specific user expected to wear the system in order to obtain the sharpest image.

In another embodiment, the system includes an adjustable electromechanical tilting mechanism configured to change the tilt between the lens and sensor planes according to the Scheimpflug principle based on the orientation between the camera and the ROI when the frame is worn by the user. The tilt may be achieved using at least one motor, such as a brushless DC motor, a stepper motor (without a feedback sensor), a brushed DC electric motor, a piezoelectric motor, and/or a micro-motion motor.

The adjustable electromechanical tilting mechanism configured to change the tilt between the lens and sensor planes may include one or more of the following mechanisms: (i) a mirror that changes its angle; (ii) a device that changes the angle of the lens relative to the sensor; and/or (iii) a device that changes the angle of the sensor relative to the lens. In one embodiment, the camera, including the adjustable electromechanical tilting mechanism, weighs less than 10 g, and the adjustable electromechanical tilting mechanism is able to change the tilt in a limited range below 30° between the two utmost orientations between the lens and sensor planes. Optionally, the adjustable electromechanical tilting mechanism is able to change the tilt in a limited range below 20° between the two utmost orientations between the lens and sensor planes. In another embodiment, the adjustable electromechanical tilting mechanism is able to change the tilt in a limited range below 10°. In some embodiments, being able to change the tilt in a limited range reduces at least one of the weight, cost, and size of the camera, which is advantageous for a wearable device. In one example, the camera is manufactured with a fixed predetermined tilt between the lens and sensor planes, which is in addition to the tilt provided by the adjustable electromechanical tilting mechanism. The fixed predetermined orientation may be determined according to the expected orientation between the camera and the ROI for an average user, such that the adjustable electromechanical tilting mechanism is used to fine-tune the tilt between the lens and sensor planes for the specific user who wears the frame and has facial dimensions that are different from the average user.

Various types of cameras may be utilized in different embodiments described herein. In one embodiment, the camera is a thermal camera that takes thermal measurements of the ROI with a focal plane array thermal sensor having an angle above 2° between the lens and sensor planes. Optionally, the thermal camera weighs below 10 g, is located less than 10 cm from the user's face, and the tilt of the lens plane relative to the sensor plane is fixed. The fixed tilt is selected according to an expected orientation between the camera and the ROI when the user wears the frame. Optionally, the system includes a computer to detect a physiological response based on the thermal measurements. Optionally, the computer processes time series measurements of each sensing element individually to detect the physiological response.

In another embodiment, the camera is a visible-light camera that takes visible-light images of the ROI, and a computer generates an avatar for the user based on the visible-light images. Some of the various approaches that may be utilized to generate the avatar based on the visible-light images are described in co-pending US patent publication 2016/0360970. Additionally or alternatively, the computer may detect an emotional response of the user based on (i) facial expressions in the visible-light images utilizing image processing, and/or (ii) facial skin color changes (FSCC), which result from concentration changes of hemoglobin and/or oxygenation.

It is to be noted that there are various approaches known in the art for identifying facial expressions from images. While many of these approaches were originally designed for full-face frontal images, those skilled in the art will recognize that algorithms designed for full-face frontal images may be easily adapted to be used with images obtained using the inward-facing head-mounted visible-light cameras disclosed herein. For example, the various machine learning techniques described in prior art references may be applied to feature values extracted from images that include portions of the face from orientations that are not directly in front of the user. Furthermore, due to the closeness of the visible-light cameras to the face, facial features are typically larger in images obtained by the systems described herein. Moreover, challenges such as image registration and face tracking are vastly simplified and possibly non-existent when using inward-facing head-mounted cameras. The reference Zeng, Zhihong, et al. "A survey of affect recognition methods: Audio, visual, and spontaneous expressions." IEEE transactions on pattern analysis and machine intelligence 31.1 (2009): 39-58, describes some of the algorithmic approaches that may be used for this task. The following references discuss detection of emotional responses based on FSCC: (i) Ramirez, Geovany A., et al. "Color analysis of facial skin: Detection of emotional state" in Proceedings of the IEEE Conference on Computer Vision and Pattern Recognition Workshops, 2014; and (ii) Wang, Su-Jing, et al. "Micro-expression recognition using color spaces", in IEEE Transactions on Image Processing 24.12 (2015): 6034-6047.

In still another embodiment, the camera is a light field camera that implements a predetermined blurring at a certain Scheimpflug angle, and decodes the predetermined blurring as function of the certain Scheimpflug angle. The light field camera may include an autofocusing of the image obtained using the tilting mechanism based on the principle that scene points that are not in focus are blurred while scene points in focus are sharp. The autofocusing may study a small region around a given pixel; the region is expected to get sharper as the Scheimpflug adjustment gets better, and vice versa. Additionally or alternatively, the autofocusing may use the variance of the neighborhood around each pixel as a measure of sharpness, where a proper Scheimpflug adjustment should increase the variance.

Various embodiments described herein involve an HMS that may be connected, using wires and/or wirelessly, with a device carried by the user and/or a non-wearable device. The HMS may include a battery, a computer, sensors, and a transceiver.

Figure 34A:
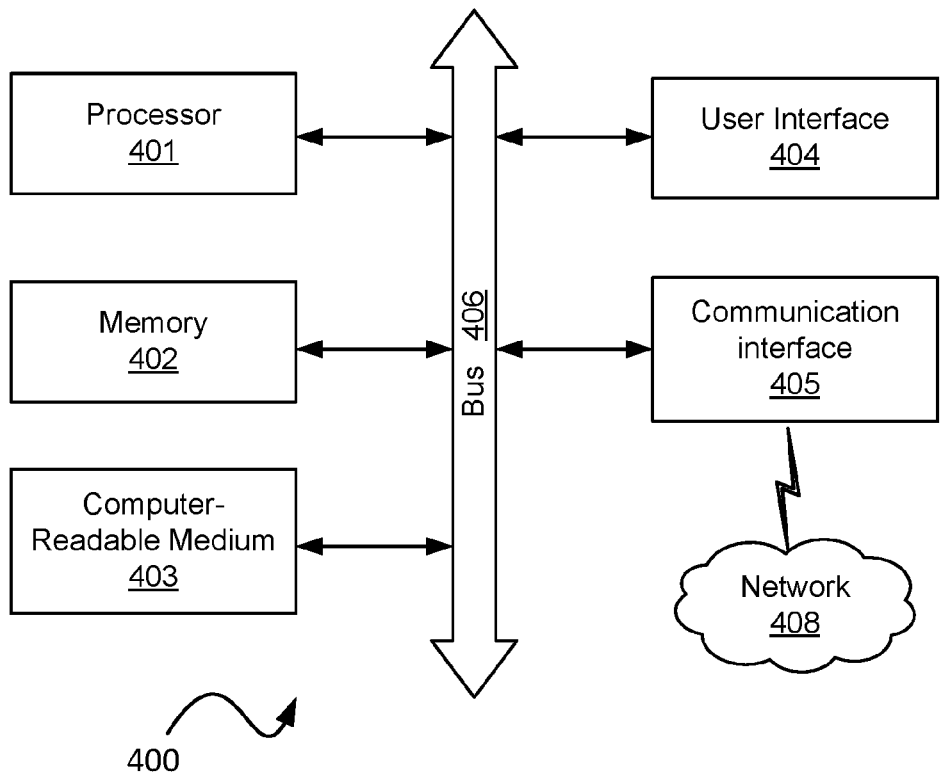
FIG. 34a and FIG. 34b are schematic illustrations of possible embodiments for computers.
Figure 34B:
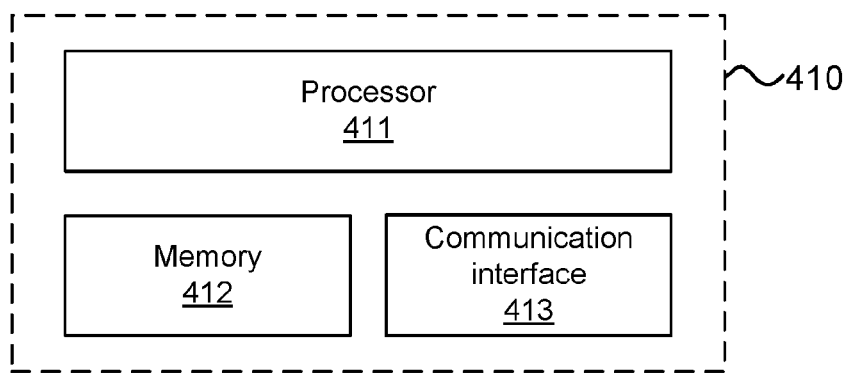

FIG. 34a and FIG. 34b are schematic illustrations of possible embodiments for computers (400, 410) that are able to realize one or more of the embodiments discussed herein that include a "computer". The computer (400, 410) may be implemented in various ways, such as, but not limited to, a server, a client, a personal computer, a network device, a handheld device (e.g., a smartphone), an HMS (such as smart glasses, an augmented reality system, and/or a virtual reality system), a computing device embedded in a wearable device (e.g., a smartwatch or a computer embedded in clothing), a computing device implanted in the human body, and/or any other computer form capable of executing a set of computer instructions. Herein, an augmented reality system refers also to a mixed reality system. Further, references to a computer or processor include any collection of one or more computers and/or processors (which may be at different locations) that individually or jointly execute one or more sets of computer instructions. For example, a first computer may be embedded in the HMS that communicates with a second computer embedded in the user's smartphone that communicates over the Internet with a cloud computer.

The computer 400 includes one or more of the following components: processor 401, memory 402, computer readable medium 403, user interface 404, communication interface 405, and bus 406. The computer 410 includes one or more of the following components: processor 411, memory 412, and communication interface 413.

Thermal measurements that are forwarded to a processor/computer may include "raw" values that are essentially the same as the values measured by thermal cameras, and/or processed values that are the result of applying some form of preprocessing and/or analysis to the raw values. Examples of methods that may be used to process the raw values include analog signal processing, digital signal processing, and various forms of normalization, noise cancellation, and/or feature extraction.

Functionality of various embodiments may be implemented in hardware, software, firmware, or any combination thereof. If implemented at least in part in software, implementing the functionality may involve a computer program that includes one or more instructions or code stored or transmitted on a computer-readable medium and executed by one or more processors. Computer-readable media may include computer-readable storage media, which corresponds to a tangible medium such as data storage media, or communication media including any medium that facilitates transfer of a computer program from one place to another. Computer-readable medium may be any media that can be accessed by one or more computers to retrieve instructions, code, data, and/or data structures for implementation of the described embodiments. A computer program product may include a computer-readable medium. In one example, the computer-readable medium 403 may include one or more of the following: RAM, ROM, EEPROM, optical storage, magnetic storage, biologic storage, flash memory, or any other medium that can store computer readable data.

A computer program (also known as a program, software, software application, script, program code, or code) can be written in any form of programming language, including compiled or interpreted languages, declarative or procedural languages. The program can be deployed in any form, including as a standalone program or as a module, component, subroutine, object, or another unit suitable for use in a computing environment. A computer program may correspond to a file in a file system, may be stored in a portion of a file that holds other programs or data, and/or may be stored in one or more files that may be dedicated to the program. A computer program may be deployed to be executed on one or more computers that are located at one or more sites that may be interconnected by a communication network.

Computer-readable medium may include a single medium and/or multiple media (e.g., a centralized or distributed database, and/or associated caches and servers) that store one or more sets of instructions. In various embodiments, a computer program, and/or portions of a computer program, may be stored on a non-transitory computer-readable medium, and may be updated and/or downloaded via a communication network, such as the Internet. Optionally, the computer program may be downloaded from a central repository, such as Apple App Store and/or Google Play. Optionally, the computer program may be downloaded from a repository, such as an open source and/or community run repository (e.g., GitHub).

At least some of the methods described herein are "computer-implemented methods" that are implemented on a computer, such as the computer (400, 410), by executing instructions on the processor (401, 411). Additionally, at least some of these instructions may be stored on a non-transitory computer-readable medium.

Herein, a direction of the optical axis of a VCAM or a CAM that has focusing optics is determined by the focusing optics, while the direction of the optical axis of a CAM without focusing optics (such as a single pixel thermopile) is determined by the angle of maximum responsivity of its sensor. When optics are utilized to take measurements with a CAM, then the term CAM includes the optics (e.g., one or more lenses). In some embodiments, the optics of a CAM may include one or more lenses made of a material suitable for the required wavelength, such as one or more of the following materials: Calcium Fluoride, Gallium Arsenide, Germanium, Potassium Bromide, Sapphire, Silicon, Sodium Chloride, and Zinc Sulfide. In other embodiments, the CAM optics may include one or more diffractive optical elements, and/or or a combination of one or more diffractive optical elements and one or more refractive optical elements.

When CAM includes an optical limiter/field limiter/FOV limiter (such as a thermopile sensor inside a standard TO-39 package with a window, or a thermopile sensor with a polished metal field limiter), then the term CAM may also refer to the optical limiter. Depending on the context, the term CAM may also refer to a readout circuit adjacent to CAM, and/or to the housing that holds CAM.

Herein, references to thermal measurements in the context of calculating values based on thermal measurements, generating feature values based on thermal measurements, or comparison of thermal measurements, relate to the values of the thermal measurements (which are values of temperature or values of temperature changes). Thus, a sentence in the form of "calculating based on $TH_{ROI}$" may be interpreted as "calculating based on the values of $TH_{ROI}$", and a sentence in the form of "comparing $TH_{ROI1}$ and $TH_{ROI2}$" may be interpreted as "comparing values of $TH_{ROI1}$ and values of $TH_{ROI2}$".

Depending on the embodiment, thermal measurements of an ROI (usually denoted $TH_{ROI}$ or using a similar notation) may have various forms, such as time series, measurements taken according to a varying sampling frequency, and/or measurements taken at irregular intervals. In some embodiments, thermal measurements may include various statistics of the temperature measurements (T) and/or the changes to temperature measurements (ΔT), such as minimum, maximum, and/or average values. Thermal measurements may be raw and/or processed values. When a thermal camera has multiple sensing elements (pixels), the thermal measurements may include values corresponding to each of the pixels, and/or include values representing processing of the values of the pixels. The thermal measurements may be normalized, such as normalized with respect to a baseline (which is based on earlier thermal measurements), time of day, day in the month, type of activity being conducted by the user, and/or various environmental parameters (e.g., the environment's temperature, humidity, radiation level, etc.).

As used herein, references to "one embodiment" (and its variations) mean that the feature being referred to may be included in at least one embodiment of the invention. Moreover, separate references to "one embodiment", "some embodiments", "another embodiment", "still another embodiment", etc., may refer to the same embodiment, may illustrate different aspects of an embodiment, and/or may refer to different embodiments.

Some embodiments may be described using the verb "indicating", the adjective "indicative", and/or using variations thereof. Herein, sentences in the form of "X is indicative of Y" mean that X includes information correlated with Y, up to the case where X equals Y. For example, sentences in the form of "thermal measurements indicative of a physiological response" mean that the thermal measurements include information from which it is possible to infer the physiological response. Stating that "X indicates Y" or "X indicating Y" may be interpreted as "X being indicative of Y". Additionally, sentences in the form of "provide/receive an indication indicating whether X happened" may refer herein to any indication method, including but not limited to: sending/receiving a signal when X happened and not sending/receiving a signal when X did not happen, not sending/receiving a signal when X happened and sending/receiving a signal when X did not happen, and/or sending/receiving a first signal when X happened and sending/receiving a second signal X did not happen.

Herein, "most" of something is defined as above 51% of the something (including 100% of the something). Both a "portion" of something and a "region" of something refer herein to a value between a fraction of the something and 100% of the something. For example, sentences in the form of a "portion of an area" may cover between 0.1% and 100% of the area. As another example, sentences in the form of a "region on the user's forehead" may cover between the smallest area captured by a single pixel (such as 0.1% or 5% of the forehead) and 100% of the forehead. The word "region" refers to an open-ended claim language, and a camera said to capture a specific region on the face may capture just a small part of the specific region, the entire specific region, and/or a portion of the specific region together with additional region(s).

Sentences in the form of "angle greater than 20°" refer to absolute values (which may be +20° or −20° in this example), unless specifically indicated, such as in a phrase having the form of "the optical axis of CAM is 20° above/below the Frankfort horizontal plane" where it is clearly indicated that the CAM is pointed upwards/downwards. The Frankfort horizontal plane is created by two lines from the superior aspects of the right/left external auditory canal to the most inferior point of the right/left orbital rims.

The terms "comprises," "comprising," "includes," "including," "has," "having", or any other variation thereof, indicate an open-ended claim language that does not exclude additional limitations. The "a" or "an" is employed to describe one or more, and the singular also includes the plural unless it is obvious that it is meant otherwise; for example, sentences in the form of "a CAM configured to take thermal measurements of a region ($TH_{ROI}$)" refers to one or more CAMs that take thermal measurements of one or more regions, including one CAM that takes thermal measurements of multiple regions; as another example, "a computer" refers to one or more computers, such as a combination of a wearable computer that operates together with a cloud computer.

The phrase "based on" is intended to mean "based, at least in part, on". Additionally, stating that a value is calculated "based on X" and following that, in a certain embodiment, that the value is calculated "also based on Y", means that in the certain embodiment, the value is calculated based on X and Y.

The terms "first", "second" and so forth are to be interpreted merely as ordinal designations, and shall not be limited in themselves. A predetermined value is a fixed value and/or a value determined any time before performing a calculation that compares a certain value with the predetermined value. A value is also considered to be a predetermined value when the logic, used to determine whether a threshold that utilizes the value is reached, is known before start performing computations to determine whether the threshold is reached.

The embodiments of the invention may include any variety of combinations and/or integrations of the features of the embodiments described herein. Although some embodiments may depict serial operations, the embodiments may perform certain operations in parallel and/or in different orders from those depicted. Moreover, the use of repeated reference numerals and/or letters in the text and/or drawings is for the purpose of simplicity and clarity and does not in itself dictate a relationship between the various embodiments and/or configurations discussed. The embodiments are not limited in their applications to the order of steps of the methods, or to details of implementation of the devices, set in the description, drawings, or examples. Moreover, individual blocks illustrated in the figures may be functional in nature and therefore may not necessarily correspond to discrete hardware elements.

Certain features of the embodiments, which may have been, for clarity, described in the context of separate embodiments, may also be provided in various combinations in a single embodiment. Conversely, various features of the embodiments, which may have been, for brevity, described in the context of a single embodiment, may also be provided separately or in any suitable sub-combination. Embodiments described in conjunction with specific examples are presented by way of example, and not limitation. Moreover, it is evident that many alternatives, modifications, and variations will be apparent to those skilled in the art. It is to be understood that other embodiments may be utilized and structural changes may be made without departing from the scope of the embodiments. Accordingly, this disclosure is intended to embrace all such alternatives, modifications, and variations that fall within the spirit and scope of the appended claims and their equivalents.

We claim:

1. A system configured to select a stressor, comprising:
   an inward-facing head-mounted thermal camera (CAM) configured to take thermal measurements of a region on a periorbital area ($TH_{ROI1}$) of a user; and
   a computer configured to:
   detect extents of stress based on $TH_{ROI1}$;
   receive indications of potential stressors to which the user was exposed while $TH_{ROI1}$ were taken; and
   select the stressor, from among the potential stressors, based on the indications and the extents.

2. The system of claim 1, wherein the region on the periorbital area is a region of the periorbital area of the right eye of the user; and further comprising a second inward-facing head-mounted thermal camera (CAM2) configured to take thermal measurements of a region on the periorbital area of the left eye ($TH_{ROI2}$) of the user; wherein the computer is further configured to detect the stress level also based on $TH_{ROI2}$; and further comprising a frame configured to be worn on the user's head, and to hold each of CAM and CAM2 less than 10 cm from the user's head; wherein each of CAM and CAM2 is weighs below 10 g.

3. The system of claim 1, further comprising second and third inward-facing head-mounted thermal cameras configured to take thermal measurements of regions on the forehead ($TH_{ROI2}$) of the user and the nose ($TH_{ROI3}$) of the user, respectively; and wherein the computer is further configured to detect the extents of stress also based on $TH_{ROI2}$ and $TH_{ROI3}$.

4. The system of claim 1, further comprising a second inward-facing head-mounted thermal camera configured to take thermal measurements of a region below the nostrils ($TH_{ROI2}$) of the user; wherein $TH_{ROI2}$ are indicative of the user's breathing, and the computer is further configured to detect the extents of stress also based on $TH_{ROI2}$.

5. The system of claim 1, further comprising a camera configured to take images of the surroundings of the user; wherein the computer is further configured to generate at least some of the indications based on analysis of the images.

6. The system of claim 1, wherein the computer selects the stressor based on at least one of the following assumptions (i) an average stress level of the user while being affected by the stressor is greater than an average stress level of the user while not being affected by the stressor, and (ii) during most of the time the user was affected by the stressor, an effect of the stressor, as manifested via changes to $TH_{ROI1}$, was higher than effects of most of the potential stressors.

7. The system of claim 6, wherein the indications comprise a certain indication of a stressor that is indicative of at least one of the following: the user conducted a certain activity, the user was at a certain location, and the user interacted with a certain entity.

8. The system of claim 6, wherein the computer is further configured to calculate, based on the indications and the extents, an effect of each potential stressor, and to select as the stressor a potential stressor with a maximal effect.

9. The system of claim 1, wherein the computer is further configured to generate a machine learning-based model based on the indications and extents, and to select the stressor based on an analysis of the model.

10. The system of claim 9, wherein the model comprises parameters of at least one of the following models: a regression model, a nave Bayes model, a Bayes network, a support vector machine for regression, and a neural network model.

11. The system of claim 9, wherein the computer is further configured to perform the analysis of the model by evaluating parameters of the model that correspond to the potential stressors, and to select as the stressor a certain potential stressor that has a corresponding parameter that is indicative of an effect that reaches a threshold, while effects indicated in parameters corresponding to most of the potential stressors do not reach the threshold.

12. The system of claim 9, wherein the computer is further configured to perform the analysis of the model by providing a predictor module with various inputs that correspond to different potential stressors that affect the user, and to calculate, based on the inputs and the model, various predicted stress levels; and wherein the stressor is selected from among the potential stressors, responsive to identifying that: (i) based on a first subset of the various predicted stress levels, the effect of the stressor reaches a threshold, and (ii) based on a second subset of the various predicted stress levels, the effects of most of the potential stressors do not reach the threshold.

13. A method for selecting a stressor, comprising:
   taking, utilizing an inward-facing head-mounted thermal camera (CAM), thermal measurements of a region on a periorbital area ($TH_{ROI1}$) of a user;
   detecting extents of stress based on $TH_{ROI1}$;
   receiving indications of times during which the user was exposed to potential stressors; and
   selecting the stressor, from among the potential stressors, based on the indications and the extents.

14. The method of claim 13, wherein the region on the periorbital area is a region of the periorbital area of the right eye of the user; and further comprising: taking, utilizing a second inward-facing head-mounted thermal camera, thermal measurements of a region on the periorbital area of the left eye $TH_{ROl2}$) of the user, and selecting the stressor also based on $TH_{ROl2}$.

15. The method of claim 13, further comprising taking, utilizing a second inward-facing head-mounted thermal camera, thermal measurements of a region on the forehead ($TH_{ROl2}$), and selecting the stressor also based on $TH_{ROl2}$.

16. The method of claim 13, further comprising taking, utilizing a second inward-facing head-mounted thermal camera, thermal measurements of a region on the nose ($TH_{ROl2}$), and selecting the stressor also based on $TH_{ROl2}$.

17. The method of claim 13, further comprising taking, utilizing a second inward-facing head-mounted thermal camera, thermal measurements of a region below the nostrils ($TH_{ROl2}$) of the user, and selecting the stressor also based on $TH_{ROl2}$; wherein $TH_{ROl2}$ are indicative of the user's breathing.

18. The method of claim 13, further comprising generating a machine learning-based model based on the indications and extents, and selecting the stressor based on an analysis of the model.

19. The method of claim 18, further comprising performing the analysis of the model by evaluating parameters of the model that correspond to the potential stressors, and selecting as the stressor a certain potential stressor that has a corresponding parameter that is indicative of an effect that reaches a threshold, while effects indicated in parameters corresponding to most of the other potential stressors do not reach the threshold.

20. The method of claim 18, further comprising performing the analysis of the model by: (i) providing a predictor module with various inputs that correspond to different potential stressors that affect the user; (ii) calculating, based on the inputs and the model, various predicted stress levels; (iii) determining, based on the various predicted stress levels, effects of the potential stressors; and (iv) selecting the stressor based on the effects; wherein an effect of the stressor reaches a threshold, while effects of most of the other potential stressors do not reach the threshold.

* * * * *